US010525137B2

(12) United States Patent
Connolly et al.

(10) Patent No.: US 10,525,137 B2
(45) Date of Patent: Jan. 7, 2020

(54) FORMULATIONS WITH REDUCED DEGRADATION OF POLYSORBATE

(71) Applicant: Genentech, Inc., South San Francisco, CA (US)

(72) Inventors: Brian Connolly, South San Francisco, CA (US); Lydia Hamburg, South San Francisco, CA (US); Emily Holz, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 15/393,147

(22) Filed: Dec. 28, 2016

(65) Prior Publication Data
US 2017/0189536 A1 Jul. 6, 2017

Related U.S. Application Data

(60) Provisional application No. 62/272,965, filed on Dec. 30, 2015.

(51) Int. Cl.
*A61K 47/40* (2006.01)
*A61K 47/26* (2006.01)
*A61K 9/08* (2006.01)
*A61K 39/395* (2006.01)
*A61K 9/00* (2006.01)

(52) U.S. Cl.
CPC ............ *A61K 47/40* (2013.01); *A61K 9/0019* (2013.01); *A61K 9/08* (2013.01); *A61K 39/395* (2013.01); *A61K 39/39591* (2013.01); *A61K 47/26* (2013.01); *C07K 2317/31* (2013.01); *C07K 2317/55* (2013.01)

(58) Field of Classification Search
None
See application file for complete search history.

(56) References Cited

U.S. PATENT DOCUMENTS

| | | |
|---|---|---|
| 4,120,649 A | 10/1978 | Schechter |
| RE30,985 E | 6/1982 | Cartaya |
| 4,419,446 A | 12/1983 | Howley et al. |
| 4,560,655 A | 12/1985 | Baker |
| 4,601,978 A | 7/1986 | Karin |
| 4,657,866 A | 4/1987 | Kumar |
| 4,665,077 A | 5/1987 | Stringfellow et al. |
| 4,676,980 A | 6/1987 | Segal et al. |
| 4,767,704 A | 8/1988 | Cleveland et al. |
| 4,816,567 A | 3/1989 | Cabilly et al. |
| 4,927,762 A | 5/1990 | Darfler |
| 4,965,199 A | 10/1990 | Capon et al. |
| 5,114,721 A | 5/1992 | Cohen et al. |
| 5,122,469 A | 6/1992 | Mather et al. |
| 5,229,275 A | 7/1993 | Goroff |
| 5,545,806 A | 8/1996 | Lonberg et al. |
| 5,545,807 A | 8/1996 | Surani et al. |
| 5,565,332 A | 10/1996 | Hoogenboom et al. |
| 5,569,825 A | 10/1996 | Lonberg et al. |
| 5,571,894 A | 11/1996 | Wels et al. |
| 5,587,458 A | 12/1996 | King et al. |
| 5,591,669 A | 1/1997 | Krimpenfort et al. |
| 5,591,828 A | 1/1997 | Bosslet et al. |
| 5,595,721 A | 1/1997 | Kaminski et al. |
| 5,625,126 A | 4/1997 | Lonberg et al. |
| 5,631,144 A | 5/1997 | Lemoine et al. |
| 5,633,425 A | 5/1997 | Lonberg |
| 5,641,870 A | 6/1997 | Rinderknecht et al. |
| 5,648,237 A | 7/1997 | Carter et al. |
| 5,661,016 A | 8/1997 | Lonberg et al. |
| 5,677,180 A | 10/1997 | Robinson et al. |
| 5,731,168 A | 3/1998 | Carter et al. |
| 5,736,137 A | 4/1998 | Anderson et al. |
| 5,759,573 A | 6/1998 | Kim |
| 5,776,456 A | 7/1998 | Anderson et al. |
| 5,789,199 A | 8/1998 | Joly et al. |
| 5,807,706 A | 9/1998 | Carter et al. |
| 5,821,333 A | 10/1998 | Carter et al. |
| 5,840,523 A | 11/1998 | Simmons et al. |
| 5,869,046 A | 2/1999 | Presta et al. |

(Continued)

FOREIGN PATENT DOCUMENTS

| | | |
|---|---|---|
| DE | 266710 A3 | 4/1989 |
| EP | 0 073 657 B1 | 6/1986 |

(Continued)

OTHER PUBLICATIONS

English translation of Specification of WO 2005/065717 A2, 31 pages; translation downloaded from European Patent Office on Jul. 6, 2018.*
Aachmann, F.L. et al. (2003). "Structural Background of Cyclodextrin-Protein Interactions," *Pyrotein Engineering* 16(12);905-912.
American College of Rheumatology. (Feb. 2002). "Guidelines for the Management of Rheumatoid," *Arthritis & Rheumatism* 46(2):328-346.
Anderson, K.C. et al. (Jun. 1984), "Expression of Human B Cell-Associated Antigens on Leukemias and Lymphomas: A Model of Human B Cell Differentiation," *Blood* 63(6):1424-1433.
Abellan, P.F et al. (2002). "Row Cytometry and the Study of Cerebrospinal Fluid in Leukaemic Patients: Additional Facts," *Br. J. Haematol.* 116:725-728.
Barbas, C.F. et al. (Sep. 1991). "Assembly of Combinatorial Antibody Libraries on Phage Surfaces: The Gene III Site," *Proc. Natl. Acad. Sci. USA* 88:7978-7982.

(Continued)

*Primary Examiner* — Savitha M Rao
*Assistant Examiner* — Gregg Polansky
(74) *Attorney, Agent, or Firm* — Morrison & Foerster LLP

(57) ABSTRACT

The invention provides methods for making such formulations and methods of using such formulations. The invention further provides methods of reducing polysorbate degradation, methods of reducing the amount of visible and sub-visible particles in an aqueous formulation, and methods of disaggregating polysorbate degradation products comprising adding a cyclodextrin to a formula comprising polysorbate and a polypeptide. The invention also provides aqueous formulations comprising a polypeptide, a polysorbate, and a cyclodextrin with reduced polysorbate degradation.

24 Claims, 17 Drawing Sheets

(56) References Cited

U.S. PATENT DOCUMENTS

| | | |
|---|---|---|
| 5,959,177 A | 9/1999 | Hein et al. |
| 6,013,605 A | 1/2000 | Rees et al. |
| 6,040,498 A | 3/2000 | Stomp et al. |
| 6,075,181 A | 6/2000 | Kucherlapati et al. |
| 6,150,584 A | 11/2000 | Kucherlapati et al. |
| 6,248,516 B1 | 6/2001 | Winter et al. |
| 6,417,429 B1 | 7/2002 | Hein et al. |
| 6,420,548 B1 | 7/2002 | Vézina et al. |
| 6,602,684 B1 | 8/2003 | Umaña et al. |
| 6,919,436 B2 | 7/2005 | Lihme et al. |
| 6,982,321 B2 | 1/2006 | Winter |
| 7,078,492 B2 | 7/2006 | Pirofski et al. |
| 7,087,409 B2 | 8/2006 | Barbas, III et al. |
| 7,125,978 B1 | 10/2006 | Vézina et al. |
| 7,153,507 B2 | 12/2006 | Van de Winkel et al. |
| 7,189,826 B2 | 3/2007 | Rodman |
| 7,695,936 B2 | 4/2010 | Carter et al. |
| 8,216,805 B2 | 7/2012 | Carter et al. |
| 8,383,114 B2 | 2/2013 | Sloey et al. |
| 2003/0157108 A1 | 8/2003 | Presta |
| 2003/0175884 A1 | 9/2003 | Umana et al. |
| 2003/0219433 A1 | 11/2003 | Hansen et al. |
| 2004/0093621 A1 | 5/2004 | Shitara et al. |
| 2004/0110704 A1 | 6/2004 | Yamane et al. |
| 2004/0132140 A1 | 7/2004 | Satoh et al. |
| 2004/0202658 A1 | 10/2004 | Benyunes |
| 2005/0025764 A1 | 2/2005 | Watkins et al. |
| 2005/0026229 A1 | 2/2005 | Reiter et al. |
| 2005/0100546 A1 | 5/2005 | Jakobovits et al. |
| 2005/0176122 A1 | 8/2005 | Lihme et al. |
| 2005/0239692 A1 | 10/2005 | Lindenblatt et al. |
| 2005/0287149 A1 | 12/2005 | Keler et al. |
| 2006/0059575 A1 | 3/2006 | Kusunoki et al. |
| 2006/0093598 A1 | 5/2006 | Chen et al. |
| 2006/0128654 A1 | 6/2006 | Tang et al. |
| 2006/0183887 A1 | 8/2006 | Jakobovits et al. |
| 2006/0246004 A1 | 11/2006 | Adams et al. |
| 2006/0258841 A1 | 11/2006 | Michl et al. |
| 2007/0086995 A1 | 4/2007 | Liu et al. |
| 2007/0178552 A1 | 8/2007 | Arathoon et al. |
| 2007/0225205 A1 | 9/2007 | Patten et al. |
| 2011/0287009 A1 | 11/2011 | Scheer et al. |
| 2011/0305639 A1 | 12/2011 | Lobo et al. |
| 2014/0314778 A1 | 10/2014 | Alavattam et al. |
| 2014/0322203 A1 | 10/2014 | Alavattam et al. |
| 2017/0189536 A1 | 7/2017 | Connolly |

FOREIGN PATENT DOCUMENTS

| | | |
|---|---|---|
| EP | 0 183 070 A2 | 6/1986 |
| EP | 0 183 070 A3 | 6/1986 |
| EP | 0 183 070 B1 | 6/1986 |
| EP | 0 244 234 A2 | 11/1987 |
| EP | 0 244 234 A3 | 11/1987 |
| EP | 0 244 234 B1 | 11/1987 |
| EP | 0 244 234 B2 | 11/1987 |
| EP | 0 308 936 A2 | 3/1989 |
| EP | 0 340 109 A2 | 11/1989 |
| EP | 0 340 109 A3 | 11/1989 |
| EP | 0 340 109 B1 | 11/1989 |
| EP | 0 402 226 A1 | 12/1990 |
| EP | 0 404 097 A2 | 12/1990 |
| EP | 0 404 097 A3 | 12/1990 |
| EP | 0 404 097 B1 | 12/1990 |
| JP | H-11-500404 A | 1/1999 |
| JP | 2000-226336 A | 8/2000 |
| JP | WO-2003/002152 A2 | 1/2003 |
| JP | 2003-510368 A | 3/2003 |
| JP | 2004-522803 A | 7/2004 |
| JP | 2005-534671 A | 11/2005 |
| JP | 2006-517540 A | 7/2006 |
| JP | 2007-524602 A | 8/2007 |
| JP | 2008-529499 A | 8/2008 |
| WO | WO-1987/00195 A1 | 1/1987 |
| WO | WO-1990/03430 A1 | 4/1990 |
| WO | WO-1990/03784 A1 | 4/1990 |
| WO | WO 1990/08187 A1 | 7/1990 |
| WO | WO-1990/11294 A1 | 10/1990 |
| WO | WO-1990/13646 A1 | 11/1990 |
| WO | WO-1991/00360 A1 | 1/1991 |
| WO | WO-1991/01133 A1 | 2/1991 |
| WO | WO-1991/10741 A1 | 7/1991 |
| WO | WO-1992/09690 A2 | 6/1992 |
| WO | WO-1992/09690 A3 | 6/1992 |
| WO | WO-1992/20373 A1 | 11/1992 |
| WO | WO-1993/01161 A1 | 1/1993 |
| WO | WO-1993/06213 A1 | 4/1993 |
| WO | WO-1993/08829 A1 | 5/1993 |
| WO | WO-1993/16185 A2 | 8/1993 |
| WO | WO-1993/16185 A3 | 8/1993 |
| WO | WO-1994/04690 A1 | 3/1994 |
| WO | WO-1994/04690 C1 | 3/1994 |
| WO | WO-1994/11026 A2 | 5/1994 |
| WO | WO-1994/11026 A3 | 5/1994 |
| WO | WO-1996/07754 A1 | 3/1996 |
| WO | WO-1996/27011 A1 | 9/1996 |
| WO | WO-1996/33735 A1 | 10/1996 |
| WO | WO-1996/34096 A1 | 10/1996 |
| WO | WO-1997/01633 A1 | 1/1997 |
| WO | WO-1997/17852 A1 | 5/1997 |
| WO | WO-1997/25428 A1 | 7/1997 |
| WO | WO-1998/24893 A2 | 6/1998 |
| WO | WO-1998/24893 A3 | 6/1998 |
| WO | WO-1998/050431 A2 | 11/1998 |
| WO | WO-1998/050431 A3 | 11/1998 |
| WO | WO-2001/24814 A1 | 4/2001 |
| WO | WO-2003/002152 A3 | 1/2003 |
| WO | WO-2003/002607 A1 | 1/2003 |
| WO | WO-2004/035607 A2 | 4/2004 |
| WO | WO-2004/035607 A3 | 4/2004 |
| WO | WO-2004/035607 C1 | 4/2004 |
| WO | WO-2004/056312 A2 | 7/2004 |
| WO | WO-2004/056312 A3 | 7/2004 |
| WO | WO-2004/064787 A2 | 8/2004 |
| WO | WO-2004/064787 A3 | 8/2004 |
| WO | WO-2004/091658 A1 | 10/2004 |
| WO | WO-2004/103404 A1 | 12/2004 |
| WO | WO-2005/065717 A2 | 7/2005 |
| WO | WO-2005/065717 A3 | 7/2005 |
| WO | WO-2006/084264 A2 | 8/2006 |
| WO | WO-2006/084264 A3 | 8/2006 |
| WO | WO-2006/133148 A2 | 12/2006 |
| WO | WO-2006/133148 A3 | 12/2006 |
| WO | WO-2007/019232 A2 | 2/2007 |
| WO | WO-2007/019232 A3 | 2/2007 |
| WO | WO-2008/071394 A1 | 6/2008 |
| WO | WO-2008/122007 A1 | 10/2008 |
| WO | WO-2010/057107 A1 | 5/2010 |
| WO | WO-2011/089062 A2 | 7/2011 |
| WO | WO-2011/089062 A3 | 7/2011 |
| WO | WO-2013/164837 A1 | 11/2013 |
| WO | WO-2014/141152 A2 | 9/2014 |
| WO | WO-2014/141152 A3 | 9/2014 |

OTHER PUBLICATIONS

Barbas, C.F. et al. (May 1992). "Semisynthetic Compinatorial Antibody Libraries: A Chemical Solution to the Diversity Problem," *Proc. Natl. Acad. Sci. USA* 89:4457-4461.

Barnes, D. et al. (1980). "Methods for Growth of Cultured Cells in Serum-Free Medium," *Anal. Biochem.* 102:255-270.

Bass, S. et al. (1990). "Hormone Phage: An Enrichment Method for Variant for Variant Proteins with Altered Binding Properties," *Proteins* 8:309-314.

Bent, D.V. et al. (May 14, 1975). "Excited State Chemistry of Aromatic Amino Acids and Related Peptides," *Journal of the American Chemical Society* 97(10)2613-2619.

Berentsen et al. (2001). "Favourable Response to Therapy With the Anti-CD20 Monoclonal Antibody Rituximab in Primary Chronic Cold Agglutinin Disease," *Br. J. Haematol.* 115: 79-83.

Berentsen et al. (2004). "Rituximab for Printery Chronic Cold Agglutinin Disease: A Prospective Study of 37 Courses of Therapy in 27 Patients," *Blood* 103:2925-2928.

(56) References Cited

OTHER PUBLICATIONS

Boerner, P. et al. (Jul. 1, 1991), "Production of Antigen-Specific Human Monoclonal Antibodies from In Vitro-Primed Human Splenocytes," *J. Immunol.* 147(1):86-95.
Borisov, O.V, et al. (2014, e-pub Jan. 11, 2015). "Oxidative Degradation of Polysorbate Surfactants Studied by Liquid Chromatography—Mass Spectrometry," *J. Pharm. Sci.* 104:1005-1018.
Brennan, M. et al. (Jul. 5, 1985). "Preparation of Bispecific Antibodies by Chemical Recombination of Monoclonal immunoglobulin $G_1$ Fragments," *Science* 229:81-83.
Brodeur, B.R. et al. (1987). "Mouse-Human Myeloma Partners for the Production of Heterohybridomas," in *Monoclonal Antibody Production Techniques and Applications* pp. 51-63.
Bruggemann, M. et al. (1993), "Designer Mice: The Production of Human Antibody Repertoires in Transgenic Animals," *Year Immunol.* 7:33-40.
Caron, P.C. et al. (Oct. 1, 1992). "Engineered Humanized Dimeric Forms of Igg Are More Effective Antibodies," *J. Exp Med.* 176:1191-1195.
Carpenter, J.F. et al. (Nov. 8, 1997). "Rational Design of Stable Lyophilized Protein Formulations: Some Practical Advice," *Pharmaceutical Research* 14(8):969-975.
Carter, P. et al. (Feb. 1992). "High Level *Escherichia coli* Expression and Production of a Bivalent Humanized Antibody Fragment," *Bio/Technology* 10:163-167.
Carter, P. et al. (May 1992). "Humanization of an Anti-p185$^{HER2}$ Antibody for Human Cancer Therapy," *Proc. Natl. Acad. Sci. USA* 89:4285-4289.
Challa, R. et al. (2005). "Cyclodextrins in Drug Delivery: An Updated Review," *AAPS Pharm. Sci. Tech.* 6:E329-E357.
Champe M., et al. (Jan. 1995). "Monoclonal Antibodies that Block the Activity of Leulocyte Function-Associated Antigen 1 Recognize Three Discrete Epitopes in the Inserted Domain of CD11a," *The Journal of Biological Chemistry* 270(3):1388-1394.
Charlton, K. A. (2003). "Expression and Isolation of Recombinant Antibody Fragments in *E coli*," in *Methods in Molecular Biology* 248:245-254.
Chothia, C. et al. (Apr. 23, 1987). "Canonical Structures for the Hypervariable Regions of Immunoglobulins," *J. Mol. Biol.* 196:901-917.
Clackson, T. et al. (Aug. 15, 1991). "Making Antibody Fragments Using Phage Display Libraries," *Nature* 352:624-628.
Clark, E.A. et al. (1989). "Structure, Function, and Genetics of Human B Cell-Associated Surface Molecules," *Adv. Can. Res.* 52:81-149.
Cole, S.P.C. et at. (1985). "The EBV-Hybridoma Technique and its Application to Human Lung Cancer," *Monoclonal Antibodies and Cancer Therapy* pp. 77-96.
Coll, A.P. et al. (Jan. 15, 2004). "Rituximab Therapy for Type B Syndrome of Severe Insulin Resistance," *N. Engl. J. Med.* 350:310-311.
Cragg, M.S. et al. (Feb. 1, 2003). "Complement-Mediated Lysis by Anti-CD20 Mab Correlates With Segregation Into Lipid Rafts," *Blood* 101(3):1045-1052.
Cromwell, M.E.M. et al. (2006). "Protein Aggregation and Bioprocessing," *The AAPS Journal* 2006 8(3):E572-E579.
Cross, A.H. et al. (2003). (Abstract) "Preliminary Results From a Phase II Trial of Rituximab in MS," *Eighth Annual Meeting of the Americas Committees for Research and Treatment in Multiple Sclerosis* pp. 20-21.
Cunningham, B.C. et al. (Jun. 2, 1989). "High-Resolution Epitope Dipping of hGH-Receptor Interactions by Alanine-Scanning Mutagenesis," *Science* 244:1081-1085.
D'Arena, G. et al. (2003). "Late and Long-Lasting Response in an Adult Chronic Idiopathic Thrombocytopenic Purpura After Extended Course of Rituximab," *Leuk. Lymphoma* 44(3):561-562.
Devita, S. et al. (2002). "Efficacy and Safety, of Rituximab Treatment in Type II Mixed Cryoglbulinemia," 2002 Annual Scientific Meeting, Oct. 24-29, 202. New Orleans, Louisiana, *Arthritis Rheum.* 46(Suppl. 9):S206, Abstract No. 469.

Duchosal, M.A. et al. (Jan. 1992). "Immunization of Hu-PBL-SCID Mice and the Rescue of Human Monoclonal Fab Fragments through Combinatorial Libraries," *Nature* 355:258-262.
Dupay , A. et al. (Jan. 2004). "Treatment of Refractory Pemphigus Vulgaris With Rituximab (Anti-CD20 Monoclonal Antibody," *Arch. Dermatol.* 140:91-95.
Edwards; J.G.W. et al. (2002). "Efficacy and Safety of Rituximab, A B-Cell Targeted Chimeric Monoclonal Antibody: A Randomized, Placebo-Controlled Trial in Patients With Rheumatoid Arthritis," *Arthritis Rheum.* 46(Suppl. 9):S197.
Edwards, J.C.W. et al. (2002). "B-Lymphocyte Depletion Therapy in Rheumatoid Arthritis and Other Autoimmune Disorders," *Biochem Soc. Trans.* 30:824-828.
Einfeld, D.A. et al. (1988). "Molecular Cloning of the Human B Cell CD20 Receptor Predicts a Hydrophobic Protein With Multiple Transmembrane Domains," *EMBO J.* 7(3):711-717.
Eisenberg, R. (2003). "SLE—Rituximab in Lupus," *Arthritis. Res. Ther.* 5:157-159.
Elyan B. M. et al. (Jan. 1996). "Evaluation of the Effect of Different Fatty Acids on the Percutaneious Absorption of Metaproterenol. Sulfate," *J. Pharm. Sci.* 85(1):101-105.
Embleton, M.J. et al. (1992). "In-Cell PCR from mRNA: Amplifying and Linking the Rearranged Immunoglobulin Heavy and Light Chain V-Genes within Single Cells," *Nucleic Acids Research* 20(15).3831-3837.
Emery, P. et al. (Sep. 2003). "Sustained Efficacy at 48 Weeks After Singte Treatment Course of Rituximab in Patients With Rheumatiod Arthritis," 2003 Annual Scientific Meeting, Oct. 23-28, 2009, Orlando, Florida, *Arthritis Rheum.* 48(9 Supp.:9):S439, Abstract No. 1095.
Even, M.S. et al. (Jan. 2006). "Serum-Free Hybridoma Culture: Ethical, Scentific and Safety Considerations," *Trends in Biotechnology* 24(3):105-108.
Fang, L. et al. (2011, e-pub, Sep. 6, 2011). "Characterization of N-Acetyltryptophan Degradation Products in Concentrated Human Serum Albumin Solutions and Devebpment of an Automated High Performance Liquid Chromatography-Mass Spectrometry Method for their Quantitation," *Journal of Chromatography A* 1218:7316-7324.
Fedorova, M. et al. (Jul. 2010). "Quantitative Evaluation of Tryptophan Oxidation in Actin and Troponin 1 from Skeletal Muscles Using a Rat Model of Acute Oxidative Stress," *Proteomics* 10(14):2692-2700.
Fellouse, F.A. et al. (Aug. 24, 2004). "Synthetic Antibodies from a Four-Amino-Acid Code: A Dominant Role for Tyrosine in Antigen Recognition," *Proc. Natl. Acad. Sci. USA* 101(34):12467-12472.
Fsihwild, D.M. et al. (May 1996). "High-Avidity Human IgGk Monoclonal Antibodies from a Novel Strain of Minilocus Transgenic Mice," *Nature Biotechnology* 14:845-851.
Fleer, et al. (Oct. 1991). "Stable Multicopy Vectors for High-Level Secretion of Recombinant Human Serum Albumin by *Kluyveromyces* Yeasts," *Bio/Technology* 9:968-975.
Franek, F. (2005). "Oligopeptides as Tools for Improving Productivity of Hybridoma Cells Cultures," *Trends in Monoclonal Antibody Research* pp. 111-122.
Frokjaer, S et al. (Apr. 2005). "Protein Drug Stability: A Formulation Challenge," *Nat. Rev. Drug. Discov.* 4(4)298-306.
Gazzano-Santoro, H. et al. "A Non-Radioactive Complement-Dependent Cytotoxicity Assay Anti-CD20 Monoclonal Antibody," *J. Immunol. Methods* 202:163-171.
Gerngross, T.U. (Nov. 2004). "Advances in the Production of Human Therapeutic Proteins in Yeasts and Filamentous Fungi," *Nature Biotechnology* 22(11):1409-1414.
Gescuk, B.D. et al. (2002). "Novel Therapeutic Agent for Systemic Lupus Erythematosus," *Current Opinion in Rheumatology* 14:515-521.
Glennie, M.J. et al. (2003). "Renaissance of Cancer Therapeutic Antibodies," *Drug Discovery Today* 8(11):503-510.
Goding, J.W. (1983). "Production of Monoclonal Antibodies," Chapter in *Monoclonal Antibodies: Principles and Practice* pp. 59-103.

(56) References Cited

OTHER PUBLICATIONS

Golovanov, A.P. et al. (2004). "A Simple Method for Improving Protein Solubility and Long-Term Stability," *J. Am. Chem. Soc.* 126:8933-8939.

Gorman, C. et al. (2004). "Does B Cell Depletion Have a Role to Play to the Treatment of Systemic Lupus Erythematosus?," *Lupus* 13:312-316.

Graham, F.L. et al. (Feb. 10, 1977). "Characteristics of a Human Cell Line Transformed by DNA From Human Adenovirus Type 5," *J. Gen Virol.* 36:59-72.

Gram, H. et al. (Apr. 1992). "In Vitro Selection and Affinity Maturation of Antibodies from a Naive Combinatorial Immunoglobulin Library," *Proc. Natl. Acad. Sci. USA* 89:3576-3580.

Griffiths, A.D. et al. (1993). "Human Anti-Self Antibodies with High Specificity from Phage Display Libraries," *The EMBO Journal* 12(2):725-734.

Gruber, M. et al. (1994). "Efficent Tumor Cell Lysis Mediated by a Bispecific Singe Chain Antibody Expressed in *Escherichia coli*," *Journal of Immunology* pp. 5368-5374.

Guss, B. et al. (1986). "Structure of the IgG-Binding Regions of Streptococcal Protein G," *The EMBO Journal* 5:1567-1575.

Ham R.G. et al. (1979). "Media and Growth Requirements," *Methods in Enzymology* 58:44-93.

Hamers-Casterman, C. et al. (Jun. 3, 1993). "Naturally Occurring Antibodies Devoid of Light Chains," *Letters to Nature* 363:446-448.

Hammerling, G.J. et al. (1981). "Production of Antibody-Producing Hybridomas in the Rodent System," *Monoclonal Antibodies and T-Cell Hybridomas* 3:563-587.

Hammond, S. et al. (Oct. 2011, e-pub. Nov. 22, 2011). "Chinese Hamster Genome Database: An Online Resource for the CHO Community," *Biotechnology and Bioengineering* 109(6):1353-1356.

Harris, W.J. (Jul. 1995). "Therapeutic Monoclonal," *Biochemical Society Transaction* 23:1035-1038.

Hawkins, R.E. et al. (Jan. 1992). "Selection of Phage Antibodies by Binding Affinity Mimicking Affinity Maturation," *J. Mol. Biol.* 226: 889-896.

Hillgren, A. et al. (2002). "Protection Mechanism of Tween 80 During Freeze-Thawing of a Model Protein, LDH," *International Journal of Pharmaceutics* 237:57-69.

Hogrefe, H.H. et al. (1993). "A Bacteriophage Lambda Vector for the Cloning and Expression of Immunoglobulin Fab Fragments on the Surface of Filamentous Phage," *Gene* 128:119-126.

Holliger, P. et al. (Jul. 1993). "'Diabodies': Small Bivalent and Bispecific Antibody Fragments," *Proc. Natl. Acad. Sci. USA* 90:6444-6448.

Hongo, J.S. et al. (1995). "Development and Characterization of Murine Monoclonal Antibodies to the Latency-Associated Peptide of Transforming Growth Factor $\beta_1$," *Hybridoma* 14(3)253-260.

Hoogenboom, H.R. et al. (1991). "Multi-Subunit Proteins on the Surface of Filamentous Phage: Methodologies for Displaying Antibody (Fab) Heavy and Light Chains," *Nucleic Acids Research* 19(15):4133-4137.

Hoogenboom, H.R. et al. (1992). "By-Passing Immunisation Humn Antibodies from Synthetic Repertoires of Germline $V_H$ Gene Segments Rearranged in Vitro," *J. Mol. Biol.* 227:381-388.

Hoogenboom, H.R. et al. (2002). "Overview of Antibody Phage-Display Technology and Its Applications," *Methods in Molecular Biology* 178:1-37.

Hudson, P.J. et al. (2003). "Engineered Antibodies," *Nature Medicine* 9(1):129-134.

Hurle, M.R. et al. (1994). "Protein Engineering Techniques for Antibody Humanization," *Current Opinion in Biotechnology* 5:428-433.

Irie, T. et al. (1999). "Cyclodextrins in Peptide and Protein Delivery," *Advanced Drug Delivery Reviews* 36 101-123.

Itakura, K. et al. (Oct. 8, 1993). "Selective Formation of Oxindole- and Formylkynurenine-Type Products from Tryptophan and its Peptides Treated with a Superoxide-Generating System in the Presence of Iron(III)-EDTA: A Possible Involvement with Iron-Oxygen Complex," *Chem. Res. Toxicol.* 7(2):185-190.

Jakobovits, A. et al. (Mar. 18, 1993). "Germ-Line Transmission and Expression of a Human-Derived Yeast Artificial Chromosome," *Nature* 362:255-258.

Jakobovits, A. et al. (Mar. 1993). "Analysis of Homozygous Mutant Chimeric Mice: Deletion of the Immunoglobulin Heavy-Chain Joining Region Blocks B-Cell Development and Antibody Production," *Proc. Natl. Acad, Sci. USA* 90:2551-2555.

Jiskoot, W. et al. (2006). "What Makes Protein Drugs Different? Pharmaceutical Aspects," *EJHP Practice* 12:20-21.

John, B. et al. "Detection of Homologous Proteins by an Intermediate Sequence Search," *Protein Sci.* 13:54-54, (2004).

Johnson K.S. et al. (1993). "Human Antibody Engineering," Current Opinion in Structural Biology 3:564-571.

Johnson, G. et al. (2004). "The Kabat Database and a Bioinformatics Example," *Methods in Molecular Biology* 248:11-25.

Jones, E.W. (Jan. 1977). "Proteinase Mutants of *Saccharonyces cerevisiae*," *Genetics* 85:23-33.

Jones, P.T. et al. (May 29, 1986). "Replacing the complementarity Determining Regions in a Human Antibody with those from a Mouse," *Nature* 321:522-525.

Jones, S.T. et al. (1991). "Rapid PCR-Cloning of Full-Length Mouse Immuoglobulin Variable Regions," *Bio/Technology* 9:88-89.

Jones, A.J.S. et al. (1993). "Analysis of Polypeptides and Proteins," *Advanced Drug Delivery Reviews* 10:29-90.

Kerwin, B.A. (Aug.). "Polysorbates 20 and 80 used in the Formulation of Protein Biotherapeutics: Structure and Degradation Pathways," *Journal of Pharmaceutical Sciences* 97(8):2924-2935.

Kim J. et al. (Jan. 2, 2014, e-pub. Nov. 15, 2013). "Quantitation of Low Concentrations of Polysorbates in High Protein Concentration Formulations by Solid Phase Extraction and Cobalt-Thiocyanate Derivatization," *Analytica Chimica Acta* 806:144-151.

Kishore, R.S.K., (2010) "Degradation of Polysorbates 20 and 80 Studies on Thermal Autoxidation and Hydrolysis," *Journal of Pharmaceutical Sciences* pp. 1-11.

Kishore, R.S. K. et al. (May 2011, e-pub, Mar. 3, 2011). "The Degradation of Polysorbates 20 and 80 and its Potential Impact on the Stability of Biotherapeutics," *Pharm. Res.* 28(5):1194-1210.

Klenin, K.V., et al. (Sep. 2011, e-pub, Jun. 8, 2011). "Derivatives of molecutar Surface Area and Volume: Simple and Exact Analytical Formulas," *Journal of Computational Chemistry* 32:2647-2653.

Kohler, G. et al. (Aug. 7, 1975). "Continuous Cultures of Fused Cells Secreting Antibody of Predefined Specificity," *Nature* 256:495-497.

Kostelny, S.A. et al. (Mar. 1, 1992), "Formation of a Bispecific Antibody by the Use of Leucine Zippers," *The Journal of Immunology* 148(5):1547-1553.

Kozbor, D. et al. (Dec. 1984), "A Human Hybrid Myeloma for Production of Human Monoclonal Antibodies," *The Journal of Immunology* 133(6):3001-3005.

Kreilgaard, L. et al. (Dec. 1998, e-pub. Oct. 7, 1998). "Effect of Tween 20 on Freeze-Thaw ing- and Agitation-Induced Aggregation of Recombinant Human Factor XIII," *Journal of Pharmaceutical Sciences* 87(12):1597-1603.

Kumrau, O.S. et al. (Oct. 2012 e-pub Jun. 25, 2012). "Compatibility, Physical Stability, and Characterization of an IgG4 Monoclonal Antibody after Dilution into Different Intravenous Administration Bags," *Journal of Pharmaceutical Sciences* 101(10),3636-3650.

Labrenz, S.R. (2014 e-pub Jun. 17, 2014). "Ester Hydrolysis of Polysorbate 80 in mAb Drug Product: Evidence in Support of the Hypothesized Risk After the Observation of Visible Particulate in mAb Formulations," *Journal of Pharmaceutical Sciences* 103:2268-2277.

Layios, N. et al. (2001), "Remission of Severe Cold Agglutinin Disease After Rituximab Therapy," *Leukemia* 15:187-188.

Leandro, M.J. et al. (Oct. 2002). "Clnical Outome in 22 Patients With Rheumetoid Arthritis Treated With B Lymphocyte Depletion," *Ann. Rheum. Dis.* 61 (10):983-888.

Leandro, M.J. et al. (Oct. 2002). "An Open Study of B Lymphocyte Depletion in Systemic Lupus Erythematosus," *Arthritis Rheum.* 46(10): 2673-2677.

(56) References Cited

OTHER PUBLICATIONS

Lee, C. V. et al. (Jan. 2004). "Bivalent Antibody Phage Display Mimics Natural Immunoglobulin," *Journal of Immunological Methods* 284(1-2):119-132.

Lee, C.V. et al. (2004). "High-Affinity Human Antibodies from Phage-Displayed Synthetic Fab Libraries with a Single Framework Scaffold," *J. Mol. Biol.* 340(5):1073-1093.

Lee, R.C. et al. (2006). "Surfactant Copolymers Prevent Aggregation of Heat Denatured Lysozyme," *Ann. Biomed. Eng.* 34:1190-1200.

Lee, K. et al., (2015). "A Chinese Hamster Ovary Cell Host Cell Protein that Impacts PS-80 Degradation," *AccBio Conference* p. 1.

Lehrnbecher, T. et al. (1999). "Variant Genotypes of the Low-Affinity Fcγ Receptors in Two Control Populations and a Review of Low-Affinity Fcγ Receptor Polymorphisms in Control and Disease Populations," *Blood* 94:4220-4232.

Leung, D.W. et al. (Aug. 1, 1989). "A Method for Random Mutagenesis of a Defined DNA Segment Using a Modified Polymerase Chain Reaction," *Technique* 1(1)11-15.

Li, H. et al. (Feb. 2006 e-pub. Jan. 22, 2006). "Optimization of Humanized IgGs in Glycoengineered *Pichia Pastoris*," *Nature Biotechnology* 24(2):210-215.

Li, J. et al. (Mar. 7, 2006). "Human Antibodies for Immunotherapy Development Generated via a Human B Cell Hybridoma Technology." *The Natl. Acad. Sci. USA* 103(10):3557-3562.

Li, Y. et al. (Jul. 2014 e-pub, Jul. 1, 2014), "Characterization of the Degradation Products of color-Changed Monoclonal Antibody: Tryptophan-Derived Chromphores," *Analytical Chemistry* 86(14)6850-6857.

Lindmark, R. et al. (1983). "Binding of Immunoglobulins to Protein A and Immunoglobulin Levels in Mammalian Sera," *Journal of Immunological Methods* 62:1-13.

Liu, L. et al. (Aug. 2013 e-pub. May 27, 2013). "The Effects of Excipients on Protein Aggregation During Agitation: An Interfacial Shear Rheology Study," *Pharmaceutical Biotechnology* 102(8):2460-2470.

Lonberg, N. et al. (Apr. 28, 1994). "Antigen-Specific Human Antibods from Mice Comprising Four Distinct Genetic Modifications," *Nature* 368:856-859.

Lonberg, N. et al. (1995). "Human Antibodies from Transgenic Mice," *Intern. Rev. Immunol.* 13: 65-93.

Maa, Y.F. et al. (May 1996). "Mmembrane Fouling in Sterile Filtration of Recombinant Human Growth Hormone," *Biotechnol. Bioeng.* 50:319-328.

Maa, Y.F. et al. (Jul. 1998). "Investigation on Fouling Mechanisms for Recombinant Human Growth Hormone Sterile Filtration," *Journal of Pharmaceutical Sciences* 87(7):808-812.

Mahler, H.C. et al. (Mar. 2010.) "Understanding Polysorbates in Protein Formulation," *Abstr Pap Am Chem S*. Abstract No. 169.

Marks, J.D. et al. (Sep. 1991). "By-Passing Immunization Human Antibodies from V-Gene Libraries Displayed on Phage," *J. Mol. Biol.* 222: 581-597.

Marks, J.D. et al. (Jul. 1992). "By-Passing Immunization: Building High Affinity Human Antibodies by Chain Shuffling," *Bio/Technology* 10:779-783.

Mather, J.P. et al. (1980). "Establishment and Characterization of Two Distinct Mouse Testicular Epithelial Cell Lines," *Biology of Reproduction* 23:243-251.

Mather, J.P. et al. (1982). "Culture of Testicular Cells in Hormone-Supplemented Serum-Free Medium," *Annals New York Academy of Sciences* pp. 44-68.

Matsuda, F. at al. (Jan. 1993). "Structure and Physical Map of 64 Variable Segments in the 3' 0.8-Megabase Region of the Human Immunoglobulin Heavy-Chain Locus," *Nature Genetics* 3:88-94.

McCafferty, J. et al. (Dec. 6, 1990). "Phaage Antibodies: Filamentous Phage Displaying Antibody Variable Domains," *Nature* 348:552-554.

Milstein, C. et al., (Oct. 6, 1983). "Hybrid Hybridomas and their use in Immunohistochemistry," *Nature* 305:537-539.

Mishra, R. et al. (2005). "Efficient Refolding of Aggregation-Prone Citrate Synthase by Polyol Osmolytes: How Well Are Protein Folding and Stability Aspects Coupled?," *J. Biol. Chem.* 280:15553-15560.

Morimoto, K. et al. (1992). "Single-Step Purification of F(Ab'), Fragments of Mouse Monoclonal Antibodies (Immunoglobulins G1) by Hydrophobic Interaction High Performance Liquid Chromatography using TSkgel Phenyl-5PW," *Journal of Biochemical and Biophysical Methods* 24:107-117.

Morrison, S. L. et al. (Nov. 1984), "Chimeric Human Antibody Molecules: Mouse Antigen-Binding Domains with Human Constant Region Domains," *Proc. Natl. Acad. Sci. USA* 81:6851-6855.

Morrison, S. L. (Apr. 28, 1994). "Success in Specification," *Nature* 368: 812-813.

Munson, P.J. et al. (Mar. 4, 1980). "LIGAND: A Versatile Computerized Approach for Characterization of Ligand-Binding Systems," *Analytical Biochemistry* 107:220-239.

Nema, S. et al. (1997). "Excipients and Their Use in Injectable Products," *PDA Journal of Pharmaceutical Science and Technology* 51:166-171.

Neuberger, M. (Jul. 1996). "Generating High-Avidity Human Mabs in Mice," *Nature Biotechnology* 14:826.

Ni, J. (Oct. 23, 2006). "Research Progress and Future Perspectives in Antibodomics and Antibodomic Drugs," *Xiandai Mianyixue* 26(4)265-268, Abstracts Only.

Nicolaou, K.C. et al. (Feb. 1, 1994). "Calicheamicin $\theta^I_1$: A Rationally Designed Molecule With Extremely Potent and Selective DNA Cleaving Properties and Apoptosis Inducing Activity," *Angew. Chem. Intl. Ed. Engl.* 33(2)183-186.

Nilson, B.H.K. (Aug. 26, 1993). "Purification of Antibodies using Protein L-binding Framework Structures in the Light Chain Variable Domain," *Journal of Immunological Methods* 164(1):33-40.

Niwa, R. et al. (Mar. 15, 2004). "Defucosylated Chimeric Anti-OC Chemokine Receptor 4 IgG1 With Enhanced Antibody-Dependent Cellular Cytotoxicity Show s Potent Therapeutic Activity to T-Cell Leukemia and Lymphoma," *Cancer Res.* 84(6):2127-2133.

Offner, H. et al. (Jan. 25, 1991). "T cell Receptor Peptide Therapy Triggers Autoregulation of Experimental Encephalomyelitis," *Science* 251:430-432.

Orlandi, R, et al. (May 1989). "Cloning Immunoglobulin Variable Domains for Expression by the Polymerase Chain Reaction," *Proc. Natl. Acad. Sci. USA* 86: 3333-3837.

Ørum, H. et al. (1993). "Efficient Method for Constructing Comprehensive Murine Fab Antibody Libraries Displayed on Phage," *Nucleic Acids Res.* 21(19):4491-4498.

Otzen, D.E. et al. (2002). "Structural Basis for Cyclodextrins' Suppression of Human Growth Hormone Aggregation," *Protein Sci.* 11:1779-1787.

Pearlman, R. et al. (1991). "Analysis of Retain Drugs," *Peptide and Protein Drug Delivery* pp. 247-301.

Pestronk, A. (2003). "Treatment of IgM Antibody Associated Polyneuropathies Using Rituximab," *J. Neurol. Neurosurg. Psychiatry* 74:485-489.

Pluckthün, A. (1994). "Antibodies from *Escherichia coli*," *The Pharmacology of Monoclonal Antibodies* pp. 269-315.

Pluckthun, A. (1992). "Mono- and Bivalent Antibody Fragments Produced in *Escherichia coli*: Engineering, Folding and Antigen Binding," *Immunological Reviews* No. 130:151-189.

Pranzatelli, M.R. et al. (Mar. 2003). "CSF B-Cell Over-Expansion in Paraneoplastic Opsocionus-Myoclonus: Effect of Rituximab, an Anti-B-Cell Monoclonal Antibody," 55th Annual Meeting, Mar. 29-Apr. 5, 2003, Honolulu, Haw aii, *Neurology* 60(Suppl. 1) PO5.128:A395, one page.

Press, O.W. et al. (Feb. 1987). "Monoclonal Antibody 1F5 (Anti-Cd20) Serotherapy of Human B Cell Lymphomas," *Blood* 69(2):584-591.

Presta, L.G. (1992). "Antibody Engineering," *Current Opinion in Structural Biology* 2:593-596.

Presta, L.G. et al. (Sep. 1, 1993). "Humanization of an Antibody Directed Against , IgE," *The Journal of Immunology* 151(5):2623-2632.

(56) References Cited

OTHER PUBLICATIONS

Presta, L.G. et al. (Oct. 15, 1997). "Humanization of an Anti-Vacualar Endothelial Growth Factor Monoclonal Antibody for the Therapy of Solid Tumors and Other Disorders," *Cancer Res.* 57:4593-4599.
Ratanatharathorn, V. et al. (Aug. 15, 2000)."Anti-CD20 Chimeric Monoclonal Antibody Treatment of Refractory Immune-Mediated Thrombocytopenia in a Patient With Chronic Graft-Versus-Host Disease," *Ann. Int. Med.* 133(4):275-279.
Reyes, G.R. et al. (Jun. 17, 1982). "Expression of Human β-Interferon cDNA Under the Control of a Thymidine Kinase Promoter from Herpes Simplex Virus," *Nature* 297:598-601.
Riechmann, L. et al. (Mar. 24, 1988), "Reshaping Human Antibodies for Therapy," *Nature* 332:323-327.
Robak, T. et al. (2001). "Correspondence: Pure Red Cell Aplasia in Patients With Chronic Lymphocyte Leukameria Treated With Cladribine," *Br. J. Haematol.* 112:1083-1090.
Ronsein, G.E. et al. (2009). "Character of $O_2$ ('Δ)-Derived Oxidation Products Tryptophan: A Combination of Tandem Mass Spectrometry Analyses and Isotopic Labeling Studies," *J American Society for Mass Spectrometry* 20:188-197.
Saleh, M.N. et al. (2000). "A Riot Study of the Anti-CD20 Monoclonal Antibody Rituximab in Patients With Refractory Immune Thrombocytopenia," *Semin. Oncol.* 27(Supp 12):99-103.
Sastry, L. et al. (Aug. 1989). "Cloning of the Immunological Repertoire in *Escherichia coli* for Generation of Monoclonal Catalytic Antibodies: Construction of a Heavy Chain Variable Region-Specific cDNA Lbrary," *Proc. Natl. Acad. Sci. USA* 86: 5728-5732.
Seefeldt, M.B et al. (Oct. 2004). "High-Pressure Refolding of Bikunin: Efficacy and Thermodynamics," *Protein Science* 10:2639-2650.
Shalaby, M.R. et al. (Jan. 1, 1992). "Development of Humanized Bispecific Antibodies Reactive with Cytotoxic Lymphocytes and Tumor Cells Overexpressing the *HER2* Protooncogene," *J. Exp. Med.* 175:217-225.
Sheriff, S. et al. (Sep. 1996). "Redefining the Minimal Antigen-Binding Fragment," *Nature Structural Biology* 3(9):733-736.
Shinkawa, T. et al. (Jan. 31, 2003). "The Absence of Fucose But Not the Presence Galactose or Bisecting N-Acetytglucosamine of Human IgG1 Complex-Type Oligosaccharides Shows the Critical Role of Enhancing Antibody-Dependent Cellular Cytotoxicity," *J. Bio. Chem.* 278(5):3466-3473.
Shopes, B. (May 1, 1992). "A Genetically Engineered Human IgG Mutant With Enhanced Cytolytic Activity," *J. Immunol.* 148:2918-2922.
Shrake, A. et al. (Sep. 1973). "Environment and Exposure to Solvent of Protein Atoms. Lysozyme and Insulin," *J. Mol. Biol.* 79(2):351-371.
Sidhu, S.S. et al. (2004). "Phage-displayed Antibody Libraries of Synthetic Heavy Chain Complementarity Determining Regions," *J. Mol. Biol.* 338:299-310.
Sims, M.J. et al. (Aug. 15, 1993). "A Humanized CD18 Antibody Can Block Function w ithout Cell Destruction," *The Journal of Immunology* 151(4):2296-2308.
Singh, S. et al. (2003). "Effect of Polyols on the Conformational Stability and Biological Activity of a Model Protein Lysozyme," *AAPS Pharm. Sci. Tech.* 4:1-9.
Skerra, A. (1993). "Bacterial Expression of Immunoglobulin Fragments," Current Opinion in Immunology 5:256-262.
Somer, B. G. et al. (Jun. 15, 2003). "Improvement in Sjögren's Syndrome follow ing therapy w ith Rituximab for marginal zone lymphoma," Arthritis and Rheumatism 49(3):394-398.
Specks, U. et al. (Dec. 2001). "Response of Wegener's Granulomatosis to Anti-CD20 Chimeric Monoclonal Antibody Therapy," *Arthritis & Rheumatism* 44(12):2836-2840.
Stahl, H.D. et al. (2003). "Rituximab in RA: Efficacy and Safety From a Randomised, Controlled Trial," *Ann. Rheum. Dis.* 62 (Suppl. 1):OP004.

Stasi, R. et al. (2001). "Rituximab Chimeric Anti-CD20 Monoclonal Antibody Treatment for Adults With Chronic Idiopathic Thrombocytopenic Purpura," *Blood* 98:952-957.
Stevenson, G.T. et al. (1989). "A Chimeric Antibody With Dual Fc Regions (bisFabFc) Prepared by Manipulations of the Igg Hinge," *Anti-Cancer Drug Design* 3:219-230.
Stinchcomb, D.T. et al. (Nov. 1, 1979). "Isolation and Characterisation of a Yeast Chromosomal Replicator," *Nature* 282:39-43.
Stroop, S.D. et al. (Dec. 2011 e-pub. Jul. 24, 2011). "Photosensitizers Form in Histidine Buffer and Mediate the Photodegradation of a Monoclonal Antibody," *J Pharm Sci.* pp. 5142-5155.
Suresh, M.R. et al. (1986). "Production of Hybridomas," *Methods in Enzymology* 121:210-228.
Szjetli, J. (2004). "Past; Present, and Future Cyclodextrin Research," *Pure Appl. Chem.* 76(10):1825-1845.
Tedder, T.F. et al. (Aug. 1985). "The B Cell Surface Molecule B1 Is Functionally Linked With B Cell Activation and Differentiation," *J. Immunol.* 135(2):973-979.
Tedder T.F. et al. (1990). "The CD20 Surface Molecute of B Lymphocytes Functions as a Calcium Channel," *J. Cell. Biochem.* 14D:195.
Thurow, H. et al. (Aug. 1984). "Stabilisation of Dissolved Proteins against Denaturation at Hydrophobic Interfaces," *Diabetologia* 27(2):212-218.
Todorovski, T. et al. (Oct. 2011). "Mass Spectrometric Characterization of Peptides Containing Different Oxidized Tryptophan Residues," *Journal of Mass Spectrometry* 46(10):1030-1038.
Tomlinson, I.M. et al. (1992). The Repertoire of Human Germ $V_H$ Sequences Reveals about Fifty Groups of $V_H$ Segments w ith Different Hypervariable Loops, *J. Mol. Biol.* 227: 776-798.
Torosantucci, R. et al. (Mar. 2014 e-pub. Sep. 25, 2013). "Oxidation of Therapeutic Proteins and Peptides: Structural and Biological Consequences," *Pharmaceutical Research* 31(3):541-553.
Traunecker, A. et al. (1991). "Bispecific Single Chain Molecules (Janusins) Target Cytotoxic Lymphocytes on HIV Infected Cells," *The EMBO Journal* 10(12):3655-3659.
Tutt, A. et al. (Jul. 1, 1991). "Trispecific F(ab')$_3$ Derivatives that use Cooperative Signaling via the Tcr/Cd3 Complex and Cd2 to Activate and Redirect Resting Cytotoxic T Cells," *The Journal of Immunology.* 147(1): 60-69.
Uekama, K. et al. (1998). "Cyclodextrin Drug Carrier Systems," *Chem. Rev.* 98:2045-2076.
Urlaub, G. et al. (Jul. 1980). "Isolation of Chinese Hamster Cell Mutants Deficient in Dinydrofolate Reductase Activity," *Proc. Natl. Acad. Sci. USA* 77(7)4216-4220.
Valentine, M.A. et al. (1987). "Structure and Function of the B-Cell Specific 35-37 kDa CD20," in *Leukocyte Typing III.* McMichael, Ed., Oxford University Press, pp. 440-443.
Valentine, M.A. et al. (Jul. 5, 1989). "Phosphorylation of the CD20 Phosphoprotein in Resting B Lymphocytes. Regulation by Protein Kinase C," *J. Biol. Chem.* 264(19):11282-11287.
Van Besien, K. et al. (2000). "Clinical Manifestations, Staging and Treatment of Non-Hodgkin's Lymphoma," Chap. 70, in *Hematology, Basic Principles and Practice,* 3rd ed. Hoffman et al. (editors). Churchill Livingstone, Philadelphia, pp. 1293-1338.
Van Den Berg, J.A. et al. (Feb. 1990). "*Kluyveromyces* as a Host for Heterologous Gene Expression: Expression and Secretion of Prochymosin," *Bio/Technology* 8:135-139.
Van Duk, M.A. et al. (2001). "Human Antibodies as Next Generation Therapeutics," *Current Opinion in Chemical Biology* 5:368-374.
Vaswani, S.K. et al. (Aug. 1998). "Humanized Antibodies as Potential Therapeutic Dugs," *Annals of Allergy, Asthma, & Immunology* 81:105-115.
Verhoeyen, M. et al. (Oct. 23, 1987). "Reshaping Huamn Antiobodies: Grafting Antilysozyme Activity," *Science* 239:1534-1536.
Vollmers H.P. et al. (2005). "Death by Stress: Natural IgM-Induced Apoptosis," *Methods and Findings in Experimental and Clinical Pharmacology* 27(3):185-191.
Vollmers, H.P. et al. (2005). "The "Early Birds": Nature IgM Antibodies and Immune Surveillance," *Histol Histopathol* 20:927-937.

(56) References Cited

OTHER PUBLICATIONS

Wang, W. (Jan. 31, 2005 pub. Jan. 6, 2005). "Protein Aggregation and its Inhibition Biopharmaceutics," *International Journal of Pharmaceutics* 289(1-2)1-30.
Wang, W. et al. (Mar. 2011 e-pub. Jan. 21, 2011). "Impact of Methionine Oxidation in Human IgG1 Fc on Serum Half-Life of Monoclonal Antibodies," *Molecular Immunology* 48(6-7):860-866.
Ward, E.S. et al. (Oct. 12,1989). "Binding Activities of a Repertoire of Single Immunoglobulin Variable Domains Secreted from *Escherichia coli*" *Nature* 341:544-546.
Waterhouse, P. et al. (Mar. 1993). "Combinatorial Infection and In Vivo Recombination: A Strategy for Making Large Phage Antibody Repertoires," *Nucleic Acids Research* 21(9):2265-2266.
Webb, S. et al. (Feb. 2002). "A New Mechanism for Decreasing Aggregation of Recombinant Human Interferon-γ by a Surfactant: Slow ed Dissolution of Lyophilized Formulations in a Solution Containing 0.03% Polysorbate 20," *Journal of Pharmaceutical Sciences* 91(2):543-558.
Williams, S.C. et al. (1993), "Cloning and Sequencing of Human Immunoglobulin $V_\lambda$ Gene Segments," *Eur. J. Immunol.* 23:1456-1461.
Winter, G. et al., (1994). "Making Antibodies by Phage Display Technology," *Ann. Rev. Immunol.* 12:433-455.
Wolff, E.A. et al. (Jun. 1, 1993). "Monoclonal Antibody Homodimers: Enhanced Antitumor Activity in Nude Mice," *Cancer Research* 53:2560-2565.
Wylam, M.E. et al. (2003), "Successful Treatment of Refractory Myasthenia Gravis Using Rituximab: A Pediatric Case Report," *J. Pediatr*, 143:674-677.
Xu, J.L. et al. (Jul. 2000). "Diversity in the CDR3 Region of $V_H$ is Sufficient for Antibody Specificities," *Immunity* 13:37-45.
Yaniv, M. (May 6, 1982). "Enhancing Elements for Activation of Eukaryotic Promoters," *Nature* 297:17-18.
Yazaki, P.J. et al. (2003). "Expression of Recombinant Antibodies in Mammalian Cell Lines," *Methods in Molecular Biology* 248:255-268.
Zaja, F. et al. (2000). "Rituximab for Myasthenia Gravis Developing After Bone Marrow Transplant," *Neurology* 55:1062-1063.
Zaja, F. et al. (Feb. 2002). "B-cell Depletion With Rituximab as Treatment for Immune Hemolytic Anemia and Chronic Thrombocytopenia," *Haematologica* 87(2)189-195.
Zaja, F. et al. (Mar. 2002), "ATP Downregulation in Mononuclear Cells From Children With Graft-Verus-Host Disease Following Extracorporeal Photochemotherapy," *Haematologica* 87(3):335-336.
Zaja, F. et al. (May 15, 2003, e-pub. Jan. 20, 2003). "Efficacy and Safety of Rituximab in Type II Mixed Cryoglobulinemia," *Blood* 101(10):3827-3834.
Zapata, G. et al. (1995). "Engineering Linear F(ab')2 Fragments for Efficient Production in *Escherichia coli* and Enhanced Antiproliferative Activity," *Protein Engineering* 8(10):1057-1062.
Zhu, Z. et al. (1997). "Remodeling Domain Interfaces to Enhance Heterodimer Formation," *Protein Science* 6;781-788.
International Search Report dated Apr. 4, 2017, for PCT Application No. PCT/US2016/069046, filed on Dec. 28, 2016. 4 pages.
Written Opinion dated Apr. 4, 2017, for PCT Application No. PCT/US2016/069046, filed on Dec. 28, 2016, 5 pages.
Serno, T. et al. "Inhibition of Agitation-Induced Aggregation of an IgG-antibody by Hydroxypropyl-β-Cyclodextrin," *J. Pharm. Sci.* 99(3):1193-1206, (Mar. 2010. E-pub. Sep. 22, 2009).
Serno, T. et al. "The Role of Polysorbate 80 and HPβCDat the Air-Water Interface of IgG Solutions," *Pharm. Res.* 30:117-130, (2013, e-pub. Aug. 22, 2012).
International Preliminary Report on Patentability dated Jul. 3, 2018, for PCT Application No. PCT/US2016/069046, filed on Dec. 28, 2016, 6 pages.

\* cited by examiner

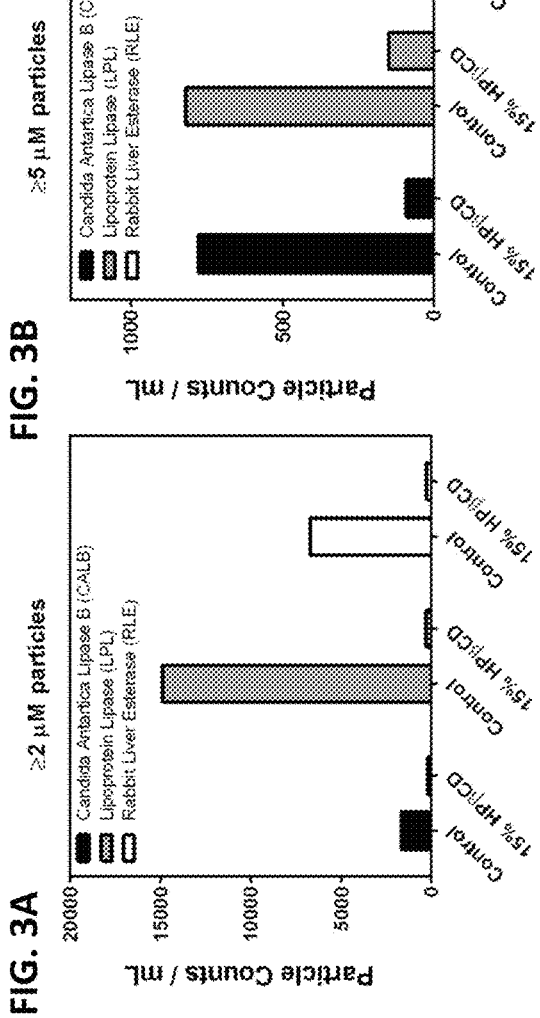
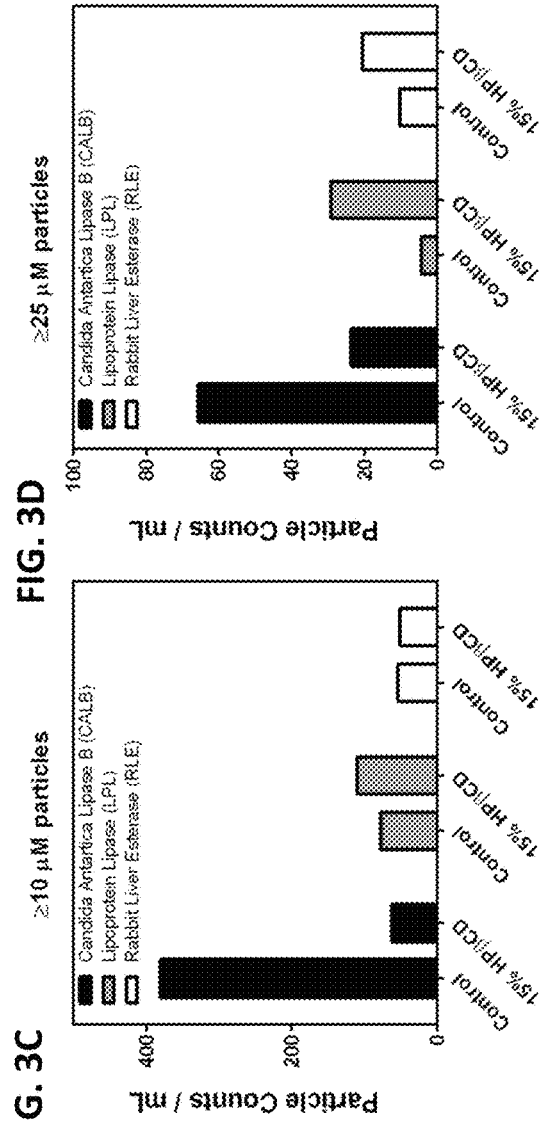
FIG. 3A
FIG. 3B
FIG. 3C
FIG. 3D

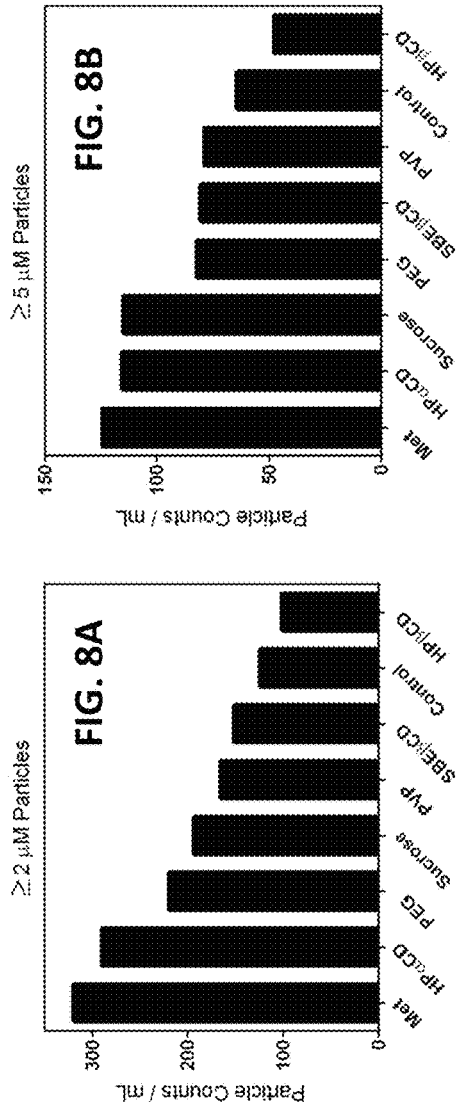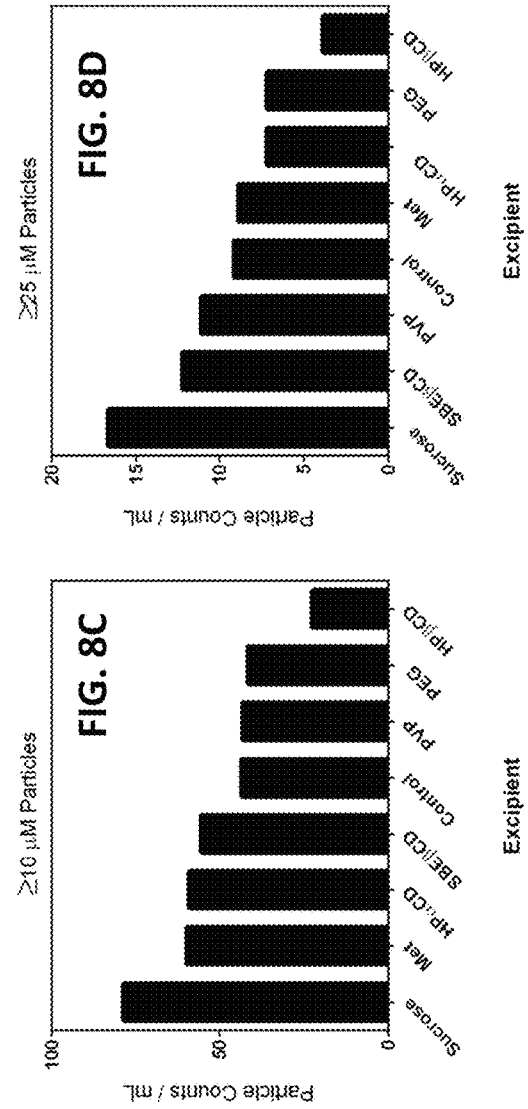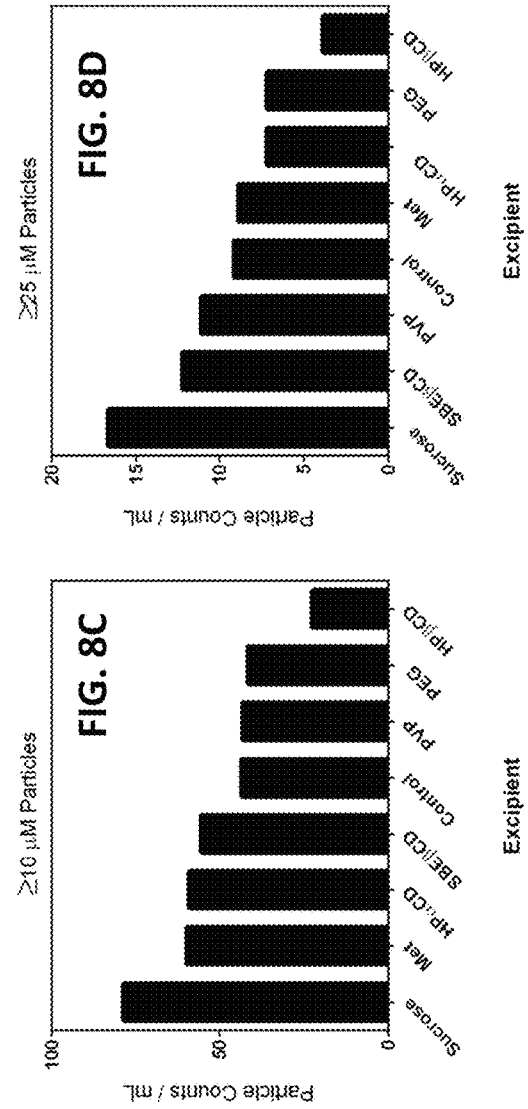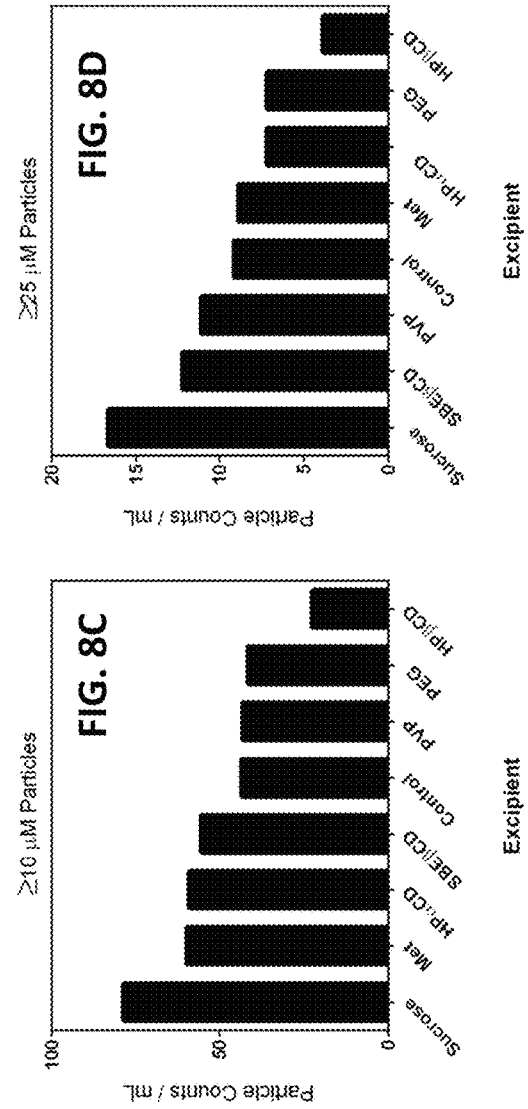

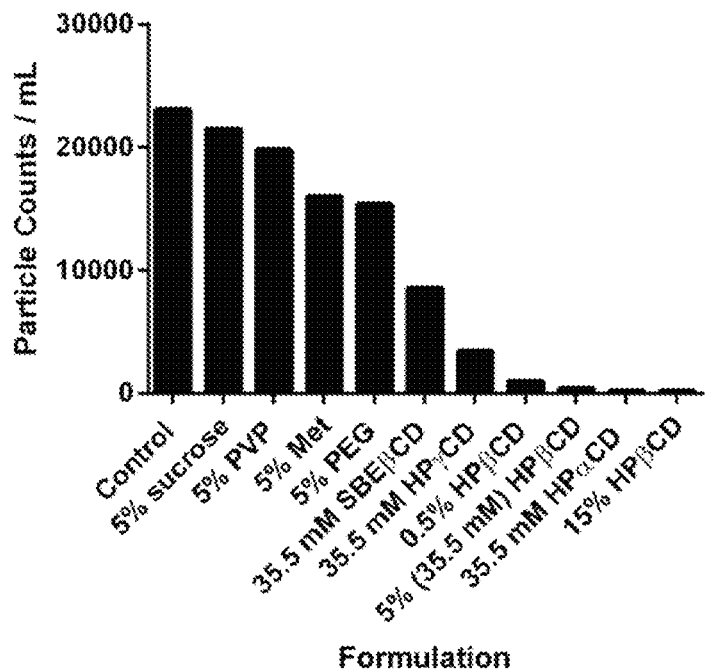
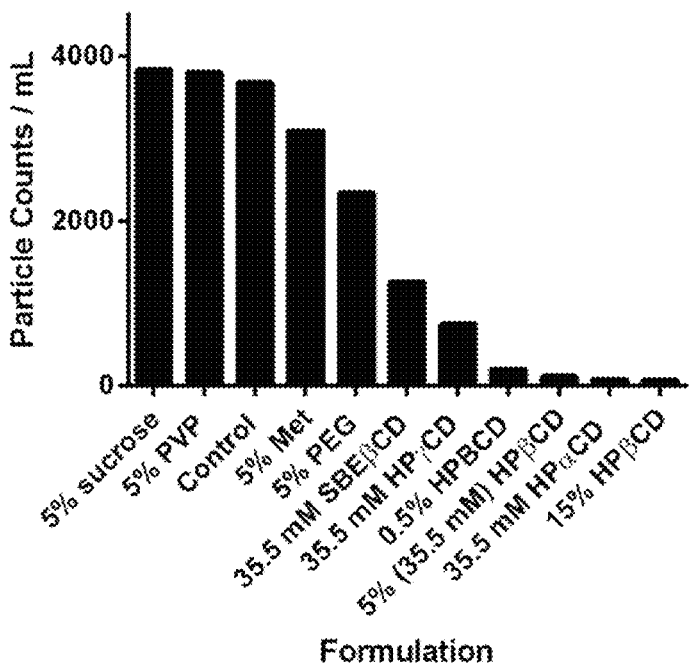

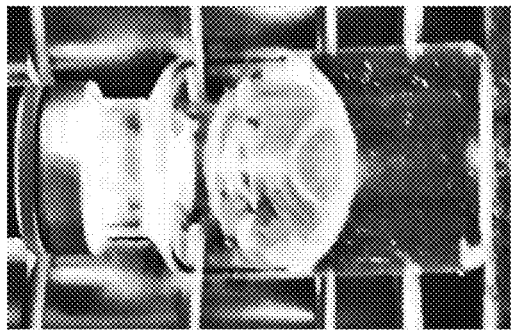 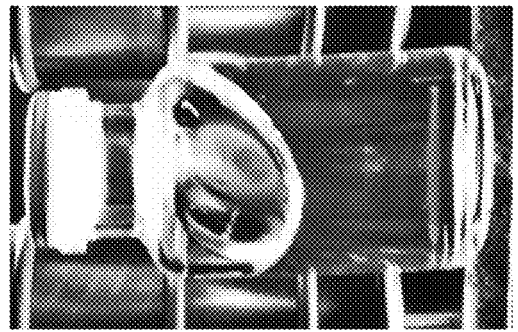
FIG. 11A
FIG. 11B

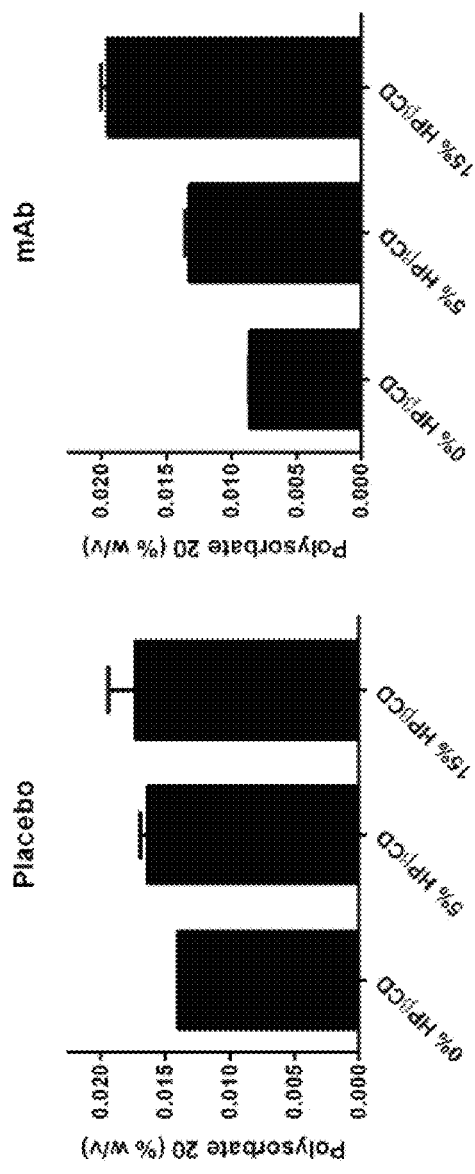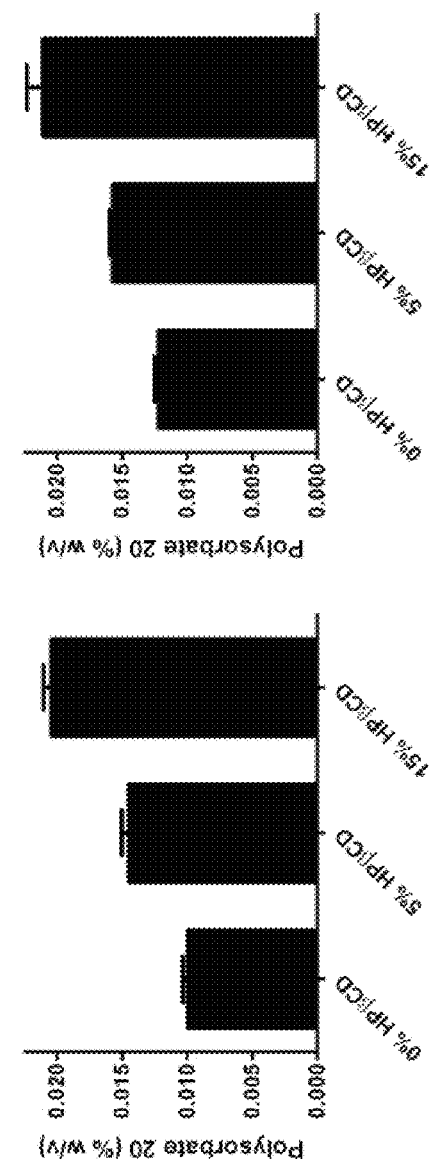

FORMULATIONS WITH REDUCED DEGRADATION OF POLYSORBATE

CROSS-REFERENCE TO RELATED APPLICATIONS

This application claims the benefit of U.S. Provisional Application No. 62/272,965, filed Dec. 30, 2015, the contents of which are hereby incorporated by reference in its entirety.

FIELD OF THE INVENTION

This invention relates to aqueous pharmaceutical formulations comprising a cyclodextrin and a polysorbate and methods for reducing polysorbate degradation and for disaggregating and solubilizing polysorbate degradation products.

BACKGROUND OF THE INVENTION

Pharmaceutical formulations commonly contain polysorbates 20 and 80 (PS20 and PS80), non-ionic surfactants composed of a hydrophilic polyoxyethylene head group and a hydrophobic fatty acid tail. The addition of surfactants to formulations protects proteins from surface-induced denaturation and aggregation (Geisen, *Diabetologia* 27:212-218 (1984); Wang, *Int. J. Pharm.* 289:1-30 (2005)). Protein aggregation can occur during drug substance (DS) and drug product (DP) processing, long-term storage, shipment, and during administration (Cromwell et al., *AAPS J.* 8:E572-E579 (2006)). It has been shown that the addition of a surfactant (e.g., PS20) can minimize interfacial interactions that may stress proteins during filtration (Maa et al., *J. Pharm. Sci.* 87:808-812 (1998); Maa et al., *Biotechnol. Bioeng.* 50:319-328 (1996)), agitation (Liu et al., *J. Pharm. Sci.* 102:2460-2470 (2013)), freeze-thaw (Kreilgaard et al., *J. Pharm. Sci.* 87:1597-1603 (1998); Hillgren et al., *Int. J. Pharm.* 237:57-69 (2002)), lyophilization (Carpenter, *Protein Sci.* 13:54-54 (2004); Carpenter et al., *Pharm. Res.* 14:969-975 (1997)), reconstitution (Webb et al., *J. Pharm. Sci.* 91:543-558 (2002)), administration (Kumru et al., *J. Pharm. Sci.* 101:3636-3650 (2012)), and storage.

To ensure stabilization of active pharmaceutical ingredients (API) during processing, long-term storage, and during administration, it is important to prevent polysorbate degradation. However, PS20 is susceptible to degradation via hydrolytic and oxidative pathways (Kumru, et al., *J. Pharm. Sci.* 101:3636-3650 (2012); Mahler et al., *Abstr Pap Am Chem S.* 239: (2010)).

Oxidative degradation of polysorbates has been well characterized and has been studied extensively (Kerwin, *J. Pharm. Sci.* 97:2924-2935 (2008); Kishore et al., *J. Pharm. Sci.* 100:721-731 (2011)). Oxidation typically occurs in the context of two mechanisms (1) the autoxidation of the ethylene oxide group and (2) radical oxidation at the site of unsaturation (Kishore et al., *J. Pharm. Sci.* 100:721-731 (2011)). Although oxidative degradation of polysorbates has been observed, it has been shown that PS20 oxidation can be mitigated in protein formulations by coformulating with antioxidants (e.g., methionine). Formulations containing tryptophan have also been developed to prevent oxidation of amino acid residues (US2014/0322203; US2014/0314) Oxidative and hydrolytic polysorbate degradation pathways are distinguishable by unique degradation product profiles. Hydrolytic polysorbate degradation produces predominantly fatty acids and oxidative polysorbate degradation produces more diverse degradation products including peroxides, aldehydes, acids, keytones, n-alkanes, fatty acid esters, and other degradation products (Ravuri et al., *Pharm. Res.* 28:1194-1210 (2011)).

Stress models for oxidative polysorbate degradation using 2,2'-Azobisisobutyramidinium (AAPH) that degrade PS20 have been described previously (Borisov et al., J. Pharm. Sci. 104:1005-1018 (2015)). Using similar approaches, representative stress models can be used to develop formulations that reduce oxidative polysorbate degradation under relevant conditions.

Stress models for hydrolysis using purified esterases (e.g., Porcine Liver Esterase, etc.) and lipases (e.g., tweenase, etc.) have been described previously (Labrenz, *J. Pharm. Sci.* 103L2268-2277 (2014)). Using similar approaches, representative stress models can be used to develop formulations that reduce catalytic polysorbate degradation under relevant conditions.

Recently, there have been reports of enzymatic degradation of polysorbate in monoclonal antibody (mAb) formulations. For example, Labrenz attributed polysorbate 80 (PS80) degradation observed in CHO-derived mAb formulations to specific enzymatic mechanism rather than a general biologic hydrolysis mechanism based on the PS20 degradation profile (Labrenz et al., *J. Pharm. Sci.* 103:2268-2277 (2014)). Sequencing of the CHO cell genome has identified various host cell proteins (HCPs) (e.g., lipases) capable of degrading polysorbate (S. Hammond et al., *Biotech. Bioeng.* 109:1353-1356 (2012)). Subsequently, Lee et al. have shown that reducing the expression of specific HCPs substantially reduced the hydrolysis of PS80 relative to control samples. These recent findings establish that lipases associated with biologics manufacturing are expressed in upstream processes. Downstream purification processes (e.g., Protein A) are capable of removal of HCPs; however, it has been shown that some HCPs can be co-purified with API molecules that have similar properties and are thus retained in trace quantities in the drug substance and drug product (K. Lee, et al., A Chinese Hamster Ovary Cell Host Cell Protein That Impacts PS-80 Degradation. AccBio Conference (2015). Presumably, lipases with high activity can result in significant polysorbate degradation even at undetectable levels. There are numerous ongoing efforts to identify and remove lipases from protein drugs by engineering cells with reduced lipase expression and via downstream processing steps (e.g., chromatography). However, the enzymatic degradation of PS20 and PS80 remains a significant challenge in biopharmaceutical development and there have been no significant efforts reported to identify optimal formulations for reducing hydrolytic or catalytic PS20 degradation.

Polysorbate degradation has numerous consequences that may impact the stability and shelf-life of protein drug formulations. Polysorbate degradants include poorly soluble fatty acids that may result in the formation of visible and subvisible particles in the solution. The loss of PS20 may also reduce the protective effects of PS20 for protein formulations. Additionally, a spiking study demonstrated that some of the PS20-related degradants can impact stability of protein drugs; however, no impact was observed under pharmaceutically relevant conditions (Kishore et al., *Pharm. Res.* 28:1194-1210 (2011).

What is needed is a method of reducing polysorbate degradation so that the protective effects of polysorbate on formulations (e.g., polypeptides) are maintained over time. This will result in more stable polypeptide formulations during processing, long-term storage, and during administration which in turn will lengthen the shelf life of polypeptide formulations and reduce waste caused by degraded and expired formulations.

All references cited herein, including patent applications and publications, are incorporated by reference in their entirety.

SUMMARY

The invention provides a method of reducing polysorbate degradation in an aqueous formulation comprising a polysorbate, the method comprising adding a cyclodextrin to the formulation, wherein the resulting w/w ratio of cyclodextrin to polysorbate is greater than about 37.5:1. In some aspects, the invention provides a method of reducing polysorbate degradation in an aqueous formulation comprising a polysorbate, the method comprising adding a cyclodextrin to the formulation wherein the resulting w/w ratio of cyclodextrin to polysorbate is greater than about 37.5:1, wherein the formulation comprises about 0.005%-0.4% polysorbate. In some aspects, the invention provides a method of reducing polysorbate degradation in an aqueous formulation comprising a polysorbate, the method comprising adding a cyclodextrin to the formulation to a concentration of about 0.01%-30%, wherein the resulting w/w ratio of cyclodextrin to polysorbate is greater than about 37.5:1, wherein the formulation comprises about 0.005%-0.4% polysorbate. In some aspects, the invention provides a method of reducing the amount of sub-visible and visible particles in an aqueous formulation comprising polysorbate, comprising adding a cyclodextrin to the formulation, wherein the resulting w/w ratio of cyclodextrin to polysorbate is greater than about 37.5:1, wherein the formulation comprises polysorbate and a polypeptide. In some aspects the invention provides a method to disaggregate and solubilize polysorbate degradation products in an aqueous formulation comprising adding a cyclodextrin to the formulation, wherein the resulting w/w ratio of cyclodextrin to polysorbate is greater than about 37.5:1, wherein the formulation comprises polysorbate and a polypeptide.

In some embodiments of the above aspects, the polysorbate is polysorbate 20 or polysorbate 80. In some embodiments, the cyclodextrin is HP-βcyclodextrin, HP-γcyclodextrin, or sulfobutyl ether β-cyclodextrin. In some embodiments, the concentration of polysorbate in the formulation is in the range of about 0.01% to 0.4%. In some embodiments, the concentration of polysorbate in the formulation is in the range of about 0.01% to 0.1%. In some embodiments, the concentration of polysorbate in the formulation is about 0.02%. In some embodiments, the concentration of cyclodextrin in the formulation is in the range of about 0.5-30%. In some embodiments, the concentration of cyclodextrin in the formulation is about 15%.

In some embodiments of the above aspects and embodiments, the polysorbate degradation is reduced by about 50%, about 75%, about 80%, about 85%, about 90%, about 95% or about 99%. In some embodiments, less than about 1,000, about 750, about 500, about 250, about 150, about 100, about 50, or about 25 polysorbate particles greater than about 2 microns in diameter/mL are formed.

In some embodiments of the above aspects and embodiments, the formulation comprises a polypeptide. In some embodiments, the polypeptide is an antibody. In some embodiments, the antibody is a polyclonal antibody, a monoclonal antibody, a humanized antibody, a human antibody, a chimeric antibody, a multispecific antibody or antibody fragment. In some embodiments, the polypeptide concentration in the formulation is about 1 mg/mL to about 250 mg/mL.

In some embodiments of the above aspects and embodiments, the formulation is stable at about 2° C. to about 8° C. for at least about six months, at least about 12 months, at least about 18 months, or at least about 24 months. In some embodiments, the formulation is stable at about 1° C. to about 10° C. for at least about forty-eight months. In some embodiments, the formulation is stable at about 2° C. to about 8° C. for at least about forty-eight months.

In some embodiments, the formulation has a pH of about 4.5 to about 7.0. In some embodiments, the formulation has a pH of about 4.5 to about 6.0. In some embodiments, the formulation has a pH of about 6.0.

In some embodiments of the above aspects and embodiments, the formulation further comprises one or more excipients selected from the group consisting of a stabilizer, a buffer, a surfactant, and a tonicity agent. In some embodiments, the formulation is a pharmaceutical formulation suitable for administration to a subject. In some embodiments, the formulation is pharmaceutical formulation suitable for intravenous, subcutaneous, intramuscular, or intravitreal administration to a subject.

In some aspects, the invention provides an aqueous formulation comprising a polypeptide, a polysorbate and a cyclodextrin, wherein the formulation has been stored at about 1° C. to about 10° C. for at least about six months, wherein the initial w/w ratio of cyclodextrin to polysorbate in the formulation is at least about 37.5:1 and wherein the amount of polysorbate in the formulation is at least about 80% of the initial amount of polysorbate in the formulation. In some aspects, the invention provides an aqueous formulation comprising a polypeptide, a polysorbate and a cyclodextrin, wherein the formulation has been stored at about 1° C. to about 10° C. for at least about six months, wherein the w/w ratio of cyclodextrin to polysorbate in the formulation is at least about 37.5:1 and wherein less than about 1% of the polysorbate has degraded.

In some embodiments of the above aspects, the cyclodextrin is HP-βcyclodextrin, HP-γcyclodextrin, or sulfobutyl ether β-cyclodextrin. In some embodiments, the concentration of polysorbate in the formulation is in the range of about 0.01% to 0.4%. In some embodiments, the concentration of polysorbate in the formulation is in the range of about 0.01% to 0.1%. In some embodiments, the concentration of polysorbate in the formulation is about 0.02%. In some embodiments, the concentration of cyclodextrin in the formulation is in the range of about 0.5-30%. In some embodiments, the concentration of cyclodextrin in the formulation is about 15%.

In some embodiments of the above aspects and embodiments, the polysorbate degradation is reduced by about 50%, about 75%, about 80%, about 85%, about 90%, about 95% or about 99%. In some embodiments, less than about 1,000, about 750, about 500, about 250, about 150, about 100, about 50, or about 25 polysorbate particles greater than about 2 microns in diameter/mL are formed.

In some embodiments of the above aspects and embodiments, the formulation is stable at about 2° C. to about 8° C. for at least about six months. In some embodiments, the formulation is stable at about 1° C. to about 10° C. for at least about forty-eight months. In some embodiments, the formulation is stable at about 2° C. to about 8° C. for at least about forty-eight months.

In some embodiments of the above aspects and embodiments, the formulation further comprises a polypeptide. In some embodiments, the polypeptide is an antibody. In some embodiments, the antibody is a polyclonal antibody, a monoclonal antibody, a humanized antibody, a human antibody, a chimeric antibody, a multispecific antibody or antibody fragment, the polypeptide concentration in the formulation is about 1 mg/mL to about 250 mg/mL.

In some embodiments of the above aspects and embodiments, the formulation has a pH of about 4.5 to about 7.0. In some embodiments, the formulation has a pH of about 4.5 to about 6.0. In some embodiments, the formulation has a pH of about 6.0.

In some embodiments of the above aspects and embodiments, the formulation further comprises one or more excipients selected from the group consisting of a stabilizer, a buffer, a surfactant, and a tonicity agent. In some embodiments, the formulation is a pharmaceutical formulation suitable for administration to a subject. In some embodiments, the formulation is pharmaceutical formulation suitable for intravenous, subcutaneous, intramuscular, or intravitreal administration to a subject.

BRIEF DESCRIPTION OF THE DRAWINGS

FIGS. 3A-3D display the average (n=3) ≥2 µM (FIG. 3A), ≥5 µM (FIG. 3B), ≥10 µM (FIG. 3C), and ≥25 µM (FIG. 3D) particle counts per milliliter determined by HIAC for samples digested using *Candida Antarctica* Lipase B (black), Lipoprotein Lipase (grey), and Rabbit Liver Esterase (white) enzymes in protein-free samples containing 0.02% (w/v) PS20 with 0 and 15% (w/v) HP-β-CD.

FIGS. 8A-8D display the average (n=3) ≥2 µM (FIG. 8A), ≥5 µM (FIG. 8B), ≥10 µM (FIG. 8C), and ≥25 µM (FIG. 8D) particle counts per milliliter determined by HIAC for samples digested using 15 µg/mL of PPL enzyme for 4.5 hours at room temperature in protein-free samples containing 0.02% (w/v) PS20 with no excipient (control), 15% (w/v) sucrose, 1% (w/v) methionine, 15% (w/v) PEG 1500, 15% (w/v) PVP, 15% (w/v) HP-α-CD, 15% (w/v) HP-β-CD, 15% (w/v) SBE-β-CD, and 15% (w/v) HP-γ-CD.

FIGS. 10A and 10B display the average (n=3) (FIG. 10A) ≥2 µM, and (FIG. 10B) ≥5 µM particle counts per milliliter determined by HIAC for samples after addition of various excipients (HP-α-CD, HP-β-CD, HP-γ-CD, SBE-β-CD, PVP, PEG 1500, sucrose, and methionine) to evaluate the re-solubilization of existing particles produced as a result of enzymatic PS-20 degradation.

FIGS. 11A and 11B display a vial containing PS20-related particles generated by enzymatic digestion using 15 µg/mL of PPL enzyme for 4.5 hours at room temperature (FIG. 11A) before, and (FIG. 11B) after spiking in 15.0% (w/v) HP-β-CD. Following addition of 15% (w/v) HP-β-CD, there are no visible particles.

FIGS. 17A-17D display the relative percent of PS20 determined by RP-ELSD for (FIG. 17A) Control, (FIG. 17B) monoclonal antibody (mAb), (FIG. 17C) bispecific antibody (BsAb), and (FIG. 17D) single Fab antibody (sFAb) samples digested using 15 µg/mL of PPL enzyme for 4.5 hours at room temperature containing 0, 5, and 15% (w/v) HP-β-CD.

DETAILED DESCRIPTION

Figure 1:
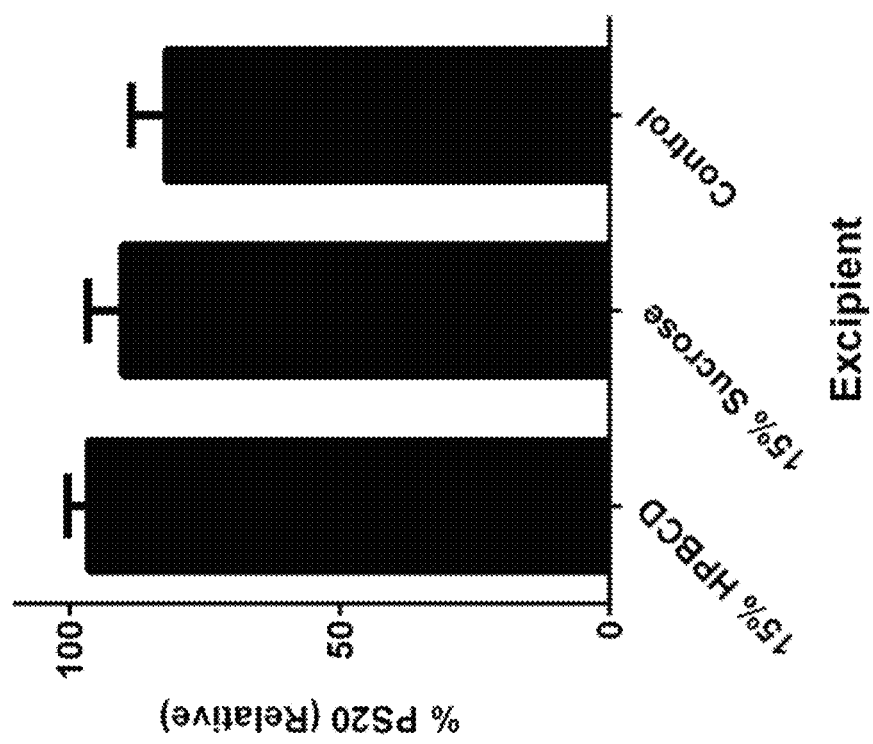
FIG. 1 displays the average (n=3) relative percent of PS20 determined by RP-ELSD for samples oxidized with 5 mM AAPH at 40° C. for 24 hours containing no excipient (control), 15% (w/v) sucrose, and 15% (w/v) HP-β-CD.

The invention herein relates to methods of reducing polysorbate degradation in an aqueous formulation comprising a polysorbate by adding a cyclodextrin to the formulation, wherein the resulting w/w ratio of cyclodextrin to polysorbate is greater than about 37.5:1. The invention also provides methods of reducing the amount of sub-visible and visible particles in an aqueous solution and methods of disaggregating and solubilizing polysorbate degradation products comprising polysorbate comprising adding cyclodextrin to a solution wherein the ratio of cyclodextrin to polysorbate is greater than about 37.5:1. The invention further provides stable aqueous formulations comprising a polysorbate, and a cyclodextrin, wherein the w/w ratio of cyclodextrin to polysorbate in the formulation is at least about 37.5:1. In some embodiments, the formulation further comprises a polypeptide.

I. Definitions

The term "pharmaceutical formulation" refers to a preparation which is in such form as to permit the biological activity of the active ingredient to be effective, and which contains no additional components which are unacceptably toxic to a subject to which the formulation would be administered. Such formulations are sterile.

A "sterile" formulation is aseptic or free or essentially free from all living microorganisms and their spores.

A "stable" formulation is one in which the protein therein essentially retains its physical stability and/or chemical stability and/or biological activity upon storage. Preferably, the formulation essentially retains its physical and chemical stability, as well as its biological activity upon storage. A stable formulation also may retain its level of polysorbate upon storage. The storage period is generally selected based on the intended shelf-life of the formulation. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, *Adv. Drug Delivery Rev.* 10: 29-90 (1993), for example. Stability can be measured at a selected amount of light exposure and/or temperature for a selected time period. Stability can be evaluated qualitatively and/or quantitatively in a variety of different ways, including evaluation of aggregate formation (for example using size exclusion chromatography, by measuring turbidity, and/or by visual inspection); evaluation of ROS formation (for example by using a light stress assay or a 2,2'-Azobis(2-Amidinopropane) Dihydrochloride (AAPH) stress assay); oxidation of specific amino acid residues of the protein (for example a Trp residue and/or a Met residue of a monoclonal antibody); by assessing charge heterogeneity using cation exchange chromatography, image capillary isoelectric focusing (icIEF) or capillary zone electrophoresis; amino-terminal or carboxy-terminal sequence analysis; mass spectrometric analysis; SDS-PAGE analysis to compare reduced and intact antibody; peptide map (for example tryptic or LYS-C) analysis; evaluating biological activity or target binding function of the protein (e.g., antigen binding function of an antibody); etc. Instability may involve any one or more of: aggregation, deamidation (e.g. Asn deamidation), oxidation (e.g. Met oxidation and/or Trp oxidation), isomerization (e.g. Asp isomeriation), clipping/hydrolysis/fragmentation (e.g. hinge region fragmentation), succinimide formation, unpaired cysteine(s), N-terminal extension, C-terminal processing, glycosylation differences, etc.

A protein "retains its physical stability" in a pharmaceutical formulation if it shows no signs or very little of aggregation, precipitation and/or denaturation upon visual examination of color and/or clarity, or as measured by UV light scattering or by size exclusion chromatography.

A protein "retains its chemical stability" in a pharmaceutical formulation, if the chemical stability at a given time is such that the protein is considered to still retain its biological activity as defined below. Chemical stability can be assessed by detecting and quantifying chemically altered forms of the protein. Chemical alteration may involve protein oxidation which can be evaluated using tryptic peptide mapping, reverse-phase high-performance liquid chromatography (HPLC) and liquid chromatography-mass spectrometry (LC/MS), for example. Other types of chemical alteration include charge alteration of the protein which can be evaluated by ion-exchange chromatography or icIEF, for example.

A protein "retains its biological activity" in a pharmaceutical formulation, if the biological activity of the protein at a given time is within about 10% (within the errors of the assay) of the biological activity exhibited at the time the pharmaceutical formulation was prepared as determined for example in an antigen binding assay for a monoclonal antibody.

As used herein, "biological activity" of a protein refers to the ability of the protein to bind its target, for example the ability of a monoclonal antibody to bind to an antigen. It can further include a biological response which can be measured in vitro or in vivo. Such activity may be antagonistic or agonistic.

A protein which is "susceptible to oxidation" is one comprising one or more residue(s) that has been found to be prone to oxidation such as, but not limited to, methionine (Met), cysteine (Cys), histidine (His), tryptophan (Trp), and tyrosine (Tyr). For example, a tryptophan amino acid in the Fab portion of a monoclonal antibody or a methionine amino acid in the Fc portion of a monoclonal antibody may be susceptible to oxidation.

By "isotonic" is meant that the formulation of interest has essentially the same osmotic pressure as human blood. Isotonic formulations will generally have an osmotic pressure from about 250 to 350 mOsm. Isotonicity can be measured using a vapor pressure or ice-freezing type osmometer, for example.

As used herein, "buffer" refers to a buffered solution that resists changes in pH by the action of its acid-base conjugate components. The buffer of this invention preferably has a pH in the range from about 4.5 to about 8.0. For example, histidine acetate is an example of a buffer that will control the pH in this range.

A "preservative" is a compound which can be optionally included in the formulation to essentially reduce bacterial action therein, thus facilitating the production of a multi-use formulation, for example. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol. In one embodiment, the preservative herein is benzyl alcohol.

As used herein, a "surfactant" refers to a surface-active agent, preferably a nonionic surfactant. Examples of surfactants herein include polysorbate (for example, polysorbate 20 and, polysorbate 80); poloxamer (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearylsarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; and the MONAQUAT™ series (Mona Industries, Inc., Paterson, N.J.); polyethyl glycol, polypropyl glycol, and copolymers of ethylene and propylene glycol (e.g. Pluronics, PF68 etc); etc.

"Pharmaceutically acceptable" excipients or carriers as used herein include pharmaceutically acceptable carriers, stabilizers, buffers, acids, bases, sugars, preservatives, surfactants, tonicity agents, and the like, which are well known in the art (Remington: The Science and Practice of Pharmacy, 22nd Ed., Pharmaceutical Press, 2012). Examples of pharmaceutically acceptable excipients include buffers such as phosphate, citrate, acetate, and other organic acids; antioxidants including ascorbic acid, L-tryptophan and methionine; low molecular weight (less than about 10 residues) polypeptides; proteins, such as serum albumin, gelatin, or immunoglobulins; hydrophilic polymers such as polyvinylpyrrolidone (PVP); amino acids such as glycine, glutamine, asparagine, arginine or lysine; monosaccharides, disaccharides, and other carbohydrates including glucose, mannose, or dextrins; metal complexes such as Zn-protein complexes; chelating agents such as EDTA; sugar alcohols such as mannitol or sorbitol; salt-forming counterions such as sodium; and/or nonionic surfactants such as polysorbate, poloxamer, polyethylene glycol (PEG), and PLURONICS™. "Pharmaceutically acceptable" excipients or carriers are those which can reasonably be administered to a subject to provide an effective dose of the active ingredient employed and that are nontoxic to the subject being exposed thereto at the dosages and concentrations employed.

The term "polysorbate" (also abbreviated as PS) as used herein refers to PEGylated sorbitan esterified with fatty acids and includes polysorbate 20 (polyoxyethylene (20) sorbitan monolaurate), polysorbate 40 (polyoxyethylene (20) sorbitan monopalmitate), polysorbate 60 (polyoxyethylene (20) sorbitan monostearate), and polysorbate 80 (polyoxyethylene (20) sorbitan monooleate).

The term "cyclodextrin" refers to a family of compounds comprising glucose molecules bound in a ring-like structure with d-glucopyranose units linked with alpha-(1,4) glycosidic bonds. Exemplary cyclodextrins include 2-hydroxypropyl-β-cyclodextrin (HP-β-CD or HP-beta-cyclodextrin), 2-hydroxypropyl-α-cyclodextrin (HP-α-CD or HP-alpha-cyclodextrin), 2-hydroxypropyl-γ-cyclodextrin (HP-γ-CD or HP-gamma-cyclodextrin), β-cyclodextrin (β-CD or beta-cyclodextrin), sulfobutyl ether β-cyclodextrin (SBE-β-CD or SBE-beta-cyclodextrin), α-cyclodextrin (α-CD or alpha-cyclodextrin), and γ-cyclodextrin (γ-CD or gamma-cyclodextrin). Synonyms for cyclodextrin include Cavitron, cyclic oligosaccharide, cycloamulose, and cycloglucan.

The term "tonicity agent" refers to an agent that is used to adjust or maintain the relative concentration of solutions. Preferred tonicity agents include polyhydric sugar alcohols, preferably trihydric or higher sugar alcohols, such as glycerin, erythritol, arabitol, xylitol, sorbitol and mannitol.

The term "stabilizer" refers to agents that stabilize large charged biomolecules, such as proteins and antibodies. Tonicity agents may also serve as stabilizers, when used with large charged biomolecules.

"Reduced polysorbate degradation" refers to conditions, where after a period of time more polysorbate remains in a sample compared to a control under similar storage conditions. For example, a sample that has 95% polysorbate remaining after a period of time shows reduced polysorbate degradation compared to a control sample that has 50% of polysorbate remaining after the same time period.

The term "disaggregate" as used herein refers to the reduction in visible and/or subvisible particles that are caused by polysorbate degradation. For example, an agent is effective at disaggregating polysorbate degradation products if the amounts of visible and/or subvisible particles are reduced when it is added to a solution containing polysorbate.

The term "solubilize" refers to dissolving a solid in a liquid. For example, an agent is effective at solubilizing a compound, if the compound dissolves more readily in that agent's presence.

The term "w/w ratio" refers to the amount of one solute by mass divided by the amount of another solute by mass. For example, a solution that contains 100 mg of cyclodextrin and 1 mg of polysorbate, has a w/w ratio of cyclodextrin to polysorbate of 100:1. According to one embodiment the w/w ratio of cyclodextrin to polysorbate is greater than about 37.5:1.

An "aqueous formulation" refers to a water-based liquid formulation suitable for administration. The formulation may contain a therapeutic agent, such as an antibody or small molecules and is preferably sterile. Aqueous formulations may also contain buffers, stabilizers, tonicity agents, and excipients.

The protein which is formulated is preferably essentially pure and desirably essentially homogeneous (e.g., free from contaminating proteins etc.). "Essentially pure" protein means a composition comprising at least about 90% by weight of the protein (e.g., monoclonal antibody), based on total weight of the composition, preferably at least about 95% by weight. "Essentially homogeneous" protein means a composition comprising at least about 99% by weight of the protein (e.g., monoclonal antibody), based on total weight of the composition.

The terms "protein" "polypeptide" and "peptide" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, proteins containing one or more analogs of an amino acid (including, for example, unnatural amino acids, etc.), as well as other modifications known in the art. Examples of proteins encompassed within the definition herein include mammalian proteins, such as, e.g., renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; leptin; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; a tumor necrosis factor receptor such as death receptor 5 and CD120; TNF-related apoptosis-inducing ligand (TRAIL); B-cell maturation antigen (BCMA); B-lymphocyte stimulator (BLyS); a proliferation-inducing ligand (APRIL); enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; platelet-derived endothelial cell growth factor (PD-ECGF); a vascular endothelial growth factor family protein (e.g., VEGF-A, VEGF-B, VEGF-C, VEGF-D, and P1GF); a platelet-derived growth factor (PDGF) family protein (e.g., PDGF-A, PDGF-B, PDGF-C, PDGF-D, and dimers thereof); fibroblast growth factor (FGF) family such as aFGF, bFGF, FGF4, and FGF9; epidermal growth factor (EGF); receptors for hormones or growth factors such as a VEGF receptor(s) (e.g., VEGFR1, VEGFR2, and VEGFR3), epidermal growth factor (EGF) receptor(s) (e.g., ErbB1, ErbB2, ErbB3, and ErbB4 receptor), platelet-derived growth factor (PDGF) receptor(s) (e.g., PDGFR-α and PDGFR-β), and fibroblast growth factor receptor(s); TIE ligands (Angiopoietins, ANGPT1, ANGPT2); Angiopoietin receptor such as TIE1 and TIE2; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-b; transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins (IGFBPs); CD proteins such as CD3, CD4, CD8, CD19 and CD20; erythropoietin; osteoinductive factors; immunotoxins; a bone morphogenetic protein (BMP); a chemokine such as CXCL12 and CXCR4; an interferon such as interferon-alpha, -beta, and -gamma; colony stimulating factors (CSFs), e.g., M-CSF, GM-CSF, and G-CSF; a cytokine such as interleukins (ILs), e.g., IL-1 to IL-10; midkine; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; ephrins; Bv8; Delta-like ligand 4 (DLL4); Del-1; BMP9; BMP10; Follistatin; Hepatocyte growth factor (HGF)/scatter factor (SF); Alk1; Robo4; ESM1; Perlecan; EGF-like domain, multiple 7 (EGFL7); CTGF and members of its family; thrombospondins such as thrombospondin1 and thrombospondin2; collagens such as collagen IV and collagen XVIII; neuropilins such as NRP1 and NRP2; Pleiotrophin (PTN); Progranulin; Proliferin; Notch proteins such as Notch1 and Notch4; semaphorins such as Sema3A, Sema3C, and Sema3F; a tumor associated antigen such as CA125 (ovarian cancer antigen); immunoadhesins; and fragments and/or variants of any of the above-listed proteins as well as antibodies, including antibody fragments, binding to one or more protein, including, for example, any of the above-listed proteins.

The term "antibody" herein is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

An "isolated" protein (e.g., an isolated antibody) is one which has been identified and separated and/or recovered from a component of its natural environment. Contaminant components of its natural environment are materials which would interfere with research, diagnostic or therapeutic uses for the protein, and may include enzymes, hormones, and other proteinaceous or nonproteinaceous solutes. Isolated protein includes the protein in situ within recombinant cells since at least one component of the protein's natural environment will not be present. Ordinarily, however, isolated protein will be prepared by at least one purification step.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

The term "constant domain" refers to the portion of an immunoglobulin molecule having a more conserved amino acid sequence relative to the other portion of the immunoglobulin, the variable domain, which contains the antigen binding site. The constant domain contains the CH1, CH2 and CH3 domains (collectively, CH) of the heavy chain and the CHL (or CL) domain of the light chain.

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) or both in the light-chain and the heavy-chain variable domains. In some embodiments, the HVRs are Complementarity Determining Regions (CDRs).

The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any mammalian species can be assigned to one of two clearly distinct types, called kappa ("κ") and lambda ("λ"), based on the amino acid sequences of their constant domains.

The term IgG "isotype" or "subclass" as used herein is meant any of the subclasses of immunoglobulins defined by the chemical and antigenic characteristics of their constant regions. Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively. The subunit structures and three-dimensional configurations of different classes of immunoglobulins are well known and described generally in, for example, Abbas et al. *Cellular and Mol. Immunology*, 4th ed., W.B. Saunders, Co. (2000). An antibody may be part of a larger fusion molecule, formed by covalent or non-covalent association of the antibody with one or more other proteins or peptides.

The terms "full length antibody," "intact antibody" and "whole antibody" are used herein interchangeably to refer to an antibody in its substantially intact form, not antibody fragments as defined below. The terms particularly refer to an antibody with heavy chains that contain an Fc region.

"Antibody fragments" comprise a portion of an intact antibody, preferably comprising the antigen binding region thereof. Examples of antibody fragments include Fab, Fab', F(ab')$_2$, and Fv fragments; diabodies; linear antibodies; single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen. The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv, see, e.g., Pluckthün, in *The Pharmacology of Monoclonal Antibodies*, vol. 113, Rosenburg and Moore eds., Springer-Verlag, New York, pp. 269-315 (1994).

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

The term "monoclonal antibody" as used herein refers to an antibody obtained from a population of substantially homogeneous antibodies, e.g., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the invention may be made by a variety of techniques, including, for example, the hybridoma method (e.g., Kohler and Milstein, Nature, 256:495-97 (1975); Hongo et al., *Hybridoma,* 14 (3): 253-260 (1995), Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* pp. 563-681 Elsevier, N.Y. (1981)), recombinant DNA methods (see, e.g., U.S. Pat. No. 4,816,567), phage-display technologies (see, e.g., Clackson et al., *Nature,* 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg and Huszar, *Intern. Rev. Immunol.* 13: 65-93 (1995)).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; and Morrison et al., *Proc. Natl. Acad. Sci. USA* 81:6851-6855 (1984)). Chimeric antibodies include PRIMATIZED® antibodies wherein the antigen-binding region of the antibody is derived from an antibody produced by, e.g., immunizing macaque monkeys with the antigen of interest.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a HVR of the recipient are replaced by residues from a HVR of a non-human species (donor antibody) such as mouse, rat, rabbit, or nonhuman primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, e.g., Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.,* 227: 381 (1991); Marks et al., *J. Mol. Biol.,* 222:581 (1991). Also available for the preparation of human monoclonal antibodies are methods described in Cole et al., *Monoclonal Antibodies and Cancer Therapy,* Alan R. Liss, p. 77 (1985); Boerner et al., *J. Immunol.,* 147(1):86-95 (1991). See also van Dijk and van de Winkel, *Curr. Opin. Pharmacol.,* 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Natl. Acad. Sci. USA,* 103:3557-3562 (2006) regarding human antibodies generated via a human B-cell hybridoma technology.

The term "hypervariable region," "HVR," or "HV," when used herein refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu, in *Methods in Molecular Biology* 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., *Nature* 363:446-448 (1993); Sheriff et al., *Nature Struct. Biol.* 3:733-736 (1996).

A number of HVR delineations are in use and are encompassed herein. The Kabat Complementarity Determining Regions (CDRs) are based on sequence variability and are the most commonly used (Kabat et al., *Sequences of Proteins of Immunological Interest,* 5th Ed. Public Health Service, National Institutes of Health, Bethesda, Md. (1991)). Chothia refers instead to the location of the structural loops (Chothia and Lesk *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B |

| Loop | Kabat | AbM | Chothia | Contact |
|------|-------|-----|---------|---------|
| | | (Kabat Numbering) | | |
| H1 | H31-H35 | H26-H35 | H26-H32 | H30-H35 |
| | | (Chothia Numbering) | | |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

"Framework" or "FR" residues are those variable domain residues other than the HVR residues as herein defined.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence The Kabat numbering system is generally used when referring to a residue in the variable domain (approximately residues 1-107 of the light chain and residues 1-113 of the heavy chain) (e.g., Kabat et al., *Sequences of Immunological Interest.* 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody.

The expression "linear antibodies" refers to the antibodies described in Zapata et al. (*Protein Eng.,* 8(10):1057-1062 (1995)). Briefly, these antibodies comprise a pair of tandem Fc segments (VH-CH1-VH-CH1) which, together with complementary light chain polypeptides, form a pair of antigen binding regions. Linear antibodies can be bispecific or monospecific.

Polyclonal antibodies are preferably raised in animals by multiple subcutaneous (sc) or intraperitoneal (ip) injections of the relevant antigen and an adjuvant. It may be useful to conjugate the relevant antigen (especially when synthetic peptides are used) to a protein that is immunogenic in the species to be immunized. For example, the antigen can be conjugated to keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

The term "multispecific antibody" is used in the broadest sense and specifically covers an antibody comprising an antigen-binding domain that has polyepitopic specificity (i.e., is capable of specifically binding to two, or more, different epitopes on one biological molecule or is capable of specifically binding to epitopes on two, or more, different biological molecules). In some embodiments, an antigen-binding domain of a multispecific antibody (such as a bispecific antibody) comprises two VH/VL units, wherein a first VH/VL unit specifically binds to a first epitope and a second VH/VL unit specifically binds to a second epitope, wherein each VH/VL unit comprises a heavy chain variable domain (VH) and a light chain variable domain (VL). Such multispecific antibodies include, but are not limited to, full length antibodies, antibodies having two or more VL and VH domains, antibody fragments such as Fab, Fv, dsFv, scFv, diabodies, bispecific diabodies and triabodies, antibody fragments that have been linked covalently or non-covalently. A VH/VL unit that further comprises at least a portion of a heavy chain constant region and/or at least a portion of a light chain constant region may also be referred to as a "hemimer" or "half antibody." In some embodiments, a half antibody comprises at least a portion of a single heavy chain variable region and at least a portion of a single light chain variable region. In some such embodiments, a bispecific antibody that comprises two half antibodies and binds to two antigens comprises a first half antibody that binds to the first antigen or first epitope but not to the second antigen or second epitope and a second half antibody that binds to the second antigen or second epitope and not to the first antigen or first epitope. According to some embodiments, the multispecific antibody is an IgG antibody that binds to each antigen or epitope with an affinity of 5 M to 0.001 pM, 3 M to 0.001 pM, 1 M to 0.001 pM, 0.5 M to 0.001 pM, or 0.1 M to 0.001 pM. In some embodiments, a hemimer comprises a sufficient portion of a heavy chain variable region to allow intramolecular disulfide bonds to be formed with a second hemimer. In some embodiments, a hemimer comprises a knob mutation or a hole mutation, for example, to allow heterodimerization with a second hemimer or half antibody that comprises a complementary hole mutation or knob mutation. Knob mutations and hole mutations are discussed further below.

A "bispecific antibody" is a multispecific antibody comprising an antigen-binding domain that is capable of specifically binding to two different epitopes on one biological molecule or is capable of specifically binding to epitopes on two different biological molecules. A bispecific antibody may also be referred to herein as having "dual specificity" or as being "dual specific." Unless otherwise indicated, the order in which the antigens bound by a bispecific antibody are listed in a bispecific antibody name is arbitrary. In some embodiments, a bispecific antibody comprises two half antibodies, wherein each half antibody comprises a single heavy chain variable region and optionally at least a portion of a heavy chain constant region, and a single light chain variable region and optionally at least a portion of a light chain constant region. In certain embodiments, a bispecific antibody comprises two half antibodies, wherein each half antibody comprises a single heavy chain variable region and a single light chain variable region and does not comprise more than one single heavy chain variable region and does not comprise more than one single light chain variable region. In some embodiments, a bispecific antibody comprises two half antibodies, wherein each half antibody comprises a single heavy chain variable region and a single light chain variable region, and wherein the first half antibody binds to a first antigen and not to a second antigen and the second half antibody binds to the second antigen and not to the first antigen.

The term "knob-into-hole" or "KnH" technology as used herein refers to the technology directing the pairing of two polypeptides together in vitro or in vivo by introducing a protuberance (knob) into one polypeptide and a cavity (hole) into the other polypeptide at an interface in which they interact. For example, KnHs have been introduced in the Fc:Fc binding interfaces, CL:CH1 interfaces or VH/VL interfaces of antibodies (see, e.g., US 2011/0287009, US2007/0178552, WO 96/027011, WO 98/050431, and Zhu et al., 1997, *Protein Science* 6:781-788). In some embodiments, KnHs drive the pairing of two different heavy chains together during the manufacture of multispecific antibodies. For example, multispecific antibodies having KnH in their Fc regions can further comprise single variable domains linked to each Fc region, or further comprise different heavy chain variable domains that pair with similar or different light chain variable domains. KnH technology can also be used to pair two different receptor extracellular domains together or any other polypeptide sequences that comprises different target recognition sequences (e.g., including affibodies, peptibodies and other Fc fusions).

The term "knob mutation" as used herein refers to a mutation that introduces a protuberance (knob) into a polypeptide at an interface in which the polypeptide interacts with another polypeptide. In some embodiments, the other polypeptide has a hole mutation (see e.g., U.S. Pat. Nos. 5,731,168, 5,807,706, 5,821,333, 7,695,936, 8,216,805, each incorporated herein by reference in its entirety).

The term "hole mutation" as used herein refers to a mutation that introduces a cavity (hole) into a polypeptide at an interface in which the polypeptide interacts with another polypeptide. In some embodiments, the other polypeptide has a knob mutation (see e.g., U.S. Pat. Nos. 5,731,168, 5,807,706, 5,821,333, 7,695,936, 8,216,805, each incorporated herein by reference in its entirety).

The term "about" as used herein refers to an acceptable error range for the respective value as determined by one of ordinary skill in the art, which will depend in part how the value is measured or determined, i.e., the limitations of the measurement system. For example, "about" can mean within 1 or more than 1 standard deviations, per the practice in the art. A reference to "about" a value or parameter herein includes and describes embodiments that are directed to that value or parameter per se. For example, a description referring to "about X" includes description of "X".

As used in this specification and the appended claims, the singular forms "a", "an" and "the" include plural referents unless the content clearly dictates otherwise. Thus, for example, reference to "a compound" optionally includes a combination of two or more such compounds, and the like.

II. Formulations and Preparation

The invention herein relates to methods of reducing polysorbate degradation in an aqueous formulation comprising polysorbate, the method comprising adding a cyclodextrin to the formulation, wherein the resulting w/w ratio of cyclodextrin to polysorbate is greater than about 37.5:1. In some embodiments, the invention provides a method of reducing the amount of sub-visible and visible particles in an aqueous solution comprising polysorbate comprising adding cyclodextrin to a solution wherein the resulting w/w ratio of cyclodextrin to polysorbate is greater than about 37.5:1. In some embodiments, the invention provides a method to disaggregate and solubilize polysorbate degradation products in an aqueous formulation comprising adding a cyclodextrin to the formulation, wherein the resulting w/w ratio of cyclodextrin to polysorbate is greater than about 37.5:1. In some embodiments, the cyclodextrin is HP-βcyclodextrin, HP-γcyclodextrin or sulfobutyl ether beta-cyclodextrin. In some embodiments, the cyclodextrin is HP-α cyclodextrin. In some embodiments, the formulation further comprises a polypeptide.

In some embodiments, the method comprises adding polyvinylpyrrolidone (PVP) to the formulation, wherein the resulting w/w ratio of PVP to polysorbate is greater than about 37.5:1. In some embodiments, the invention provides a method of reducing the amount of sub-visible and visible particles in an aqueous solution comprising polysorbate comprising adding PVP to a solution wherein resulting w/w ratio of PVP to polysorbate is greater than about 37.5:1. In some embodiments, the invention provides a method to disaggregate and solubilize polysorbate degradation products in an aqueous formulation comprising adding PVP to the formulation, wherein the resulting w/w ratio of PVP to polysorbate is greater than about 37.5:1.

In some embodiments, the invention provides an aqueous formulation comprising a polysorbate, and a cyclodextrin, wherein less than 1% of the polysorbate has been degraded after storage at about 1° C. to about 10° C. for at least about six months to at least about 48 months, wherein the w/w ratio of cyclodextrin to polysorbate in the formulation is at least about 37.5:1. In some embodiments, the invention provides an aqueous formulation comprising a polysorbate and PVP, wherein less than 1% of the polysorbate has been degraded after storage at about 1° C. to about 10° C. for at least about six months to at least about 48 months, wherein the w/w ratio of PVP to polysorbate in the formulation is at least about 37.5:1. In some embodiments, the formulation is stable at about 2° C. to about 8° C. for at least about six months to at least about at least about 48 months, at least about 12 months, at least about 18 months, at least about 24 months, or at least about 48 months. In some embodiments, the formulation comprises about 0.005%-0.4% polysorbate. In some embodiments, the formulation comprises about 0.005%-0.4% polysorbate and the cyclodextrin is added to the formulation to a concentration of about 0.01%-30%. In some embodiments, the cyclodextrin is HP-βcyclodextrin, HP-γcyclodextrin or sulfobutyl ether beta-cyclodextrin. In some embodiments, the cyclodextrin is HP-α cyclodextrin. In some embodiments the polysorbate degradation is reduced by about 50%, about 75%, about 80%, about 85%, about 90%, about 95%, or about 99%. In further embodiments, less than about 1,000, about 750, about 500, about 250, about 150, about 100, about 50, or about 25 polysorbate particles greater than about two microns in diameter are formed per mL. In some embodiments, the formulation further comprises a polypeptide. In some embodiments, the protein concentration is about 1 mg/mL to about 250 mg/mL. In some embodiments, the protein concentration is greater than about 250 mg/mL. In some embodiments, the formulation has a pH of about 4.5 to about 7.0 or about 4.5 to about 6.0, or of about 6.0. In some embodiments, the formulation further comprises one or more of a stabilizer, a buffer, a surfactant, and a tonicity agent. In further embodiments, the formulation is suitable for intravenous, subcutaneous intramuscular, or intravitreal administration to a subject. In some embodiments, the polypeptide is a polyclonal antibody, a monoclonal antibody, a humanized antibody, a human antibody, a chimeric antibody, a multispecific antibody, or an antibody fragment. In some embodiments, the formulation further comprises a small molecule, a nucleic acid, a lipid and/or a carbohydrate.

Proteins and antibodies in the formulation may be prepared using methods known in the art. Provided herein are non-limiting exemplary methods for preparing an antibody (e.g., full length antibodies, antibody fragments and multispecific antibodies). The antibody in the aqueous formulation is prepared using techniques available in the art for generating antibodies, exemplary methods of which are described in more detail in the following sections. The methods herein can be adapted by one of skill in the art for the preparation of formulations comprising other proteins such as peptide-based inhibitors. See Sam Sambrook et al., *Molecular Cloning: A Laboratory Manual,* 4th ed., Cold Spring Harbor Laboratory Press, Cold Spring Harbor, N.Y. (2012); *Current Protocols in Molecular Biology,* F. M. Ausubel, et al. eds. (2003); Short Protocols in Molecular Biology, Ausubel et al., eds., J. Wiley and Sons (2002); Horswill et al., *Current Protocols in Protein Science,* (2006); Antibodies, *A Laboratory Manual,* Harlow and Lane, eds. (1988); R. I. Freshney, *Culture of Animal Cells: A Manual of Basic Technique and Specialized Application,* 6th ed., J. Wiley and Sons (2010) for generally well understood and commonly employed techniques and procedures for the production of therapeutic proteins, which are all incorporated herein by reference in their entirety.

A. Antibody Preparation

The antibody in the aqueous formulations provided herein is directed against an antigen of interest. Preferably, the antigen is a biologically important polypeptide and administration of the antibody to a mammal suffering from a disorder can result in a therapeutic benefit in that mammal. However, antibodies directed against nonpolypeptide antigens are also contemplated.

Where the antigen is a polypeptide, it may be a transmembrane molecule (e.g. receptor) or ligand such as a growth factor. Exemplary antigens include molecules such as vascular endothelial growth factor (VEGF); CD20; ox-LDL; ox-ApoB100; renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; receptors for hormones or growth factors; protein A or D; rheumatoid factors; a neurotrophic factor such as bone-derived neurotrophic factor (BDNF), neurotrophin-3, -4, -5, or -6 (NT-3, NT4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des (1-3)-IGF-I (brain IGF-I), insulin-like growth factor binding proteins; CD proteins such as CD3, CD4, CD8, CD19 and CD20; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrns such as CD11a, CD11b, CD11c, CD18, an ICAM, VLA-4 and VCAM; a tumor associated antigen such as HER2, HER3 or HER4 receptor; and fragments of any of the above-listed polypeptides.

(i) Antigen Preparation

Soluble antigens or fragments thereof, optionally conjugated to other molecules, can be used as immunogens for generating antibodies. For transmembrane molecules, such as receptors, fragments of these (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule. Other antigens and forms thereof useful for preparing antibodies will be apparent to those in the art.

(ii) Certain Antibody-Based Methods

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with ⅕ to 1/10 the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibodies of the invention can be made using the hybridoma method first described by Kohler et al., *Nature,* 256:495 (1975), and further described, e.g., in Hongo et al., *Hybridoma,* 14 (3): 253-260 (1995), Harlow et al., *Antibodies: A Laboratory Manual,* (Cold Spring Harbor Laboratory Press, 2nd ed. 1988); Hammerling et al., in: *Monoclonal Antibodies and T-Cell Hybridomas* 563-681 (Elsevier, N.Y., 1981), and Ni, *Xiandai Mianyixue,* 26(4): 265-268 (2006) regarding human-human hybridomas. Additional methods include those described, for example, in U.S. Pat. No. 7,189,826 regarding production of monoclonal human natural IgM antibodies from hybridoma cell lines. Human hybridoma technology (Trioma technology) is described in Vollmers and Brandlein, *Histology and Histopathology*, 20(3):927-937 (2005) and Vollmers and Brandlein, *Methods and Findings in Experimental and Clinical Pharmacology*, 27(3):185-91 (2005).

For various other hybridoma techniques, see, e.g., US 2006/258841; US 2006/183887 (fully human antibodies), US 2006/059575; US 2005/287149; US 2005/100546; US 2005/026229; and U.S. Pat. Nos. 7,078,492 and 7,153,507. An exemplary protocol for producing monoclonal antibodies using the hybridoma method is described as follows. In one embodiment, a mouse or other appropriate host animal, such as a hamster, is immunized to elicit lymphocytes that produce or are capable of producing antibodies that will specifically bind to the protein used for immunization. Antibodies are raised in animals by multiple subcutaneous (sc) or intraperitoneal (ip) injections of a polypeptide of the invention or a fragment thereof, and an adjuvant, such as monophosphoryl lipid A (MPL)/trehalose dicrynomycolate (TDM) (Ribi Immunochem. Research, Inc., Hamilton, Mont.). A polypeptide of the invention (e.g., antigen) or a fragment thereof may be prepared using methods well known in the art, such as recombinant methods, some of which are further described herein. Serum from immunized animals is assayed for anti-antigen antibodies, and booster immunizations are optionally administered. Lymphocytes from animals producing anti-antigen antibodies are isolated. Alternatively, lymphocytes may be immunized in vitro.

Lymphocytes are then fused with myeloma cells using a suitable fusing agent, such as polyethylene glycol, to form a hybridoma cell. See, e.g., Goding, *Monoclonal Antibodies: Principles and Practice*, pp. 59-103 Academic Press, (1986). Myeloma cells may be used that fuse efficiently, support stable high-level production of antibody by the selected antibody-producing cells, and are sensitive to a medium such as HAT medium. Exemplary myeloma cells include, but are not limited to, murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 Marcel Dekker, Inc., New York (1987).

The hybridoma cells thus prepared are seeded and grown in a suitable culture medium, e.g., a medium that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells. Preferably, serum-free hybridoma cell culture methods are used to reduce use of animal-derived serum such as fetal bovine serum, as described, for example, in Even et al., *Trends in Biotechnology*, 24(3), 105-108 (2006).

Oligopeptides as tools for improving productivity of hybridoma cell cultures are described in Franek, *Trends in Monoclonal Antibody Research*, 111-122 (2005). Specifically, standard culture media are enriched with certain amino acids (alanine, serine, asparagine, proline), or with protein hydrolyzate fractions, and apoptosis may be significantly suppressed by synthetic oligopeptides, constituted of three to six amino acid residues. The peptides are present at millimolar or higher concentrations.

Culture medium in which hybridoma cells are growing may be assayed for production of monoclonal antibodies that bind to an antibody of the invention. The binding specificity of monoclonal antibodies produced by hybridoma cells may be determined by immunoprecipitation or by an in vitro binding assay, such as radioimmunoassay (RIA) or enzyme-linked immunoadsorbent assay (ELISA). The binding affinity of the monoclonal antibody can be determined, for example, by Scatchard analysis. See, e.g., Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods. See, e.g., Goding, supra. Suitable culture media for this purpose include, for example, D-MEM or RPMI-1640 medium. In addition, hybridoma cells may be grown in vivo as ascites tumors in an animal. Monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography. One procedure for isolation of proteins from hybridoma cells is described in US 2005/176122 and U.S. Pat. No. 6,919,436. The method includes using minimal salts, such as lyotropic salts, in the binding process and preferably also using small amounts of organic solvents in the elution process.

(iii) Certain Library Screening Methods

Antibodies of the invention can be made by using combinatorial libraries to screen for antibodies with the desired activity or activities. For example, a variety of methods are known in the art for generating phage display libraries and screening such libraries for antibodies possessing the desired binding characteristics. Such methods are described generally in Hoogenboom et al. in *Methods in Molecular Biology* 178:1-37, O'Brien et al., ed., Human Press, Totowa, N.J., (2001). For example, one method of generating antibodies of interest is through the use of a phage antibody library as described in Lee et al., *J. Mol. Biol.* 340(5):1073-93 (2004).

In principle, synthetic antibody clones are selected by screening phage libraries containing phage that display various fragments of antibody variable region (Fv) fused to phage coat protein. Such phage libraries are panned by affinity chromatography against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution. Any of the antibodies of the invention can be obtained by designing a suitable antigen screening procedure to select for the phage clone of interest followed by construction of a full length antibody clone using the Fv sequences from the phage clone of interest and suitable constant region (Fc) sequences described in Kabat et al., *Sequences of Proteins of Immunological Interest*, Fifth Edition, NIH Publication 1-3:91-3242, Bethesda Md. (1991).

In certain embodiments, the antigen-binding domain of an antibody is formed from two variable (V) regions of about 110 amino acids, one each from the light (VL) and heavy (VH) chains, that both present three hypervariable loops (HVRs) or complementarity-determining regions (CDRs). Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described in Winter et al., *Ann. Rev. Immunol.,* 12: 433-455 (1994). As used herein, scFv encoding phage clones and Fab encoding phage clones are collectively referred to as "Fv phage clones" or "Fv clones."

Repertoires of VH and VL genes can be separately cloned by polymerase chain reaction (PCR) and recombined randomly in phage libraries, which can then be searched for antigen-binding clones as described in Winter et al., *Ann. Rev. Immunol.,* 12: 433-455 (1994). Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al., *EMBO J,* 12: 725-734 (1993). Finally, naive libraries can also be made synthetically by cloning the unrearranged V-gene segments from stem cells, and using PCR primers containing random sequence to encode the highly variable CDR3 regions and to accomplish rearrangement in vitro as described by Hoogenboom and Winter, *J. Mol. Biol.,* 227: 381-388 (1992).

In certain embodiments, filamentous phage is used to display antibody fragments by fusion to the minor coat protein pIII. The antibody fragments can be displayed as single chain Fv fragments, in which VH and VL domains are connected on the same polypeptide chain by a flexible polypeptide spacer, e.g. as described by Marks et al., *J. Mol. Biol.,* 222: 581-597 (1991), or as Fab fragments, in which one chain is fused to pIII and the other is secreted into the bacterial host cell periplasm where assembly of a Fab-coat protein structure which becomes displayed on the phage surface by displacing some of the wild type coat proteins, e.g. as described in Hoogenboom et al., *Nucl. Acids Res.,* 19: 4133-4137 (1991).

In general, nucleic acids encoding antibody gene fragments are obtained from immune cells harvested from humans or animals. If a library biased in favor of anti-antigen clones is desired, the subject is immunized with antigen to generate an antibody response, and spleen cells and/or circulating B cells other peripheral blood lymphocytes (PBLs) are recovered for library construction. In one embodiment, a human antibody gene fragment library biased in favor of anti-antigen clones is obtained by generating an anti-antigen antibody response in transgenic mice carrying a functional human immunoglobulin gene array (and lacking a functional endogenous antibody production system) such that antigen immunization gives rise to B cells producing human antibodies against antigen. The generation of human antibody-producing transgenic mice is described below.

Additional enrichment for anti-antigen reactive cell populations can be obtained by using a suitable screening procedure to isolate B cells expressing antigen-specific membrane bound antibody, e.g., by cell separation using antigen affinity chromatography or adsorption of cells to fluorochrome-labeled antigen followed by flow-activated cell sorting (FACS).

Alternatively, the use of spleen cells and/or B cells or other PBLs from an unimmunized donor provides a better representation of the possible antibody repertoire, and also permits the construction of an antibody library using any animal (human or non-human) species in which antigen is not antigenic. For libraries incorporating in vitro antibody gene construction, stem cells are harvested from the subject to provide nucleic acids encoding unrearranged antibody gene segments. The immune cells of interest can be obtained from a variety of animal species, such as human, mouse, rat, lagomorpha, luprine, canine, feline, porcine, bovine, equine, and avian species, etc.

Nucleic acid encoding antibody variable gene segments (including VH and VL segments) are recovered from the cells of interest and amplified. In the case of rearranged VH and VL gene libraries, the desired DNA can be obtained by isolating genomic DNA or mRNA from lymphocytes followed by polymerase chain reaction (PCR) with primers matching the 5' and 3' ends of rearranged VH and VL genes as described in Orlandi et al., *Proc. Natl. Acad. Sci. (USA),* 86: 3833-3837 (1989), thereby making diverse V gene repertoires for expression. The V genes can be amplified from cDNA and genomic DNA, with back primers at the 5' end of the exon encoding the mature V-domain and forward primers based within the J-segment as described in Orlandi et al. (1989) and in Ward et al., *Nature,* 341: 544-546 (1989). However, for amplifying from cDNA, back primers can also be based in the leader exon as described in Jones et al., *Biotechnol.,* 9: 88-89 (1991), and forward primers within the constant region as described in Sastry et al., *Proc. Natl. Acad. Sci. (USA),* 86: 5728-5732 (1989). To maximize complementarity, degeneracy can be incorporated in the primers as described in Orlandi et al. (1989) or Sastry et al. (1989). In certain embodiments, library diversity is maximized by using PCR primers targeted to each V-gene family in order to amplify all available VH and VL arrangements present in the immune cell nucleic acid sample, e.g. as described in the method of Marks et al., *J. Mol. Biol.,* 222: 581-597 (1991) or as described in the method of Orum et al., *Nucleic Acids Res.,* 21: 4491-4498 (1993). For cloning of the amplified DNA into expression vectors, rare restriction sites can be introduced within the PCR primer as a tag at one end as described in Orlandi et al. (1989), or by further PCR amplification with a tagged primer as described in Clackson et al., *Nature,* 352: 624-628 (1991).

Repertoires of synthetically rearranged V genes can be derived in vitro from V gene segments. Most of the human VH-gene segments have been cloned and sequenced (reported in Tomlinson et al., *J. Mol. Biol.,* 227: 776-798 (1992)), and mapped (reported in Matsuda et al., *Nature Genet.,* 3: 88-94 (1993); these cloned segments (including all the major conformations of the H1 and H2 loop) can be used to generate diverse VH gene repertoires with PCR primers encoding H3 loops of diverse sequence and length as described in Hoogenboom and Winter, *J. Mol. Biol.,* 227: 381-388 (1992). VH repertoires can also be made with all the sequence diversity focused in a long H3 loop of a single length as described in Barbas et al., *Proc. Natl. Acad. Sci. USA,* 89: 4457-4461 (1992). Human Vκ and Vλ, segments have been cloned and sequenced (reported in Williams and Winter, *Eur. J. Immunol.,* 23: 1456-1461 (1993)) and can be used to make synthetic light chain repertoires. Synthetic V gene repertoires, based on a range of VH and VL folds, and L3 and H3 lengths, will encode antibodies of considerable structural diversity. Following amplification of V-gene encoding DNAs, germline V-gene segments can be rearranged in vitro according to the methods of Hoogenboom and Winter, *J. Mol. Biol.,* 227: 381-388 (1992).

Repertoires of antibody fragments can be constructed by combining VH and VL gene repertoires together in several ways. Each repertoire can be created in different vectors, and the vectors recombined in vitro, e.g., as described in Hogrefe et al., *Gene,* 128: 119-126 (1993), or in vivo by combinatorial infection, e.g., the loxP system described in Waterhouse et al., *Nucl. Acids Res.,* 21: 2265-2266 (1993). The in vivo recombination approach exploits the two-chain nature of Fab fragments to overcome the limit on library size imposed by *E. coli* transformation efficiency. Naive VH and VL repertoires are cloned separately, one into a phagemid and the other into a phage vector. The two libraries are then combined by phage infection of phagemid-containing bacteria so that each cell contains a different combination and the library size is limited only by the number of cells present (about $10^{12}$ clones). Both vectors contain in vivo recombination signals so that the VH and VL genes are recombined onto a single replicon and are co-packaged into phage virions. These huge libraries provide large numbers of diverse antibodies of good affinity ($K_d^{-1}$ of about $10^{-8}$ M).

Alternatively, the repertoires may be cloned sequentially into the same vector, e.g. as described in Barbas et al., *Proc. Natl. Acad. Sci. USA,* 88: 7978-7982 (1991), or assembled together by PCR and then cloned, e.g. as described in Clackson et al., *Nature,* 352: 624-628 (1991). PCR assembly can also be used to join VH and VL DNAs with DNA encoding a flexible peptide spacer to form single chain Fv (scFv) repertoires. In yet another technique, "in cell PCR assembly" is used to combine VH and VL genes within lymphocytes by PCR and then clone repertoires of linked genes as described in Embleton et al., *Nucl. Acids Res.,* 20: 3831-3837 (1992).

The antibodies produced by naive libraries (either natural or synthetic) can be of moderate affinity ($K_d^{-1}$ of about $10^6$ to $10^7$ M$^{-1}$), but affinity maturation can also be mimicked in vitro by constructing and reselecting from secondary libraries as described in Winter et al. (1994), supra. For example, mutation can be introduced at random in vitro by using error-prone polymerase (reported in Leung et al., *Technique* 1:11-15 (1989)) in the method of Hawkins et al., *J. Mol. Biol.,* 226: 889-896 (1992) or in the method of Gram et al., *Proc. Natl. Acad. Sci USA,* 89: 3576-3580 (1992). Additionally, affinity maturation can be performed by randomly mutating one or more CDRs, e.g. using PCR with primers carrying random sequence spanning the CDR of interest, in selected individual Fv clones and screening for higher affinity clones. WO 9607754 (published 14 Mar. 1996) described a method for inducing mutagenesis in a complementarity determining region of an immunoglobulin light chain to create a library of light chain genes. Another effective approach is to recombine the VH or VL domains selected by phage display with repertoires of naturally occurring V domain variants obtained from unimmunized donors and screen for higher affinity in several rounds of chain reshuffling as described in Marks et al., *Biotechnol.,* 10: 779-783 (1992). This technique allows the production of antibodies and antibody fragments with affinities of about $10^{-9}$ M or less.

Screening of the libraries can be accomplished by various techniques known in the art. For example, antigen can be used to coat the wells of adsorption plates, expressed on host cells affixed to adsorption plates or used in cell sorting, or conjugated to biotin for capture with streptavidin-coated beads, or used in any other method for panning phage display libraries.

The phage library samples are contacted with immobilized antigen under conditions suitable for binding at least a portion of the phage particles with the adsorbent. Normally, the conditions, including pH, ionic strength, temperature and the like are selected to mimic physiological conditions. The phages bound to the solid phase are washed and then eluted by acid, e.g. as described in Barbas et al., *Proc. Natl. Acad. Sci USA,* 88: 7978-7982 (1991), or by alkali, e.g. as described in Marks et al., *J. Mol. Biol.,* 222: 581-597 (1991), or by antigen competition, e.g. in a procedure similar to the antigen competition method of Clackson et al., *Nature,* 352: 624-628 (1991). Phages can be enriched 20-1,000-fold in a single round of selection. Moreover, the enriched phages can be grown in bacterial culture and subjected to further rounds of selection.

The efficiency of selection depends on many factors, including the kinetics of dissociation during washing, and whether multiple antibody fragments on a single phage can simultaneously engage with antigen. Antibodies with fast dissociation kinetics (and weak binding affinities) can be retained by use of short washes, multivalent phage display and high coating density of antigen in solid phase. The high density not only stabilizes the phage through multivalent interactions, but favors rebinding of phage that has dissociated. The selection of antibodies with slow dissociation kinetics (and good binding affinities) can be promoted by use of long washes and monovalent phage display as described in Bass et al., *Proteins,* 8: 309-314 (1990) and in WO 92/09690, and a low coating density of antigen as described in Marks et al., *Biotechnol.,* 10: 779-783 (1992).

It is possible to select between phage antibodies of different affinities, even with affinities that differ slightly, for antigen. However, random mutation of a selected antibody (e.g. as performed in some affinity maturation techniques) is likely to give rise to many mutants, most binding to antigen, and a few with higher affinity. With limiting antigen, rare high affinity phage could be competed out. To retain all higher affinity mutants, phages can be incubated with excess biotinylated antigen, but with the biotinylated antigen at a concentration of lower molarity than the target molar affinity constant for antigen. The high affinity-binding phages can then be captured by streptavidin-coated paramagnetic beads. Such "equilibrium capture" allows the antibodies to be selected according to their affinities of binding, with sensitivity that permits isolation of mutant clones with as little as two-fold higher affinity from a great excess of phages with lower affinity. Conditions used in washing phages bound to a solid phase can also be manipulated to discriminate on the basis of dissociation kinetics.

Anti-antigen clones may be selected based on activity. In certain embodiments, the invention provides anti-antigen antibodies that bind to living cells that naturally express antigen or bind to free floating antigen or antigen attached to other cellular structures. Fv clones corresponding to such anti-antigen antibodies can be selected by (1) isolating anti-antigen clones from a phage library as described above, and optionally amplifying the isolated population of phage clones by growing up the population in a suitable bacterial host; (2) selecting antigen and a second protein against which blocking and non-blocking activity, respectively, is desired; (3) adsorbing the anti-antigen phage clones to immobilized antigen; (4) using an excess of the second protein to elute any undesired clones that recognize antigen-binding determinants which overlap or are shared with the binding determinants of the second protein; and (5) eluting the clones which remain adsorbed following step (4). Optionally, clones with the desired blocking/non-blocking properties can be further enriched by repeating the selection procedures described herein one or more times.

DNA encoding hybridoma-derived monoclonal antibodies or phage display Fv clones of the invention is readily isolated and sequenced using conventional procedures (e.g.

by using oligonucleotide primers designed to specifically amplify the heavy and light chain coding regions of interest from hybridoma or phage DNA template). Once isolated, the DNA can be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of the desired monoclonal antibodies in the recombinant host cells. Review articles on recombinant expression in bacteria of antibody-encoding DNA include Skerra et al., Curr. Opinion in Immunol., 5: 256 (1993) and Pluckthun, Immunol. Revs, 130: 151 (1992).

DNA encoding the Fv clones of the invention can be combined with known DNA sequences encoding heavy chain and/or light chain constant regions (e.g. the appropriate DNA sequences can be obtained from Kabat et al., supra) to form clones encoding full or partial length heavy and/or light chains. It will be appreciated that constant regions of any isotype can be used for this purpose, including IgG, IgM, IgA, IgD, and IgE constant regions, and that such constant regions can be obtained from any human or animal species. An Fv clone derived from the variable domain DNA of one animal (such as human) species and then fused to constant region DNA of another animal species to form coding sequence(s) for "hybrid," full length heavy chain and/or light chain is included in the definition of "chimeric" and "hybrid" antibody as used herein. In certain embodiments, an Fv clone derived from human variable DNA is fused to human constant region DNA to form coding sequence(s) for full- or partial-length human heavy and/or light chains.

DNA encoding anti-antigen antibody derived from a hybridoma of the invention can also be modified, for example, by substituting the coding sequence for human heavy- and light-chain constant domains in place of homologous murine sequences derived from the hybridoma clone (e.g. as in the method of Morrison et al., Proc. Natl. Acad. Sci. USA, 81: 6851-6855 (1984)). DNA encoding a hybridoma- or Fv clone-derived antibody or fragment can be further modified by covalently joining to the immunoglobulin coding sequence all or part of the coding sequence for a non-immunoglobulin polypeptide. In this manner, "chimeric" or "hybrid" antibodies are prepared that have the binding specificity of the Fv clone or hybridoma clone-derived antibodies of the invention.

(iv) Humanized and Human Antibodies

Various methods for humanizing non-human antibodies are known in the art. For example, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987)). Another method uses a particular framework derived from the consensus sequence of all human antibodies of a particular subgroup of light or heavy chains. The same framework may be used for several different humanized antibodies (Carter et al., Proc. Natl. Acad Sci. USA, 89:4285 (1992); Presta et al., J. Immunol., 151:2623 (1993)).

It is further important that antibodies be humanized with retention of high affinity for the antigen and other favorable biological properties. To achieve this goal, according to one embodiment of the method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Human antibodies of the invention can be constructed by combining Fv clone variable domain sequence(s) selected from human-derived phage display libraries with known human constant domain sequence(s) as described above. Alternatively, human monoclonal antibodies of the invention can be made by the hybridoma method. Human myeloma and mouse-human heteromyeloma cell lines for the production of human monoclonal antibodies have been described, for example, by Kozbor J. Immunol., 133: 3001 (1984); Brodeur et al., Monoclonal Antibody Production Techniques and Applications, Marcel Dekker, Inc., New York, pp. 51-63 (1987); and Boerner et al., J. Immunol., 147: 86 (1991).

It is possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggermann et al., Year in Immuno., 7:33 (1993); and Duchosal et al. Nature 355:258 (1992).

Gene shuffling can also be used to derive human antibodies from non-human, e.g. rodent, antibodies, where the human antibody has similar affinities and specificities to the starting non-human antibody. According to this method, which is also called "epitope imprinting", either the heavy or light chain variable region of a non-human antibody fragment obtained by phage display techniques as described herein is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone, i.e. the epitope governs (imprints) the choice of the human chain partner. When the process is repeated in order to replace the remaining non-human chain, a human antibody is obtained (see PCT WO 93/06213 published Apr. 1, 1993). Unlike traditional humanization of non-human antibodies by CDR grafting, this technique provides completely human antibodies, which have no FR or CDR residues of non-human origin.

(v) Antibody Fragments

Antibody fragments may be generated by traditional means, such as enzymatic digestion, or by recombinant techniques. In certain circumstances there are advantages of using antibody fragments, rather than whole antibodies. The smaller size of the fragments allows for rapid clearance, and may lead to improved access to solid tumors. For a review of certain antibody fragments, see Hudson et al. *Nat. Med.* 9:129-134 (2003).

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science,* 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology* 10:163-167 (1992)). According to another approach, F(ab')$_2$ fragments can be isolated directly from recombinant host cell culture. Fab and F(ab')$_2$ fragment with increased in vivo half-life comprising salvage receptor binding epitope residues are described in U.S. Pat. No. 5,869,046. Other techniques for the production of antibody fragments will be apparent to the skilled practitioner. In certain embodiments, an antibody is a single chain Fv fragment (scFv). See WO 93/16185; U.S. Pat. Nos. 5,571,894; and 5,587,458. Fv and scFv are the only species with intact combining sites that are devoid of constant regions; thus, they may be suitable for reduced nonspecific binding during in vivo use. scFv fusion proteins may be constructed to yield fusion of an effector protein at either the amino or the carboxy terminus of an scFv. See *Antibody Engineering*, ed. Borrebaeck, supra. The antibody fragment may also be a "linear antibody", e.g., as described in U.S. Pat. No. 5,641,870, for example. Such linear antibodies may be monospecific or bispecific.

(vi) Multispecific Antibodies

Multispecific antibodies have binding specificities for at least two different epitopes, where the epitopes are usually from different antigens. While such molecules normally will only bind two different epitopes (i.e. bispecific antibodies, BsAbs), antibodies with additional specificities such as trispecific antibodies are encompassed by this expression when used herein. Bispecific antibodies can be prepared as full length antibodies or antibody fragments (e.g. F(ab')$_2$ bispecific antibodies).

Methods for making bispecific antibodies are known in the art. Traditional production of full length bispecific antibodies is based on the coexpression of two immunoglobulin heavy chain-light chain pairs, where the two chains have different specificities (Millstein et al., *Nature,* 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.,* 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is typical to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology,* 121:210 (1986).

According to another approach described in WO96/27011, the interface between a pair of antibody molecules can be engineered to maximize the percentage of heterodimers which are recovered from recombinant cell culture. One interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al, *J. Immunol*, 152:5368 (1994).

Antibodies with more than two valencies are contemplated. For example, trispecific antibodies can be prepared. Tuft et al., *J. Immunol.* 147: 60 (1991).

(vii) Single-Domain Antibodies

In some embodiments, an antibody of the invention is a single-domain antibody. A single-domain antibody is a single polypeptide chain comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516). In one embodiment, a single-domain antibody consists of all or a portion of the heavy chain variable domain of an antibody.

(viii) Antibody Variants

In some embodiments, amino acid sequence modification(s) of the antibodies described herein are contemplated. For example, it may be desirable to improve the binding affinity and/or other biological properties of the antibody. Amino acid sequence variants of the antibody may be prepared by introducing appropriate changes into the nucleotide sequence encoding the antibody, or by peptide synthesis. Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired characteristics. The amino acid alterations may be introduced in the subject antibody amino acid sequence at the time that sequence is made.

(ix) Antibody Derivatives

The antibodies of the invention can be further modified to contain additional nonproteinaceous moieties that are known in the art and readily available. In certain embodiments, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

(x) Vectors, Host Cells, Recombinant Methods

Antibodies may also be produced using recombinant methods. For recombinant production of an anti-antigen antibody, nucleic acid encoding the antibody is isolated and inserted into a replicable vector for further cloning (amplification of the DNA) or for expression. DNA encoding the antibody may be readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

(a) Signal Sequence Component

An antibody of the invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (e.g., cleaved by a signal peptidase) by the host cell. For prokaryotic host cells that do not recognize and process a native antibody signal sequence, the signal sequence is substituted by a prokaryotic signal sequence selected, for example, from the group of the alkaline phosphatase, penicillinase, 1pp, or heat-stable enterotoxin II leaders. For yeast secretion the native signal sequence may be substituted by, e.g., the yeast invertase leader, a factor leader (including *Saccharomyces* and *Kluyveromyces* α-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available.

(b) Origin of Replication

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter.

(c) Selection of Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up antibody-encoding nucleic acid, such as DHFR, glutamine synthetase (GS), thymidine kinase, metallothionein-I and -II, preferably primate metallothionein genes, adenosine deaminase, ornithine decarboxylase, etc.

For example, cells transformed with the DHFR gene are identified by culturing the transformants in a culture medium containing methotrexate (Mtx), a competitive antagonist of DHFR. Under these conditions, the DHFR gene is amplified along with any other co-transformed nucleic acid. A Chinese hamster ovary (CHO) cell line deficient in endogenous DHFR activity (e.g., ATCC CRL-9096) may be used.

Alternatively, cells transformed with the GS gene are identified by culturing the transformants in a culture medium containing L-methionine sulfoximine (Msx), an inhibitor of GS. Under these conditions, the GS gene is amplified along with any other co-transformed nucleic acid. The GS selection/amplification system may be used in combination with the DHFR selection/amplification system described above.

Alternatively, host cells (particularly wild-type hosts that contain endogenous DHFR) transformed or co-transformed with DNA sequences encoding an antibody of interest, wild-type DHFR gene, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., *Nature*, 282:39 (1979)). The trp1 gene provides a selection marker for a mutant strain of yeast lacking the ability to grow in tryptophan, for example, ATCC No. 44076 or PEP4-1. Jones, *Genetics*, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K. lactis*. Van den Berg, *Bio/Technology*, 8:135 (1990). Stable multi-copy expression vectors for secretion of mature recombinant human serum albumin by industrial strains of *Kluyveromyces* have also been disclosed. Fleer et al., *Bio/Technology*, 9:968-975 (1991).

(d) Promoter Component

Expression and cloning vectors generally contain a promoter that is recognized by the host organism and is operably linked to nucleic acid encoding an antibody. Promoters suitable for use with prokaryotic hosts include the phoA promoter, β-lactamase and lactose promoter systems, alkaline phosphatase promoter, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding an antibody.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoter sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Antibody transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus, Simian Virus 40 (SV40), or from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982) on expression of human β-interferon cDNA in mouse cells under the control of a thymidine kinase promoter from herpes simplex virus. Alternatively, the Rous Sarcoma Virus long terminal repeat can be used as the promoter.

(e) Enhancer Element Component

Transcription of a DNA encoding an antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the antibody-encoding sequence, but is preferably located at a site 5' from the promoter.

(f) Transcription Terminator Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding antibody. One useful transcription termination component is the bovine growth hormone polyadenylation region. See WO94/11026 and the expression vector disclosed therein.

(g) Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as Escherichia, e.g., E. coli, Enterobacter, Erwinia, Klebsiella, Proteus, Salmonella, e.g., Salmonella typhimurium, Serratia, e.g., Serratia marcescans, and Shigella, as well as Bacilli such as B. subtilis and B. licheniformis (e.g., B. licheniformis 41P disclosed in DD 266,710 published 12 Apr. 1989), Pseudomonas such as P. aeruginosa, and Streptomyces. One preferred E. coli cloning host is E. coli 294 (ATCC 31,446), although other strains such as E. coli B, E. coli X1776 (ATCC 31,537), and E. coli W3110 (ATCC 27,325) are suitable. These examples are illustrative rather than limiting.

Full length antibody, antibody fusion proteins, and antibody fragments can be produced in bacteria, in particular when glycosylation and Fc effector function are not needed, such as when the therapeutic antibody is conjugated to a cytotoxic agent (e.g., a toxin) that by itself shows effectiveness in tumor cell destruction. Full length antibodies have greater half-life in circulation. Production in E. coli is faster and more cost efficient. For expression of antibody fragments and polypeptides in bacteria, see, e.g., U.S. Pat. No. 5,648,237 (Carter et. al.), U.S. Pat. No. 5,789,199 (Joly et al.), U.S. Pat. No. 5,840,523 (Simmons et al.), which describes translation initiation region (TIR) and signal sequences for optimizing expression and secretion. See also Charlton, Methods in Molecular Biology, Vol. 248, B. K. C. Lo, ed., Humana Press, Totowa, N.J., pp. 245-254 (2003), describing expression of antibody fragments in E. coli. After expression, the antibody may be isolated from the E. coli cell paste in a soluble fraction and can be purified through, e.g., a protein A or G column depending on the isotype. Final purification can be carried out similar to the process for purifying antibody expressed e.g., in CHO cells.

In addition to prokaryotes, eukaryotic microbes such as filamentous fungi or yeast are suitable cloning or expression hosts for antibody-encoding vectors. Saccharomyces cerevisiae, or common baker's yeast, is the most commonly used among lower eukaryotic host microorganisms. However, a number of other genera, species, and strains are commonly available and useful herein, such as Schizosaccharomyces pombe; Kluyveromyces hosts such as, e.g., K. lactis, K. fragilis (ATCC 12,424), K. bulgaricus (ATCC 16,045), K. wickeramii (ATCC 24,178), K. waltii (ATCC 56,500), K. drosophilarum (ATCC 36,906), K. thermotolerans, and K. marxianus; yarrowia (EP 402,226); Pichia pastoris (EP 183,070); Candida; Trichoderma reesia (EP 244,234); Neurospora crassa; Schwanniomyces such as Schwanniomyces occidentalis; and filamentous fungi such as, e.g., Neurospora, Penicillium, Tolypocladium, and Aspergillus hosts such as A. nidulans and A. niger. For a review discussing the use of yeasts and filamentous fungi for the production of therapeutic proteins, see, e.g., Gerngross, Nat. Biotech. 22:1409-1414 (2004).

Certain fungi and yeast strains may be selected in which glycosylation pathways have been "humanized," resulting in the production of an antibody with a partially or fully human glycosylation pattern. See, e.g., Li et al., Nat. Biotech. 24:210-215 (2006) (describing humanization of the glycosylation pathway in Pichia pastoris); and Gerngross et al., supra.

Suitable host cells for the expression of glycosylated antibody are also derived from multicellular organisms (invertebrates and vertebrates). Examples of invertebrate cells include plant and insect cells. Numerous baculoviral strains and variants and corresponding permissive insect host cells from hosts such as Spodoptera frugiperda (caterpillar), Aedes aegypti (mosquito), Aedes albopictus (mosquito), Drosophila melanogaster (fruitfly), and Bombyx mori have been identified. A variety of viral strains for transfection are publicly available, e.g., the L-1 variant of Autographa californica NPV and the Bm-5 strain of Bombyx

*mori* NPV, and such viruses may be used as the virus herein according to the invention, particularly for transfection of *Spodoptera frugiperda* cells.

Plant cell cultures of cotton, corn, potato, soybean, *petunia*, tomato, duckweed (Leninaceae), alfalfa (*M. truncatula*), and tobacco can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may be used as hosts, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2). Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as NS0 and Sp2/0. For a review of certain mammalian host cell lines suitable for antibody production, see, e.g., Yazaki and Wu, *Methods in Molecular Biology*, 248:255-268 (2003).

Host cells are transformed with the above-described expression or cloning vectors for antibody production and cultured in conventional nutrient media modified as appropriate for inducing promoters, selecting transformants, or amplifying the genes encoding the desired sequences.

(h) Culturing Host Cells

The host cells used to produce an antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(xi) Purification of Antibody

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., *Bio/Technology* 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, hydrophobic interaction chromatography, gel electrophoresis, dialysis, and affinity chromatography, with affinity chromatography being among one of the typically preferred purification steps. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

In general, various methodologies for preparing antibodies for use in research, testing, and clinical are well-established in the art, consistent with the above-described methodologies and/or as deemed appropriate by one skilled in the art for a particular antibody of interest.

B. Selecting Biologically Active Antibodies

Antibodies produced as described above may be subjected to one or more "biological activity" assays to select an antibody with beneficial properties from a therapeutic perspective. The antibody may be screened for its ability to bind the antigen against which it was raised. For example, for an anti-DR5 antibody (e.g., drozitumab), the antigen binding properties of the antibody can be evaluated in an assay that detects the ability to bind to a death receptor 5 (DR5).

In another embodiment, the affinity of the antibody may be determined by saturation binding; ELISA; and/or competition assays (e.g. RIA's), for example.

Also, the antibody may be subjected to other biological activity assays, e.g., in order to evaluate its effectiveness as a therapeutic. Such assays are known in the art and depend on the target antigen and intended use for the antibody.

To screen for antibodies which bind to a particular epitope on the antigen of interest, a routine cross-blocking assay such as that described in *Antibodies, A Laboratory Manual*, Cold Spring Harbor Laboratory, Ed Harlow and David Lane (1988), can be performed. Alternatively, epitope mapping, e.g. as described in Champe et al., *J. Biol. Chem.* 270:1388-1394 (1995), can be performed to determine whether the antibody binds an epitope of interest.

C. Preparation of the Formulations

Provided herein are formulations comprising a polysorbate and a cyclodextrin that have reduced polysorbate degradation. In some embodiments the cyclodextrin is 2-hydroxypropyl-β-cyclodextrin (HP-β-CD). In some embodiments, the cyclodextrin is 2-hydroxypropyl-α-cyclodextrin (HP-α-CD), 2-hydroxypropyl-γ-cyclodextrin (HP-γ-CD). In some embodiments, the cyclodextrin is β-cyclodextrin (β-CD). In some embodiments the cyclodextrin is sulfobutyl ether β-cyclodextrin (SBE-β-CD). In some embodiments, the cyclodextrin is α-cyclodextrin (α-CD). In some embodiments, the cyclodextrin is γ-cyclodextrin (γ-CD). In some embodiments, the formulation comprises a polysorbate and a polyvinylpyrrolidone (PVP) and has reduced polysorbate degradation. In some embodiments, the formulation further comprises a polypeptide. In some embodiments, the polysorbate is in the range of about 0.001% to about 15% or any range between these values. In certain embodiments the polysorbate is in the range of about 0.001% to about 0.4%, 0.01% to about 0.4%, about 0.01% to about 0.3%, about 0.01% to about 0.2%, about 0.01% to about 0.1%. In some embodiments, the formulation comprises about 0.001%, about 0.005% about 0.01%, about 0.02% about 0.03%, about 0.04%, about 0.05%, about 0.06%, about 0.07%, about 0.08%, about 0.09%, about 0.1%, about 0.4%, about 1%, about 5%, or about 15% polysorbate. In some embodiments the polysorbate is polysorbate 20. In some embodiments the polysorbate is polysorbate 40. In some embodiments the polysorbate is polysorbate 60. In some embodiments, the polysorbate is polysorbate 80.

In some embodiments polyvinalpyrrolidone is a class of polymeric molecules made from made from the monomer N-vinylpyrrolidone. In some embodiments the polyvinylpyrrolidone (PVP) is Povidone (soluble PVP). In some embodiments the PVP is Povidone K12 (Approximate MW: 2.5 kDa). In some embodiments the PVP is Povidone K15 (Approximate MW: 8 kDa). In some embodiments the PVP is Povidone K17 (Approximate MW: 10 kDa). In some embodiments the PVP is Povidone K25 (Approximate MW: 30 kDa). In some embodiments the PVP is Povidone K30 (Approximate MW: 50 kDa). In some embodiments the PVP is Povidone K60 (Approximate MW: 400 kDa). In some embodiments the PVP is Povidone K90 (Approximate MW: 1,000 kDa). In some embodiments the PVP is Povidone K120 (3,000 kDa). In some embodiments the PVP is Crospovidone (insoluble PVP). In some embodiments the PVP is Copovidone.

In some embodiments the cyclodextrin is in the range of about 0.5% to about 30%. In some embodiments the cyclodextrin is in the range of about 1% to about 25%, or about 5% to about 20%, or about 10% to about 15%. In further embodiments, the cyclodextrin is at a concentration of about 0.5%, about 1%, about 5%, about 10%, about 15%, about 20%, about 25%, or about 30%. In some embodiments the PVP is in the range of about 0.5% to about 30%.

In some embodiments, the w/w ratio of cyclodextrin to polysorbate in the formulation is greater than about 37.5:1. In some embodiments, the w/w ratio of cyclodextrin to polysorbate in the formulation is greater than about 50:1, greater than about 100:1, greater than about 150:1, greater than about 250:1, greater than about 750:1, greater than about 1000:1, or greater than about 3000:1. In some embodiments, the w/w ratio of cyclodextrin to polysorbate is not between 67:1 and 1000:1. In some embodiments, the w/w ratio of PVP to polysorbate in the formulation is greater than about 37.5:1.

In some embodiments, the aqueous formulation comprises a polypeptide at a concentration in the range from about 10 mg/mL to about 250 mg/mL or any range between these values. In some embodiments, the polypeptide is at a concentration greater than about 250 mg/mL. In some embodiments, the polypeptide is at a concentration in the range from any one of about 10 mg/mL to 250 mg/mL, 50 mg/mL to 250 mg/mL, 100 mg/mL to 250 mg/mL, 150 mg/mL to 250 mg/mL, 200 mg/mL to 250 mg/mL, 10 mg/mL to 200 mg/mL, 50 mg/mL to 200 mg/mL, 100 mg/mL to 200 mg/mL, 150 mg/mL to 200 mg/mL, 10 mg/mL to 150 mg/mL, 50 mg/mL to 150 mg/mL, 100 mg/mL to 150 mg/mL, 10 mg/mL to 100 mg/mL, 50 mg/mL to 100 mg/mL, 10 mg/mL to 50 mg/mL or any range between these ranges.

In some embodiments, the aqueous formulation comprises an antibody. In some embodiments, the antibody is directed to (VEGF); CD20; ox-LDL; ox-ApoB100; renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; receptors for hormones or growth factors; protein A or D; rheumatoid factors; a neurotrophic factor such as bone-derived neurotrophic factor (BDNF), neurotrophin-3, -4, -5, or -6 (NT-3, NT4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des (1-3)-IGF-I (brain IGF-I), insulin-like growth factor binding proteins; CD proteins such as CD3, CD4, CD8, CD19 and CD20; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrns such as CD11a, CD11b, CD11c, CD18, an ICAM, VLA-4 and VCAM; a tumor associated antigen such as HER2, HER3 or HER4 receptor; and fragments of any of the above-listed polypeptides. In some embodiments, the antibody is not an anti-CD20 antibody. In some embodiments, the formulation does not comprise an anti-CD20 antibody and 0.2% polysorbate (e.g., polysorbate 80). In some embodiments, the formulation does not comprise 10% HP-γcyclodextrin and 0.03% polysorbate 20. In some embodiments, the formulation does not comprise an anti-CD20 antibody, 10% HP-γcyclodextrin and 0.03% polysorbate 20.

In some embodiments, the aqueous formulation further comprises one or more excipients selected from the group consisting of a stabilizer, a buffer, a surfactant, and a tonicity agent. An aqueous formulation of the invention can be prepared in a pH-buffered solution. The buffer of this invention has a pH in the range from about pH 4.5 to about 9.0. In certain embodiments the pH is in the range from about pH 4.5 to about 7.0, in the range from about pH 4.5 to about 6.5, in the range from about pH 4.5 to about 6.0, in the range from about pH 4.5 to about 5.5, in the range from about pH 4.5 to about 5.0, in the range from about pH 5.0 to about 7.0, in the range from about pH 5.5 to about 7.0, in the range from about pH 5.7 to about 6.8, in the range from about pH 5.8 to about 6.5, in the range from about pH 5.9 to about 6.5, in the range from about pH 6.0 to about 6.5, or in the range from about pH 6.2 to about 6.5. In certain embodiments, the liquid formulation has a pH in the range of about 4.7 to about 5.2, in the range of about 5.0 to about 6.0, or in the range of about 5.2 to about 5.8. In certain embodiments of the invention, the liquid formulation has a pH of 6.2 or about 6.2. In certain embodiments of the invention, the liquid formulation has a pH of 6.0 or about 6.0.

Examples of buffers that will control the pH within this range include organic and inorganic acids and salts thereof. For example, acetate (e.g., histidine acetate, arginine acetate, sodium acetate), succinate (e.g., histidine succinate, arginine succinate, sodium succinate), gluconate, phosphate, fumarate, oxalate, lactate, citrate, and combinations thereof. The buffer concentration can be from about 1 mM to about 600 mM, depending, for example, on the buffer and the desired isotonicity of the formulation.

Additional surfactants can optionally be added to the aqueous formulation. Exemplary surfactants include non-ionic surfactants such as poloxamers (e.g. poloxamer 188, etc.). The amount of surfactant added is such that it reduces aggregation of the formulated antibody and/or minimizes the formation of particulates in the formulation and/or reduces adsorption. For example, the surfactant may be present in the formulation in an amount from about 0.001% to about 0.5%, from about 0.005% to about 0.2%, from about 0.01% to about 0.1%, or from about 0.02% to about 0.06%, or about 0.03% to about 0.05%. In certain embodiments, the surfactant is present in the formulation in an amount of 0.04% or about 0.04%. In certain embodiments, the surfactant is present in the formulation in an amount of 0.02% or about 0.02%. In one embodiment, the formulation does not comprise a surfactant.

Tonicity agents, sometimes known as "stabilizers" are present to adjust or maintain the tonicity of liquid in a composition. When used with large, charged biomolecules such as proteins and antibodies, they are often termed "stabilizers" because they can interact with the charged groups of the amino acid side chains, thereby lessening the potential for inter- and intra-molecular interactions. Tonicity agents can be present in any amount between 0.1% to 25% by weight, or more preferably between 1% to 5% by weight, taking into account the relative amounts of the other ingredients. Preferred tonicity agents include polyhydric sugar alcohols, preferably trihydric or higher sugar alcohols, such as glycerin, erythritol, arabitol, xylitol, sorbitol and mannitol.

In some embodiments, the formulation is for in vivo administration. In some embodiments, the formulation is sterile. The formulation may be rendered sterile by filtration through sterile filtration membranes. The therapeutic formulations herein generally are placed into a container having a sterile access port, for example, an intravenous solution bag or vial having a stopper pierceable by a hypodermic injection needle. The route of administration is in accordance with known and accepted methods, such as by single or multiple bolus or infusion over a long period of time in a suitable manner, e.g., injection or infusion by subcutaneous, intravenous, intraperitoneal, intramuscular, intraarterial, intralesional or intraarticular routes, topical administration, inhalation or by sustained release or extended-release means.

The aqueous formulations provided by the invention comprise a polypeptide, a polysorbate, and a cyclodextrin and show enhanced polysorbate stability after a period of storage. In one embodiment, the polysorbate stability is expressed as a relative percent of polysorbate remaining in a formulation after a period of storage. For example if a formulation that contains 0.1% polysorbate initially and contains 0.09% polysorbate after a period of storage, 10% of the polysorbate has been degraded. In a further embodiment, the amount of polysorbate in a solution is determined by reverse phase ultra-performance liquid chromatography using evaporative light scattering detection (RP-ELSD) (Kim, J & Qiu, J. 2014, *Analytica Chimica Acta* 806:144-151). In some embodiments the concentration of polysorbate in a sample is determined by comparing the sample results to a standard curve generated using different polysorbate concentrations.

In some embodiments, less than 5% of the polysorbate has degraded after the formulation is stored at about 1° C. to about 10° C. for about six months, at least about 12 months, at least about 18 months, at least about 24 months, at least about 30 months, at least about 36 months, at least about 42 months, or at least about 48 months. In some embodiments, less than 5% of the polysorbate has degraded after the formulation is stored at about 2° C. to about 8° C. for at least about six months, at least about 12 months, at least about 18 months, at least about 24 months, at least about 30 months, at least about 36 months, at least about 42 months, or at least about 48 months. In some embodiments, less than 5% of the polysorbate has degraded after the formulation is stored at about 4° C. to about 6° C. for at least about six months, at least about 12 months, at least about 18 months, at least about 24 months, at least about 30 months, at least about 36 months, at least about 42 months, or at least about 48 months.

In some embodiments, less than 1% of the polysorbate has degraded after the formulation is stored at about 1° C. to about 10° C. for at least about six months, at least about 12 months, at least about 18 months, at least about 24 months, at least about 30 months, at least about 36 months, at least about 42 months, or at least about 48 months. In some embodiments, less than 1% of the polysorbate has degraded after the formulation is stored at about 2° C. to about 8° C. for at least about six months, at least about 12 months, at least about 18 months, at least about 24 months, at least about 30 months, at least about 36 months, at least about 42 months, or at least about 48 months. In some embodiments, less than 1% of the polysorbate has degraded after the formulation is stored at about 4° C. to about 6° C. for at least about six months, at least about 12 months, at least about 18 months, at least about 24 months, at least about 30 months, at least about 36 months, at least about 42 months, or at least about 48 months.

In some embodiments, less than 0.1% of the polysorbate has degraded after the formulation is stored at about 1° C. to about 10° C. for at least about six months, at least about 12 months, at least about 18 months, at least about 24 months, at least about 30 months, at least about 36 months, at least about 42 months, or at least about 48 months. In some embodiments, less than 0.1% of the polysorbate has degraded after the formulation is stored at about 2° C. to about 8° C. for at least about six months, at least about 12 months, at least about 18 months, at least about 24 months, at least about 30 months, at least about 36 months, at least about 42 months, or at least about 48 months. In some embodiments, less than 0.1% of the polysorbate has degraded after the formulation is stored at about 4° C. to about 6° C. for at least about six months, at least about 12 months, at least about 18 months, at least about 24 months, at least about 30 months, at least about 36 months, at least about 42 months, or at least about 48 months.

In some embodiments, less than 5% of the polysorbate has degraded after the formulation is stored at about 22° C. to about 28° C. for at least about one month, at least about two months, at least about three months, at least about four months, at least about five months, at least about six months, at least about seven months, at least about eight months, at least about nine months, at least about ten months, at least about eleven months, or at least about twelve months. In some embodiments, less than 1% of the polysorbate has degraded after the formulation is stored at about 22° C. to about 28° C. for at least about one month, at least about two months, at least about three months, at least about four months, at least about five months, at least about six months, at least about seven months, at least about eight months, at least about nine months, at least about ten months, at least about eleven months, or at least about twelve months. In some embodiments, less than 0.1% of the polysorbate has degraded after the formulation is stored at about 22° C. to about 28° C. for at least about one month, at least about two months, at least about three months, at least about four months, at least about five months, at least about six months, at least about seven months, at least about eight months, at least about nine months, at least about ten months, at least about eleven months, or at least about twelve months.

In some embodiments, less than 5% of the polysorbate has degraded after the formulation is stored at about −15° C. to about −25° C. for at least about 12 months, at least about 18 months, at least about 24 months, at least about 30 months, at least about 36 months, at least about 42 months, at least about 48 months, at least about 54 months, at least about 60 months, at least about 66 months, or at least about 72 months. In some embodiments, less than 1% of the polysorbate has degraded after the formulation is stored at about −15° C. to about −25° C. for at least about 12 months, at least about 18 months, at least about 24 months, at least about 30 months, at least about 36 months, at least about 42 months, at least about 48 months, at least about 54 months, at least about 60 months, at least about 66 months, or at least about 72 months. In some embodiments, less than 0.1% of the polysorbate has degraded after the formulation is stored at about −15° C. to about −25° C. for at least about 12 months, at least about 18 months, at least about 24 months, at least about 30 months, at least about 36 months, at least about 42 months, or at least about 48 months, at least about 54 months, at least about 60 months, at least about 66 months, or at least about 72 months.

In some embodiments, the formulation is stored at about −8° C. to about −80° C. In some embodiments, the formulation is stored at about −20° C., −40° C., −70° C., or −80° C.

The formulations provided by the invention herein are effective for reducing polysorbate degradation products such as visible and sub-visible particles. In one embodiment, visible particles are observed by placing the sample in a glass vial and rotating the sample in the presence of a Tyndall light. In one embodiment, subvisible particles are analyzed using a high accuracy (HIAC) particle counter. In some embodiments, a HIAC 9703 particle counter equipped with an HRDL-150 detector and a 1 mL syringe can be used. In some embodiments, performance of the instrument can be verified with NIST-traceable 2 µm Polystyrene bead standards at 3000 counts/mL before each measurement session. In some embodiments, the HIAC instrument may be configured to a 10 mL/min flow rate, 0.1 mL tare volume, and 0.4 mL sample volume. In particular embodiments, the samples may be analyzed using 4 runs of 0.4 mL sips, with the first run of each sample was discarded to prevent measurement error due to sample carryover. Filter sizes of 2, 5, 10, 15, and 25 µm can be used for analysis.

In some embodiments, the formulation has less than about 10,000, about 5,000, about 1,000, about 500, about 250, about 150, about 100, about 50, or about 25 particles greater than 1.4µ in diameter per mL. In some embodiments, the formulation has less than about 10,000, about 5,000, about 1,000, about 500, about 250, about 150, about 100, about 50, or about 25 particles greater than 2µ in diameter per mL. In some embodiments, the formulation has less than about 1250, about 150, about 100, about 50, about 25, about 20, about 15, about 10, about 5, about 4, about 3, about 2, or about 1 particles greater than 5µ in diameter per mL. In some embodiments, the formulation has less than about 250, about 150, about 100, about 50, about 25, about 20, about 15, about 10, about 5, about 4, about 3, about 2, or about 1 particles 10µ in diameter per mL. In some embodiments, the formulation has less than about 250, about 150, about 100, about 50, about 25, about 20, about 15, about 10, about 5, about 4, about 3, about 2, or about 1 particles greater than 15µ in diameter per mL. In some embodiments, the formulation has less than about 250, about 150, about 100, about 50, about 25, about 20, about 15, about 10, about 5, about 4, about 3, about 2, or about 1 particles greater than 25µ in diameter per mL.

III. Administration of Formulations

The aqueous formulation is administered to a mammal in need of treatment with the protein (e.g., an antibody), preferably a human, in accord with known methods, such as intravenous administration as a bolus or by continuous infusion over a period of time, by intramuscular, intraperitoneal, intracerobrospinal, subcutaneous, intravitreal, intraarticular, intrasynovial, intrathecal, ocular, oral, topical, or inhalation routes. In one embodiment, the aqueous formulation is administered to the mammal by intravenous administration. For such purposes, the formulation may be injected using a syringe or via an IV line, for example. In one embodiment, the liquid formulation is administered to the mammal by subcutaneous administration.

The appropriate dosage ("therapeutically effective amount") of the protein will depend, for example, on the condition to be treated, the severity and course of the condition, whether the protein is administered for preventive or therapeutic purposes, previous therapy, the patient's clinical history and response to the protein, the type of protein used, and the discretion of the attending physician. The protein is suitably administered to the patient at one time or over a series of treatments and may be administered to the patient at any time from diagnosis onwards. The protein may be administered as the sole treatment or in conjunction with other drugs or therapies useful in treating the condition in question. As used herein the term "treatment" refers to both therapeutic treatment and prophylactic or preventative measures. Those in need of treatment include those already with the disorder as well as those in which the disorder is to be prevented. As used herein a "disorder" is any condition that would benefit from treatment including, but not limited to, chronic and acute disorders or diseases including those pathological conditions which predispose the mammal to the disorder in question.

In a pharmacological sense, in the context of the invention, a "therapeutically effective amount" of a protein (e.g., an antibody) refers to an amount effective in the prevention or treatment of a disorder for the treatment of which the antibody is effective. As a general proposition, the therapeutically effective amount of the protein administered will be in the range of about 0.1 to about 50 mg/kg of patient body weight whether by one or more administrations, with the typical range of protein used being about 0.3 to about 20 mg/kg, preferably about 0.3 to about 15 mg/kg, administered daily, for example. However, other dosage regimens may be useful. For example, a protein can be administered at a dose of about 100 or 400 mg every 1, 2, 3, or 4 weeks or is administered a dose of about 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 15.0, or 20.0 mg/kg every 1, 2, 3, or 4 weeks. The dose may be administered as a single dose or as multiple doses (e.g., 2 or 3 doses), such as infusions. The progress of this therapy is easily monitored by conventional techniques.

IV. Methods of Reducing Polysorbate Degradation

Provided herein are methods of reducing polysorbate degradation in an aqueous formulation containing polysorbate, comprising adding a cyclodextrin to the formulation. Also provided herein are methods of reducing the amount of visible and sub-visible particles in an aqueous solution containing polysorbate, comprising adding a cyclodextrin to the formulation. The invention also includes a method to disaggregate and solubilize polysorbate degradation products in an aqueous solution comprising adding a cyclodextrin to the formulation. In some embodiments, the formulation further comprises a polypeptide, a nucleic acid, a lipid and/or a carbohydrate.

Provided herein are methods of reducing polysorbate in an aqueous formulation comprising polyvinylpryrrolidone (PVP) and polysorbate. Also provided herein are methods of reducing the amount of visible and sub-visible particles in an aqueous solution containing polysorbate, comprising adding PVP to the formulation. The invention also includes a method to disaggregate and solubilize polysorbate degradation products in an aqueous solution comprising adding PVP to the formulation. In some embodiments, the formulation further comprises a polypeptide, a nucleic acid, a lipid and/or a carbohydrate.

In some embodiments, the polysorbate is in the range of about 0.001% to about 0.4% or any range between these values. In certain embodiments the polysorbate is in the range of about 0.001% to about 0.4%, about 0.01% to about 0.4%, about 0.01% to about 0.3%, about 0.01% to about 0.2%, or about 0.01% to about 0.1%. In some embodiments, the formulation comprises about 0.001%, about 0.005%, about 0.01%, about 0.02% about 0.03% about 0.04%, about 0.05%, about 0.06%, about 0.07%, about 0.08%, about 0.09%, about 0.1%, or about, 0.4% polysorbate. In some embodiments the polysorbate is polysorbate 20. In some embodiments the polysorbate is polysorbate 40. In some embodiments the polysorbate is polysorbate 60. In some embodiments, the polysorbate is polysorbate 80.

In some embodiments the cyclodextrin is added to a concentration of about 0.5% to about 30%. In some embodiments the cyclodextrin is in the range of about 1% to about 25%, about 5% to about 20%, or about 10% to about 15%. In further embodiments, the cyclodextrin is added to a concentration of about 0.5%, about 1%, about 5%, about 10%, about 15%, about 20%, about 25%, or about 30%. In some embodiments PVP is added to a concentration of about 0.5% to about 30%.

In some embodiments, the formulation does not comprise 10% HP-γcyclodextrin and 0.03% polysorbate 20. In some embodiments, the formulation does not comprise an anti-CD20 antibody, 10% HP-γcyclodextrin and 0.03% polysorbate 20.

In some embodiments, the resulting w/w ratio of cyclodextrin to polysorbate in the formulation is greater than about 37.5:1. In some embodiments, the resulting w/w ratio of cyclodextrin to polysorbate in the formulation is greater than about 50:1, greater than about 100:1, greater than about 150:1, greater than about 250:1, greater than about 750 to 1, greater than about 1000:1, or greater than about 3000:1. In some embodiments, the resulting w/w ratio of cyclodextrin to polysorbate in the formulation is not in between 67:1 and 1000:1. In some embodiments, the resulting w/w ratio of PVP to polysorbate in the formulation is greater than about 37.5:1. In some embodiments, the resulting ratio of PVP to polysorbate in the formulation is 250:1.

In some embodiments the cyclodextrin is 2-hydroxypropyl-β-cyclodextrin (HP-β-CD). In some embodiments, the cyclodextrin is 2-hydroxypropyl-α-cyclodextrin (HP-α-CD), 2-hydroxypropyl-γ-cyclodextrin (HP-γ-CD). In some embodiments, the cyclodextrin is sulfobutyl ether β-cyclodextrin (SBE-β-CD) In some embodiments, the cyclodextrin is β-cyclodextrin (β-CD). In some embodiments, the cyclodextrin is α-cyclodextrin (α-CD). In some embodiments, the cyclodextrin is γ-cyclodextrin (γ-CD).

In some embodiments, the aqueous formulation comprises a polypeptide at a concentration in the range from 10 mg/mL to 250 mg/mL. In some embodiments, the polypeptide is at a concentration at above 250 mg/mL. In some embodiments, the polypeptide is at a concentration in the range from 30 mg/mL to 150 mg/mL, 50 mg/mL to 150 mg/mL, or 100 to 150 mg/mL.

In some embodiments, the aqueous formulation comprises an antibody. In some embodiments, the antibody is directed to (VEGF); CD20; ox-LDL; ox-ApoB100; renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; receptors for hormones or growth factors; protein A or D; rheumatoid factors; a neurotrophic factor such as bone-derived neurotrophic factor (BDNF), neurotrophin-3, -4, -5, or -6 (NT-3, NT4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des (1-3)-IGF-I (brain IGF-I), insulin-like growth factor binding proteins; CD proteins such as CD3, CD4, CD8, CD19 and CD20; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrns such as CD11a, CD11b, CD11c, CD18, an ICAM, VLA-4 and VCAM; a tumor associated antigen such as HER2, HER3 or HER4 receptor; and fragments of any of the above-listed polypeptides. In some embodiments, the antibody is not an anti-CD20 antibody.

In some embodiments, one or more excipients selected from the group consisting of a stabilizer, a buffer, a surfactant, and a tonicity agent are included in the aqueous formulation. The method the invention can be carried out prepared in a pH-buffered solution. The buffer of this invention has a pH in the range from about pH 4.5 to about 9.0. In certain embodiments the pH is in the range from about pH 4.5 to about 7.0, in the range from about pH 4.5 to about 6.6, in the range from about pH 4.5 to about 6.0, in the range from about pH 4.5 to about 5.5, in the range from about pH 4.5 to about 5.0, in the range from about pH 5.0 to about 7.0, in the range from about pH 5.5 to about 7.0, in the range from about pH 5.7 to about 6.8, in the range from about pH 5.8 to about 6.5, in the range from about pH 5.9 to about 6.5, in the range from about pH 6.0 to about 6.5, or in the range from about pH 6.2 to about 6.5. In certain embodiments, the liquid formulation has a pH in the range of about 4.7 to about 5.2, in the range of about 5.0 to about 6.0, or in the range of about 5.2 to about 5.8. In certain embodiments of the invention, the liquid formulation has a pH of 6.2 or about 6.2. In certain embodiments of the invention, the liquid formulation has a pH of 6.0 or about 6.0.

Examples of buffers that will control the pH within this range include organic and inorganic acids and salts thereof. For example, acetate (e.g., histidine acetate, arginine acetate, sodium acetate), succinate (e.g., histidine succinate, arginine succinate, sodium succinate), gluconate, phosphate, fumarate, oxalate, lactate, citrate, and combinations thereof. The buffer concentration can be from about 1 mM to about 600 mM, depending, for example, on the buffer and the desired isotonicity of the formulation.

Additional surfactants can optionally be added to the aqueous formulation. Exemplary surfactants include non-ionic surfactants such as poloxamers (e.g. poloxamer 188, etc.). The amount of surfactant added is such that it reduces aggregation of the formulated antibody and/or minimizes the formation of particulates in the formulation and/or reduces adsorption. For example, the surfactant may be present in the formulation in an amount from about 0.001% to about 0.5%, from about 0.005% to about 0.2%, from about 0.01% to about 0.1%, from about 0.02% to about 0.06%, or from about 0.03% to about 0.05%. In certain embodiments, the surfactant is present in the formulation in an amount of 0.04% or about 0.04%. In certain embodiments, the surfactant is present in the formulation in an amount of 0.02% or about 0.02%. In one embodiment, the formulation does not comprise a surfactant.

The method may involve the use of tonicity agents, sometimes known as "stabilizers" to adjust or maintain the tonicity the aqueous formulation. When used with large, charged biomolecules such as proteins and antibodies, they are often termed "stabilizers" because they can interact with the charged groups of the amino acid side chains, thereby lessening the potential for inter- and intra-molecular interactions. Tonicity agents can be present in any amount between 0.1% to 25% by weight, or more preferably between 1% to 5% by weight, taking into account the relative amounts of the other ingredients. Preferred tonicity agents include polyhydric sugar alcohols, preferably trihydric or higher sugar alcohols, such as glycerin, erythritol, arabitol, xylitol, sorbitol and mannitol.

In some embodiments, the method results in less than 5% of the polysorbate being degraded after the formulation is stored at about 1° C. to about 10° C. for at least about six months, at least about 12 months, at least about 18 months, at least about 24 months, at least about 30 months, at least about 36 months, at least about 42 months, or at least about 48 months. In some embodiments, less than 5% of the polysorbate has degraded after the formulation is stored at about 2° C. to about 8° C. for at least about six months at least about 12 months, at least about 18 months, at least about 24 months, at least about 30 months, at least about 36 months, at least about 42 months, or at least about 48 months. In some embodiments, the method results in less than 5% of the polysorbate being degraded after the formulation is stored at about 4° C. to about 6° C. for at least about six months, at least about 12 months, at least about 18 months, at least about 24 months, at least about 30 months, at least about 36 months, at least about 42 months, or at least about 48 months.

In some embodiments, the method results in less than 1% of the polysorbate being degraded after the formulation is stored at about 1° C. to about 10° C. for at least about six months, at least about 12 months, at least about 18 months, at least about 24 months, at least about 30 months, at least about 36 months, at least about 42 months, or at least about 48 months. In some embodiments, the method results in less than 1% of the polysorbate being degraded after the formulation is stored at about 2° C. to about 8° C. for at least about six months, at least about 12 months, at least about 18 months, at least about 24 months, at least about 30 months, at least about 36 months, at least about 42 months, or at least about 48 months. In some embodiments, the method results in less than 1% of the polysorbate has degraded after the formulation is stored at about 4° C. to about 6° C. for at least about six months, at least about 12 months, at least about 18 months, at least about 24 months, at least about 30 months, at least about 36 months, at least about 42 months, or at least about 48 months.

In some embodiments, the method results in less than 0.1% of the polysorbate being degraded after the formulation is stored at about 1° C. to about 10° C. for at least about six months, at least about 12 months, at least about 18 months, at least about 24 months, at least about 30 months, at least about 36 months, at least about 42 months, or at least about 48 months. In some embodiments, the method results in than 0.1% of the polysorbate being degraded after the formulation is stored at about 2° C. to about 8° C. for at least about six months, at least about 12 months, at least about 18 months, at least about 24 months, at least about 30 months, at least about 36 months, at least about 42 months, or at least about 48 months. In some embodiments, the method results in less than 0.1% of the polysorbate being degraded after the formulation is stored at about 4° C. to about 6° C. for at least about six months, at least about 12 months, at least about 18 months, at least about 24 months, at least about 30 months, at least about 36 months, at least about 42 months, or at least about 48 months.

In some embodiments, the method results in less than 5% of the polysorbate being degraded after the formulation is stored at about 22° C. to about 28° C. for at least about one month, at least about two months, at least about three months, at least about four months, at least about five months, at least about six months, at least about seven months, at least about eight months, at least about nine months, at least about ten months, at least about eleven months, or at least about twelve months. In some embodiments, the method results in less than 1% of the polysorbate being degraded after the formulation is stored at about 22° C. to about 28° C. for at least about one month, at least about two months, at least about three months, at least about four months, at least about five months, at least about six months, at least about seven months, at least about eight months, at least about nine months, at least about ten months, at least about eleven months, or at least about twelve months. In some embodiments, the method results in less than 0.1% of the polysorbate being degraded after the formulation is stored at about 22° C. to about 28° C. for at least about one month, at least about two months, at least about three months, at least about four months, at least about five months, at least about six months, at least about seven months, at least about eight months, at least about nine months, at least about ten months, at least about eleven months, or at least about twelve months.

In some embodiments, less than 5% of the polysorbate has degraded after the formulation is stored at about −15° C. to about −25° C. for at least about 12 months, at least about 18 months, at least about 24 months, at least about 30 months, at least about 36 months, at least about 42 months, at least about 48 months, at least about 54 months, at least about 60 months, at least about 66 months, or at least about 72 months. In some embodiments, the method results in less than 1% of the polysorbate being degraded after the formulation is stored at about −15° C. to about −25° C. for at least about 12 months, at least about 18 months, at least about 24 months, at least about 30 months, at least about 36 months, at least about 42 months, at least about 48 months, at least about 54 months, at least about 60 months, at least about 66 months, or at least about 72 months. In some embodiments, the method results in less than 0.1% of the polysorbate being degraded after the formulation is stored at about −15° C. to about −25° C. for at least about 12 months, at least about 18 months, at least about 24 months, at least about 30 months, at least about 36 months, at least about 42 months, or at least about 48 months, at least about 54 months, at least about 60 months, at least about 66 months, or at least about 72 months.

The methods provided by the invention are effective in reducing the number of sub-visible and visible particles. In some embodiments, less than about 10,000, about 5,000, about 1,000, about 500, about 250, about 150, about 100, about 50, or about 25 particles greater than 1.4µ in diameter are formed per mL. In some embodiments, the formulation has less than about 10,000, about 5,000, about 1,000, about 500, about 250, about 150, about 100, about 50, or about 25 particles greater than 2µ in diameter per mL. In some embodiments, less than about 1250, about 150, about 100, about 50, about 25, about 20, about 15, about 10, about 5, about 4, about 3, about 2, or about 1 particles greater than 5µ in diameter are formed per mL. In some embodiments, less than about 250, about 150, about 100, about 50, about 25, about 20, about 15, about 10, about 5, about 4, about 3, about 2, or about 1 particles 10µ in diameter are formed per mL. In some embodiments, less than about 250, about 150, about 100, about 50, about 25, about 20, about 15, about 10, about 5, about 4, about 3, about 2, or about 1 particles greater than 15µ in diameter are formed per mL. In some embodiments, less than about 250, about 150, about 100, about 50, about 25, about 20, about 15, about 10, about 5, about 4, about 3, about 2, or about 1 particles greater than 25µ in diameter are formed per mL.

A method of resolubilizing polysorbate degradation products in a formulation is also provided herein. In some embodiments, the number of particles greater than 1.4µ present in the formulation is reduced by 100, 1000, 2000, 5000, or 10000 fold after adding polysorbate. In some embodiments, the number of particles greater than 2µ in diameter present in the formulation is reduced by 100, 1000, 2000, 5000, or 10000 fold after adding polysorbate. In some embodiments, the number of particles greater than 5µ in diameter present in the formulation is reduced by 100, 1000, 2000, 5000, or 10000 fold after adding polysorbate. In some embodiments, the number of particles greater than 10µ in diameter present in the formulation is reduced by 100, 1000, 2000, 5000, or 10000 fold after adding polysorbate. In some embodiments, the number of particles greater than 15µ in diameter present in the formulation is reduced by 100, 1000, 2000, 5000, or 10000 fold after adding polysorbate. In some embodiments, the number of particles greater than 25µ in diameter present in the formulation is reduced by 100, 1000, 2000, 5000, or 10000 fold after adding polysorbate.

V. Articles of Manufacture

In another embodiment of the invention, an article of manufacture is provided comprising a container which holds the liquid formulation of the invention and optionally provides instructions for its use. Suitable containers include, for example, bottles, vials and syringes. The container may be formed from a variety of materials such as glass or plastic. An exemplary container is a 3-20 cc single use glass vial. Alternatively, for a multidose formulation, the container may be 3-100 cc glass vial. The container holds the formulation and the label on, or associated with, the container may indicate directions for use. The article of manufacture may further include other materials desirable from a commercial and user standpoint, including other buffers, diluents, filters, needles, syringes, and package inserts with instructions for use.

VI. Kits

In another embodiment of the invention, kits for reducing polysorbate degradation are provided. In some embodiments, the invention provides kit for use in reducing polysorbate degradation by the methods described herein. In some embodiments, a kit comprising any of the formulations provided herein is provided. In one embodiment, such kits comprise a container of an aqueous formulation of therapeutic peptide or antibody and a solution of a cyclodextrin that can be added to the aqueous formulation, wherein the ratio of cyclodextrin to polysorbate is greater than 37.5:1. In one embodiment, such kits comprise a container of an aqueous formulation of therapeutic peptide or antibody and a solution of polyvinylpyrrolidone (PVP) that can be added to the aqueous formulation, wherein the ratio of PVP to polysorbate is greater than 37.5:1.

The specification is considered to be sufficient to enable one skilled in the art to practice the invention. Various modifications of the invention in addition to those shown and described herein will become apparent to those skilled in the art from the foregoing description and fall within the scope of the appended claims. All publications, patents, and patent applications cited herein are hereby incorporated by reference in their entirety for all purposes.

EXAMPLES

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

Materials and Methods

Materials

Hydroxypropyl-β-cyclodextrin (HP-β-CD) as was obtained from Ashland Inc. (Ashland, Ky.) as Cavitron W7 HP5 Pharma. Sulfobutylether-β-cyclodextrin (SBE-β-CD) was obtained from Ligand Pharmaceuticals (La Jolla, Calif.) as Captisol. Hydroxypropyl-alpha-cyclodextrin (HP-α-CD), hydroxypropyl-γ-cyclodextrin (HP-γ-CD), polyethylene glycol (PEG 1500), and methionine were obtained from Sigma Aldrich (St. Louis, Mo.). Polyvinylpyrrolidone (PVP) was obtained as KollidonPovidone K-157 from Spectrum Chemical (Gardena, Calif.). Polysorbate 20 (PS20) was obtained from Croda Inc. (New Castle, Del.). Porcine pancreatic lipase (PPL), lipoprotein lipase from *Burkholderia* sp. (LPL), *Candida antarctica* lipase B (CALB), rabbit liver esterase (RLE), and 2,2'-Azobis(2-methylpropionamidine) dihydrochloride (AAPH) were obtained from Sigma Aldrich Inc. (St. Louis, Mo.).

Determination of Subvisible Particle Counts by HIAC

Subvisible particles were measured using a HIAC 9703 particle counter equipped with an HRDL-150 detector and a 1 mL syringe. Performance of the instrument was verified with NIST-traceable 2 μm Polystyrene bead standards at 3000 counts/mL before each measurement session. The HIAC instrument was configured to a 10 mL/min flow rate, 0.1 mL tare volume, and 0.4 mL sample volume. The samples were analyzed using 4 runs of 0.4 mL sips, with the first run of each sample was discarded to prevent measurement error due to sample carryover. Results were reported as the average values for 1.4, 2, 5, 10, 15, and 25, 50 μm analysis filter sizes.

Determination of Polysorbate Concentration

Polysorbate concentration was determined using reverse phase ultra-performance liquid chromatography using evaporative light scattering detection (RP-ELSD). Samples were analyzed using an Agilent 1100 series high performance liquid chromatography system (HPLC) fitted with a Waters Oasis MAX cartridge column (20×2.1 mm, 30 μm particle size). The HPLC system was set up with a switching valve directing column flow-through to either waste or a Varian 380-LC evaporative light scattering detector set to 100° C. The mobile phases consisted of 2% formic acid in water (Pump A) and 2% formic acid in isopropanol (Pump B). The pump gradient was isocratic at 10% pump B during equilibration, linear to 20% pump B for 1 minute, isocratic at 20% pump B for 2.4 minutes, linear to 100% pump B for 0.1 minutes, isocratic at 100% pump B for 1.1 minutes, linear to 10% pump B for 0.1 minutes, and finally isocratic at 10% pump B for 1.9 minutes. The switching valve directed column flow-through to waste at the beginning of every injection, and then directed flow to the detector after 2.4 minutes until the end of the gradient. In order to quantitate the PS20 concentration, a standard curve was generated by injecting 20 μL of solutions containing between 0% w/v and 0.4% w/v PS20. For excipients which affected the migration time of PS20 through the column, PS20 standard curve solutions containing the relevant excipient were included in the analysis to facilitate accurate quantitation.

Visible Particle Imaging by Seidenader

Vials were inspected for visible particulates using a Seidenader V90-T visual inspection unit (Markt Schwaben, Germany) with vial carriage tilted to 60 degrees. Visible particle inspection of samples was performed by placing the glass vials in the holder and rotating in the presence of a Tyndall light directed through the bottom of the vial. Pre-rotation (i.e., fast rotation) was first performed to agitate the liquids, suspend, and circulate particles. Following rotation and illumination, the particles are in motion and the light causes reflections of the particles that make them visible (i.e., Tyndall effect). Visible particles were then observed using a magnifying lens. Videos and photographs of visible particles were obtained using a Samsung (seoul, South Korea) Galaxy device.

Determination of Turbidity

Turbidity was determined using UV spectroscopy. The UV absorbance of each sample was measured by recording the absorbance at 279 nm and 320 nm in a quartz cuvette with 1-cm path length on an Agilent 8453 spectrophotometer using Chemstation software (Agilent Technologies, Santa Clara, Calif.).

Determination of Protein Concentration

Protein concentration was measured by The UV absorbance of each sample was measured by recording the average absorbance between 340 nm and 360 nm in a quartz cuvette with 1-cm path length on an Agilent 8453 spectrophotometer using Chemstation software (Agilent Technologies, Santa Clara, Calif.). The UV concentration determination was calculated by using the experimentally determined absorptivities for each protein. The measurements were blanked against the appropriate buffers.

Example 1: Oxidative Degradation of Polysorbate

The ability of cyclodextrins to inhibit oxidative PS20 degradation was evaluated using 2,2'-Azobisisobutyramidinium (AAPH), which has been shown previously to degrade PS20 (Borisov et al., J. Pharm. Sci. 104:1005-1018 (2015)). To evaluate the ability of cyclodextrins to inhibit oxidation of PS20, samples containing either 15% (w/v) HP-β-CD or 15% (w/v) sucrose were compared to control samples (without any additional excipients). Polysorbate 20 degradation was determined by RP-ELSD for samples oxidized with 5 mM AAPH at 40° C. for 24 hours containing no excipient (control), 15% (w/v) sucrose, and 15% (w/v) HP-β-CD.

As shown in FIG. 1, the data demonstrate that both HP-β-CD and sucrose decrease the amount of PS20 degradation. Following incubation with AAPH, a decrease of 17.9 in relative percent PS20 degradation was observed in the control sample. Conversely, smaller decreases of 9.8 and 3.6 in percent PS20 degradation were observed for samples containing 15% (w/v) sucrose and HP-β-CD, respectively.

Example 2: Inhibitory Effects of HP-β-CD on the Enzymatic Degradation of Polysorbate 20

The effect of 15% HP-β-CD on the enzymatic degradation of PS20 was measured. Samples of 0.02% PS20 in pH 5.5 buffer containing either no additional excipient, 15% Sucrose, or 15% HP-β-CD were digested with each of the enzymes porcine pancreatic lipase (PPL), lipoprotein lipase (LPL), *Candida Antarctica* lipase (CALB,) and rabbit liver esterase (RLE) at room temperature. PPL samples were digested with 15 μg/mL enzyme for 4.5 hours. LPL samples were digested with 70 μg/mL enzyme for 5 hours. CALB samples were digested with 0.1 mg/mL immobilized enzyme for 1 hour. RLE samples were digested with 15 μg/mL enzyme for 5 hours. All digestions were conducted at room temperature.

PPL digestion was stopped by heat inactivation in an 85° C. water bath for 30 minutes. LPL and RLE digestion could not be stopped by heat inactivation, so the samples were analyzed immediately for PS20 content. CALB digestion was stopped by filtering out the immobilized enzyme beads. In order to permit particle formation, CALB samples were placed at 5° C. overnight. RLE and LPL samples were frozen at −20° C. overnight to impede enzymatic activity and were then thawed over ice immediately prior to particle analysis.

As described above, all samples were analyzed for PS20 content by high performance liquid chromatography (Agilent 1100 series) with an inline evaporative light scattering detector (Varian 380-LC series). Visible particle inspection was conducted on a Seidenader visual inspection instrument. Subvisible particle analysis was conducted on a HIAC 9703 particle counter.

Figure 2:
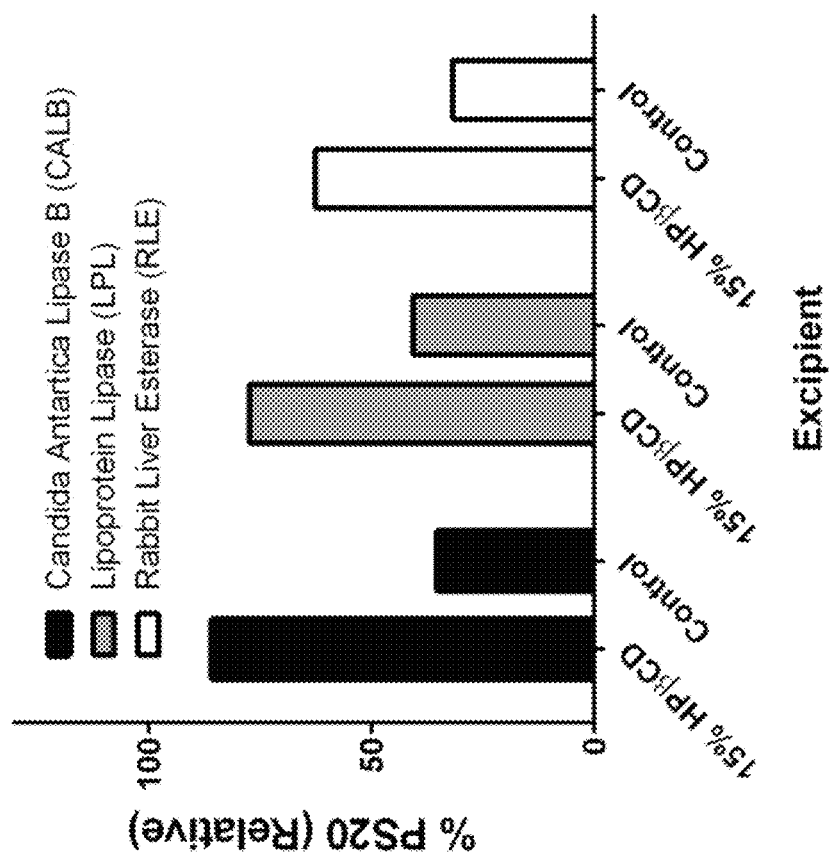
FIG. 2 displays the average (n=3) relative percent of PS20 determined by RP-ELSD for samples digested using *Candida Antarctica* Lipase B (black), Lipoprotein Lipase (grey), and Rabbit Liver Esterase (white) enzymes in protein-free samples containing both 0.02% (w/v) PS20 with 0 and 15% (w/v) HP-β-CD.

Samples treated with CALB, RLE, and LPL showed 59.2%-68.3% reductions in PS20 (FIG. 2). Conversely, samples that contain 15% of HP-β-CD showed significant inhibition of PS20 degradation. Specifically, for these samples, PS20 concentration was reduced by 14.3%-37.4% (FIG. 2 and Table 1).

TABLE 1

Enzymatic Degradation of Polysorbate 20 by CALB, LPL, and RLE

| Enzyme | HP-β-CD (% w/v) | Polysorbate 20 (Relative %) |
| --- | --- | --- |
| *Candida Antarctica* Lipase B (CALB) | 0 | 35.3% |
|  | 15 | 85.7% |
| Lipoprotein Lipase (LPL) | 0 | 40.7% |
|  | 15 | 77.5% |
| Rabbit Liver Esterase (RLE) | 0 | 31.7% |
|  | 15 | 62.7% |

Additionally, HIAC data demonstrates that 15% (w/v) HP-β-CD reduces the formation of subvisible particulates (SVP). Following enzymatic degradation with multiple enzymes (CALB, LPL, and RLE), fewer SVP/mL were observed for all particle size classifications (≥2, ≥5, ≥10, and ≥25 micron particles) when 15% (w/v) HP-β-CD was included in the sample. Similar results were obtained for LPL and RLE; however, the very small quantities of ≥10 and ≥≥25 micron particles preclude interpretation of ≥10 and ≥25 micron particle count measurements (FIGS. 3A-3D).

These findings demonstrate that HP-β-CD, a representative cyclodextrin complex, is capable of inhibiting enzymatic degradation of PS20 by multiple enzymes. Without being bound by theory, this may suggest that the primary mechanism of protection of PS20 by cyclodextrin molecules involves a direct interaction between the cyclodextrin and the polysorbate molecules.

Example 3: Inhibitory Effects of HP-β-CD on the Enzymatic Degradation of Polysorbate 80

The effect of 15% (w/v) HP-β-CD on the enzymatic degradation of PS80 was measured. Samples of 0.02% (w/v) PS80 in pH 5.5 buffer containing 0% and 15% (w/v) HP-β-CD were digested with 15 μg/mL porcine pancreatic lipase (PPL) for 5 hours at room temperature. PPL digestion was stopped by heat inactivation in an 85° C. water bath for 30 minutes.

Figure 4:
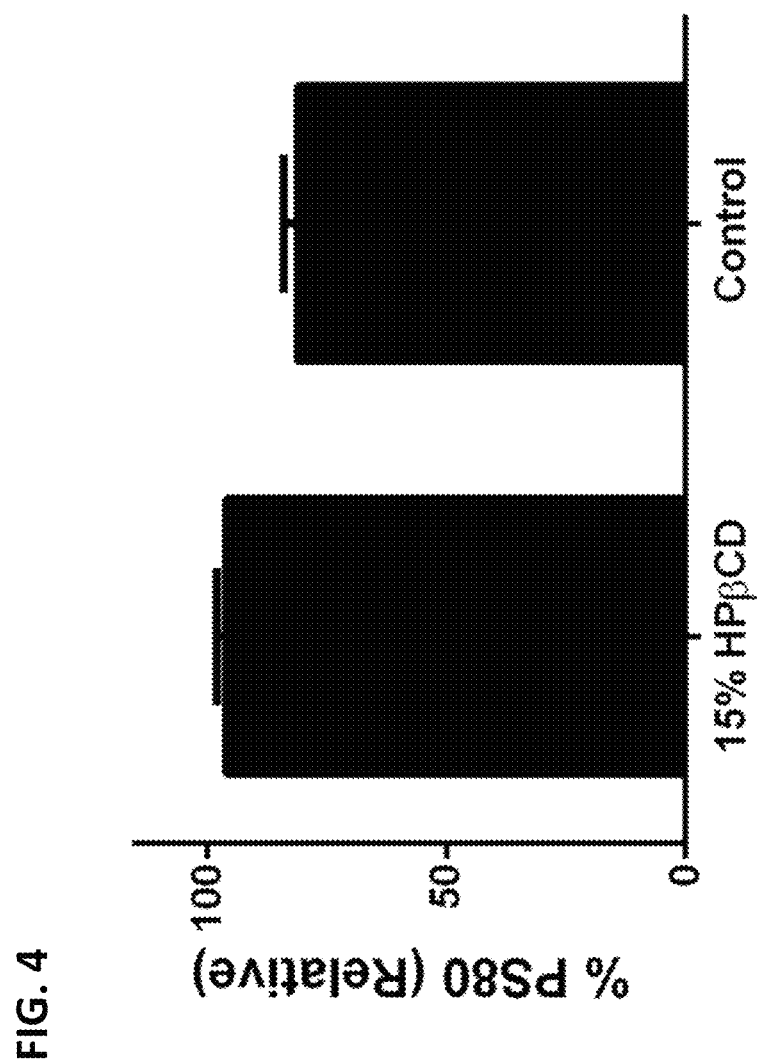
FIG. 4 displays the average (n=3) relative percent of PS80 determined by RP-ELSD for protein-free samples containing 0.02% (w/v) PS80 digested using 15 µg/mL of PPL for 5 hours at room temperature containing 0 and 15% (w/v) HP-β-CD.
Figure 5A:
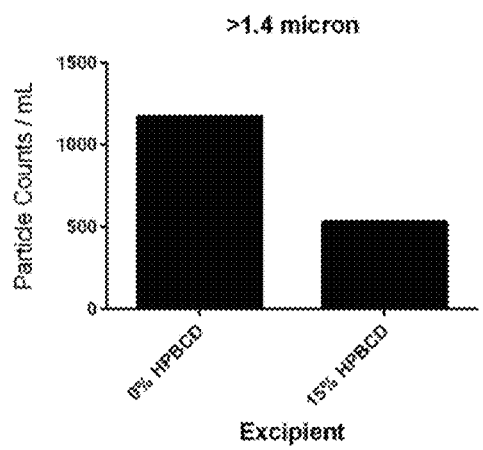
FIGS. 5A-5F display the average (n=3) (FIG. 5A) ≥1.4 µM, (FIG. 5B) ≥2 µM, (FIG. 5C) ≥5 µM, (FIG. 5D) ≥10 µM, (FIG. 5E) ≥15 µM, and (FIG. 5F) ≥25 µM subvisible particle counts per milliliter for samples digested using 15 µg/mL PPL for 5 hours at room temperature in protein-free samples containing 0.02% (w/v) PS80 and 0 and 15% (w/v) HP-β-CD.
Figure 5B:
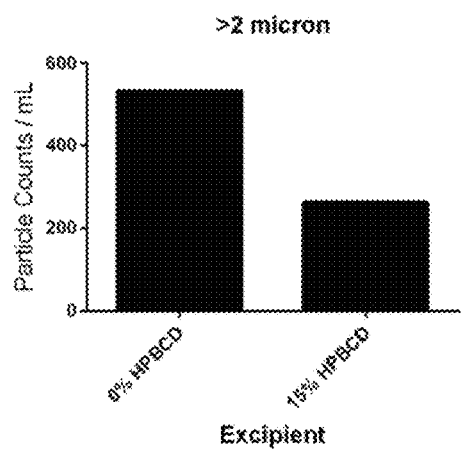
Figure 5C:
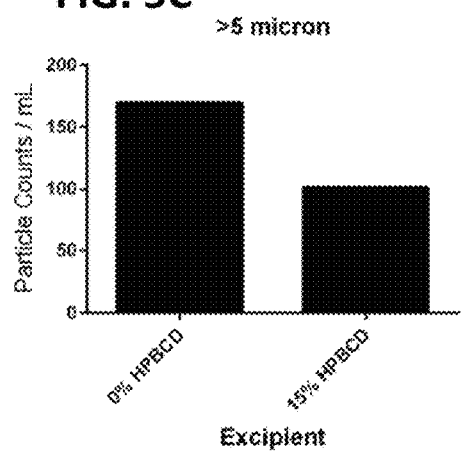
Figure 5D:
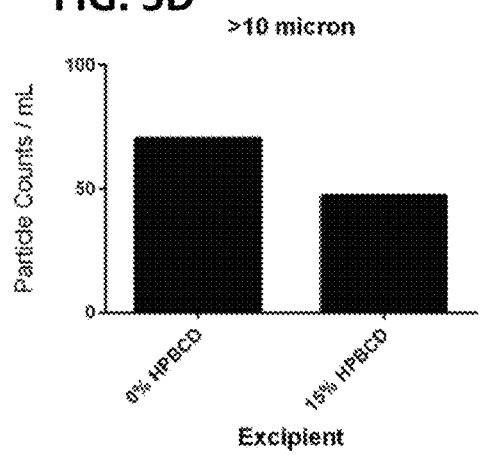
Figure 5E:
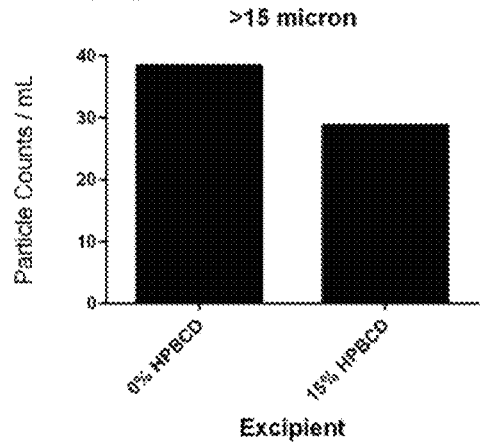
Figure 5F:
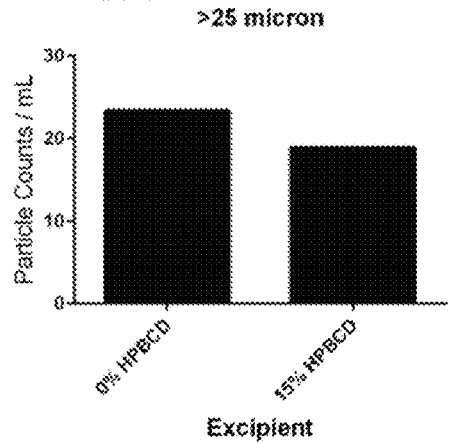

Following PPL digestion, the RP-ELSD demonstrates a decrease of approximately 19 relative percent in PS80 (FIG. 4). Conversely, a decrease of approximately 4% PS80 degradation was observed in samples that contain 15% (w/v) of HP-β-CD.

Additionally, HIAC data demonstrates that 15% (w/v) HP-β-CD reduces the average (n=3) quantity of subvisible particulates (SVP). Following enzymatic degradation with PPL, fewer SVP/mL were observed for all particle size classifications (≥1.4, ≥2, ≥5, ≥10, and ≥25 micron particles) when 15% (w/v) HP-β-CD was included in the sample (FIGS. 5A-5F).

These findings demonstrate that HP-β-CD, a representative cyclodextrin complex, is capable of inhibiting enzymatic degradation of PS80. These results suggest that the ability of cyclodextrins to reduce polysorbate degradation, reduce particle formation, and solubilize existing particles is generally applicable to the class of polysorbate molecules (e.g., PS20, PS40, PS60, PS80, etc.). Without being bound by theory, this may suggest that the primary mechanism of protection of polysorbates by cyclodextrin molecules involves a direct interaction between the cyclodextrin and conserved chemical structure subunits (e.g., fatty acids) that comprise all polysorbate molecules.

Example 4: Kinetics of Enzymatic Degradation of Polysorbate 20

To evaluate the kinetics of enzymatic PS20 degradation, samples were digested with 15 μg/mL of PPL at room temperature in protein-free samples containing 0.02% (w/v) PS20 and 15% sucrose, 15% HP-β-CD, or 15% HP-α-CD were digested using PPL incubated for 180 hours at about 25° C. As described above, all samples were analyzed for PS20 content by high performance liquid chromatography (Agilent 1100 series) with an inline evaporative light scattering detector (Varian 380-LC series). Subvisible particle analysis was conducted on a HIAC 9703 particle counter.

Figure 6:
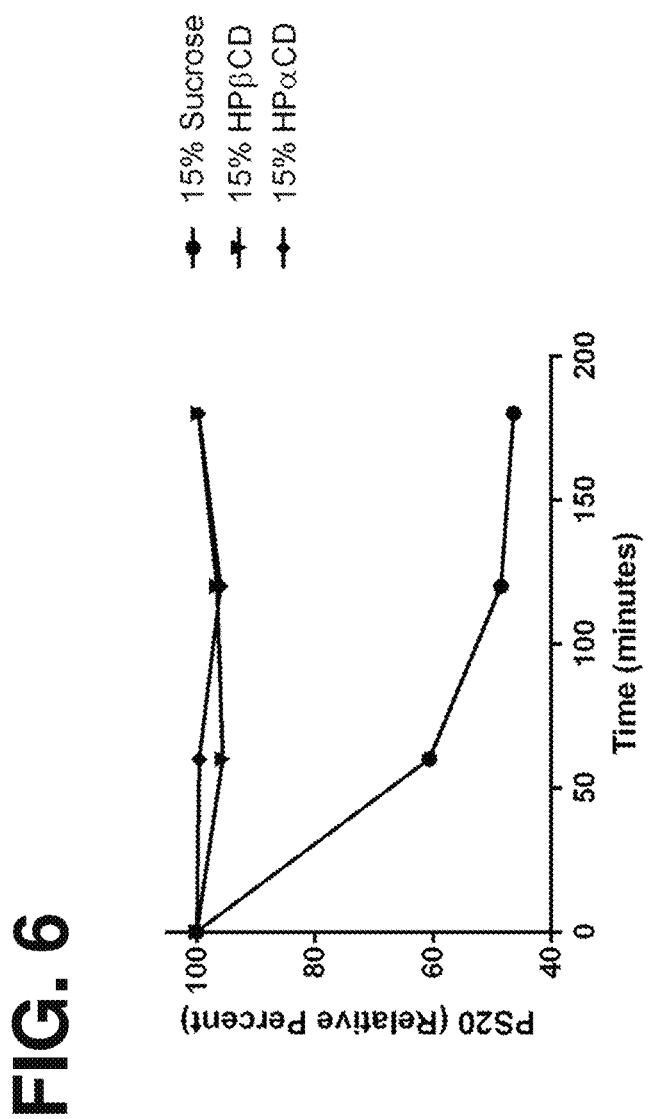
FIG. 6 displays the average (n=3) relative percent of PS20 determined by RP-ELSD for samples digested with 15 µg/mL of PPL enzyme at room temperature in protein-free samples containing 15% (w/v) of sucrose (circles), HP-α-CD (diamonds), and HP-β-CD (triangles) as a function of time.

The 15% sucrose curve in FIG. 6 shows that PS20 degradation can be described by a one phase exponential decay. The half-life is 32.91 hours with a plateau of 44% (FIG. 6). These degradation kinetics support the use of a 4.5 hour digestion model using PPL at 25° C. for 4.5 hours for subsequent studies.

Example 5: Inhibitory Effects of Cyclodextrin and Other Excipients on the Enzymatic Degradation of Polysorbate Several excipients were tested for their ability to protect PS20 against enzymatic hydrolysis including HP-α-CD, HP-β-CD, HP-γ-CD, SBE-β-CD, PVP, PEG 1500, sucrose, and methionine. Solutions of each excipient in pH 5.5 buffer were prepared containing a final concentration of 0.02% PS20 after enzyme addition. The concentration of HP-α-CD, HP-β-CD, HP-γ-CD, and SBE-β-CD in the excipient solutions was 106 mM. The methionine sample contained 10 mg/mL methionine due to solubility limitations. The remaining excipients (PVP, PEG 1500, sucrose) were added to 15% w/v to match the % w/v of HP-β-CD. Samples were digested with 15 μg/mL PPL enzyme for 4.5 hours at room temperature, followed by 30 minutes of heat inactivation at 85° C. Each sample was analyzed for PS20 concentration using high performance liquid chromatography with an inline evaporative light scattering detector. Samples were then placed at 5° C. overnight to allow for the formation of particles and were analyzed for visible and subvisible particles as described previously.

Figure 7:
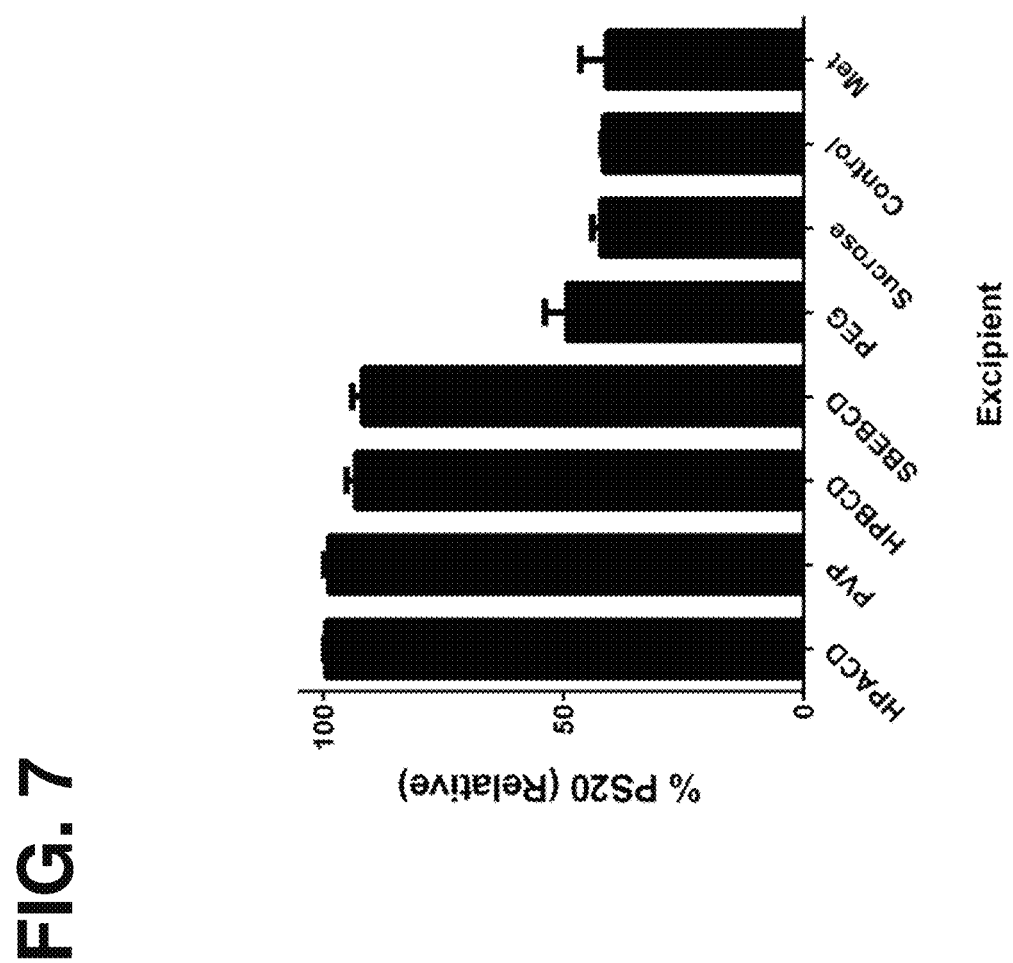
FIG. 7 displays the average (n=3) relative percent of PS20 determined by RP-ELSD for samples digested using 15 µg/mL of PPL enzyme for 4.5 hours at room temperature in protein-free samples containing 0.02% (w/v) PS20 with no excipient (control), 15% (w/v) sucrose, 1% (w/v) methionine, 15% (w/v) PEG 1500, 15% (w/v) PVP, 15% (w/v) HP-α-CD, 15% (w/v) HP-β-CD, 15% (w/v) SBE-β-CD, and 15% (w/v) HP-γ-CD.

The RP-ELSD results demonstrate that the excipient class is important for determining the extent of enzymatic PS20 degradation (FIG. 7). Following enzymatic digestion, the control sample (i.e., no excipient) had a 58 percent decrease in PS20 degradation. An equivalent decrease of 58 percent PS20 was observed for samples containing 15% (w/v) sucrose. These findings demonstrate sucrose, an acyclic disaccharide (i.e., sucrose) does not have an inhibitory effect on enzymatic PS20 degradation. The inhibitory effects of cyclodextrin cannot solely be attributed to mass dilution effects because the results demonstrate that equivalent masses of other excipients (e.g., sucrose) do not mitigate catalytic polysorbate degradation.

Similarly, samples containing methionine did not have an inhibitory effect on enzymatic PS20 degradation or SVP formation (FIGS. 7 and 8A-8D). Presumably, methionine would prevent oxidative PS20 degradation but would not prevent enzymatic PS20 degradation. Without being bound by theory, the mechanism of PS20 degradation reproduced in this experiment is likely hydrolytic and independent of oxidative PS20 degradation.

The results demonstrate that PEG has a small inhibitory effect on PS20 degradation relative to the control sample. A decrease of 51% PS20 was observed for samples containing 5% (w/v) PEG 1500.

The cyclodextrin molecules evaluated (HP-α-CD, HP-β-CD, and SBE-β-CD) all had significant inhibitory effects on enzymatic PS20 degradation and SVP formation (FIGS. 7 and 8A-8D). Interestingly, the number of sugar subunits may be important in determining the extent of inhibition by the cyclodextrin. For example, decreases of 1% and 7% PS20 were observed for HP-α-CD and HP-β-CD, respectively.

Figure 9:
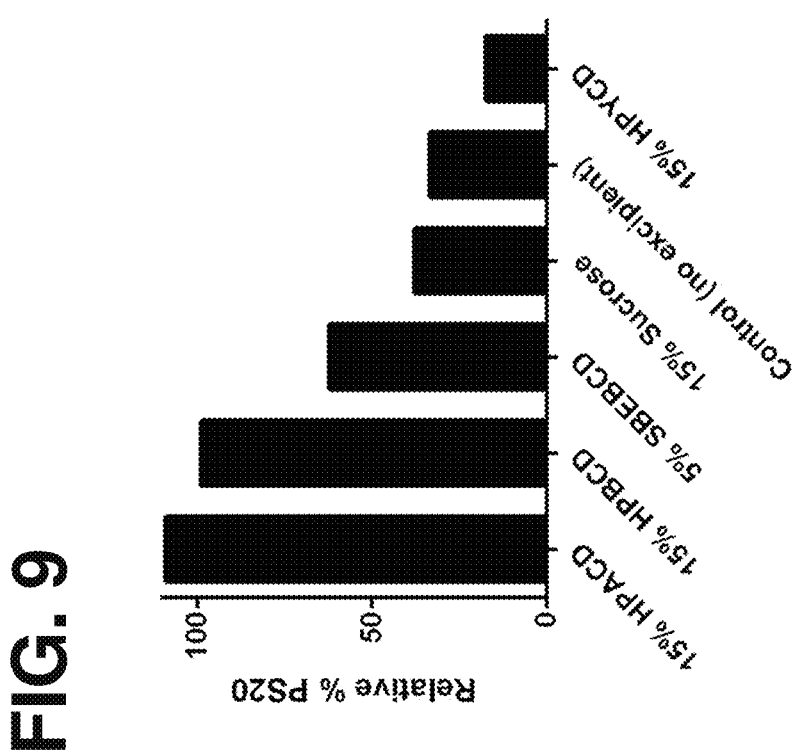
FIG. 9 displays the average (n=3) relative percent of PS20 determined by RP-ELSD for samples digested using *Candida Antarctica* Lipase B in protein-free samples containing 0.02 (w/v) PS20 with no excipient (control), 15% (w/v) SBE-β-CD, 15% (w/v) HP-α-CD, 15% (w/v) HP-β-CD, 15% (w/v) HP-γ-CD, and 15% (w/v) sucrose.
Figure 12A:
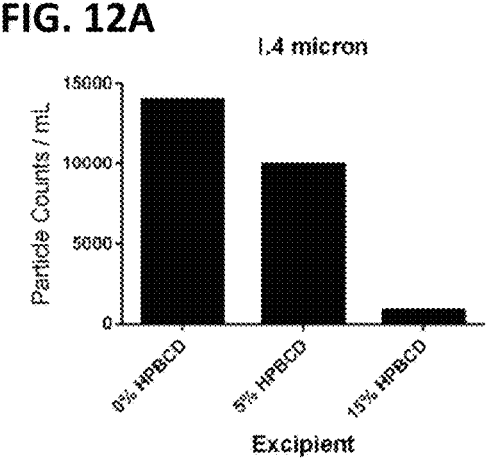
FIGS. 12A-12F display the average (n=3) (FIG. 12A) ≥1.4 µM, (FIG. 12B) ≥2 µM, (FIG. 12C) ≥5 µM, (FIG. 12D) ≥10 µM, (FIG. 12E) ≥15 µM, and (FIG. 12F) ≥25 µM subvisible particle counts determined by HIAC per milliliter in protein-free samples containing 0.02% (w/v) PS20 stored for 27 months at 5° C.
Figure 12B:
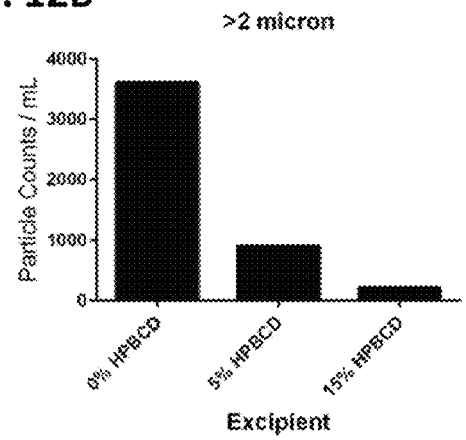
Figure 12C:
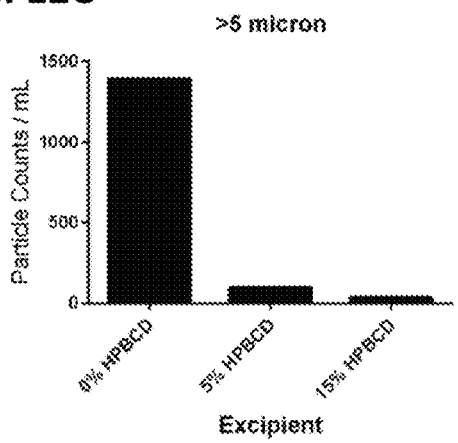
Figure 12D:
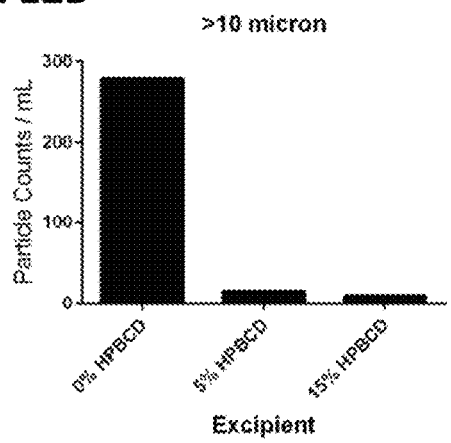
Figure 12E:
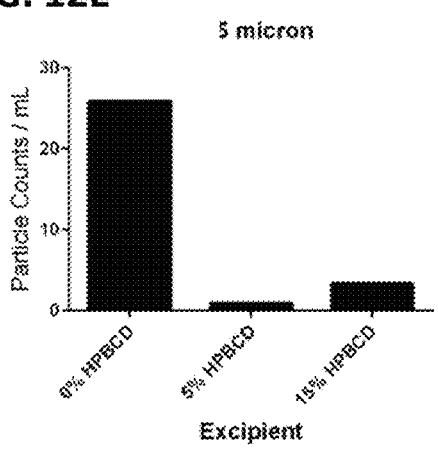
Figure 12F:
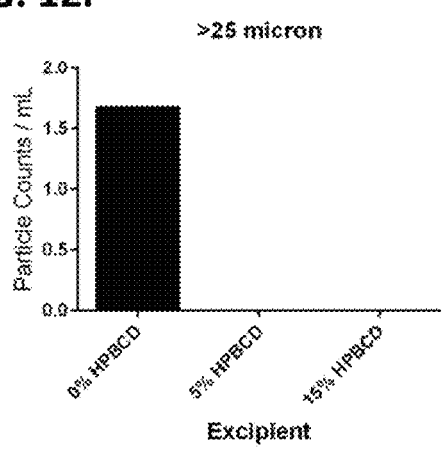

Further studies were performed to evaluate in the importance of HP-α-CD, HP-β-CD, and HP-γ-CD to further understand the importance of cyclodextrin ring size. The data shown in FIG. 9 indicate that no significant PS20 degradation was observed for samples containing HP-α-CD and HP-β-CD; conversely, ~82% in PS20 degradation was observed in samples containing 15% HP-γ-CD. Similarly, significant decreases in PS20 concentration were observed in the control samples (i.e., no excipient and 15% sucrose) (FIG. 9). These findings demonstrate that the smaller cyclodextrins HP-α-CD (Cavity Diameter: 4.7-5.2 Å; Cavity Volume: 174 Å$^3$) and HP-β-CD (Cavity Diameter: 6.0-6.5 Å; Cavity Volume: 262 Å$^3$) are more effective inhibitors of polysorbate 20 degradation than HP-γ-CD (Cavity Diameter: 7.5-8.3 Å; Cavity Volume: 472 Å$^3$).

The dimensions and volume of the cavity for each cyclodextrin may determine their effectiveness as molecular inhibitors of enzymatic PS20 degradation rather than the physicochemical properties of each cyclodextrin. Without being bound by theory, this finding suggests that the mechanism of protection may involve a host-guest complexation between the cyclodextrins and the polysorbate 20 reactive site.

Example 6: Solubilization of Visible and Subvisible Particles Related to Enzymatic Polysorbate 20 Degradation by Cyclodextrins and Other Excipients Several excipients were tested for their ability to solubilize particles produced as a result of enzymatic PS20 degradation. Solutions of concentrated HP-α-CD, HP-β-CD, HP-γ-CD, SBE-β-CD, PVP, PEG 1500, sucrose, and methionine were prepared in triplicate in pH 5.5 buffer. Particles from enzymatic PS20 degradation were prepared. Three solutions of 0.05% PS20 in pH 5.5 buffer were enzymatically degraded with 37.5 μg/mL PPL for 4.5 hours at room temperature, followed by 30 minutes of heat inactivation at 85° C. The degraded PS20 solutions were placed at 5° C. to allow for crystallization of particles.

After particle formation in the degraded PS20 solutions, the remaining sample preparation was conducted in a 5° C. cold room to prevent the PS20 derived particles from dissolving. Each degraded PS20 solution was divided into 11 aliquots and concentrated excipient was spiked into each the aliquots. The final concentration of excipient in each sample was as follows: 5% sucrose, 10 mg/mL methionine, 5% PVP, 5% PEG 1500, 15% HP-β-CD, 5% HP-β-CD, 0.5% HP-β-CD, 35.5 mM HP-α-CD, 35.5 mM HP-γ-CD, and 35.5 mM SBE-β-CD. After the addition of each excipient, samples were left at 5° C. overnight. The following day, vials were inspected for visible particles under a Seidenader visual inspection instrument. Subvisible particle counts were measured using a HIAC 9703 particle counter.

The results demonstrate that cyclodextrins (HP-α-CD, HP-β-CD, and HP-γ-CD) were able to significantly reduce the amount of SVP relative to the control and other excipient samples (FIGS. 10A and 10B). These results establish that in addition to preventing enzymatic polysorbate degradation, cyclodextrins can also solubilize the PS20 degradants that result from enzymatic digestion of polysorbate 20.

Additionally, photographs were taken immediately before and after addition of 15% (w/v) HP-β-CD. The photographs depict the solubilization of PS20-related visible particles before (FIG. 11A) and after addition of 15% (w/v) HP-β-CD (FIG. 11B). The immediate solubilization of visible particles represented in the photographs provides compelling evidence that cyclodextrins can increase the solubility of visible and subvisible particles associated with PS20 degradation.

Example 7: Solubilization of Visible and Subvisible Particles Related to Oxidative Polysorbate 20 Degradation by Cyclodextrins Different concentrations of HP-β-CD were tested for their ability to solubilize particles produced as a result of oxidative PS20 degradation. Solutions of concentrated HP-β-CD were prepared in triplicate in pH 5.5 buffer. Protein-free samples containing 0.02% (w/v) PS20 were stored for 27 months at 5° C., resulting in oxidative PS20 degradation and the formation of visible and subvisible particles related to PS20 degradation products. Each degraded PS20 solution was divided into 3 aliquots and concentrated excipient was spiked into each the aliquots. The final concentration of excipient in each sample was as follows: 0% (w/v) HP-β-CD (control), 5% (w/v) HP-β-CD, and 15% (w/v) HP-β-CD. After the HP-β-CD concentration adjustment, samples were left at 5° C. overnight. The following day, subvisible particle counts were measured using a HIAC 9703 particle counter.

The effect of 0%, 5% and 15% (w/v) concentration of HP-β-CD on resolubilization of SVP was tested. The results demonstrate that there is a significant reduction in SVP in samples containing HP-β-CD relative to the control sample (0% HP-β-CD). As shown in FIGS. 12A-12F, 15% HP-β-CD effectively resolubilizes particles greater than or equal to 1.4 microns, whereas 5% HP-β-CD effectively resolubilizes particles greater than or equal to 2 microns.

These results establish that in addition to preventing enzymatic polysorbate degradation and solubilizing the PS20 degradants that result from enzymatic digestion of polysorbate 20, cyclodextrins can also solubilize the PS20 degradation products that result from oxidative digestion of polysorbate 20.

Figure 13:
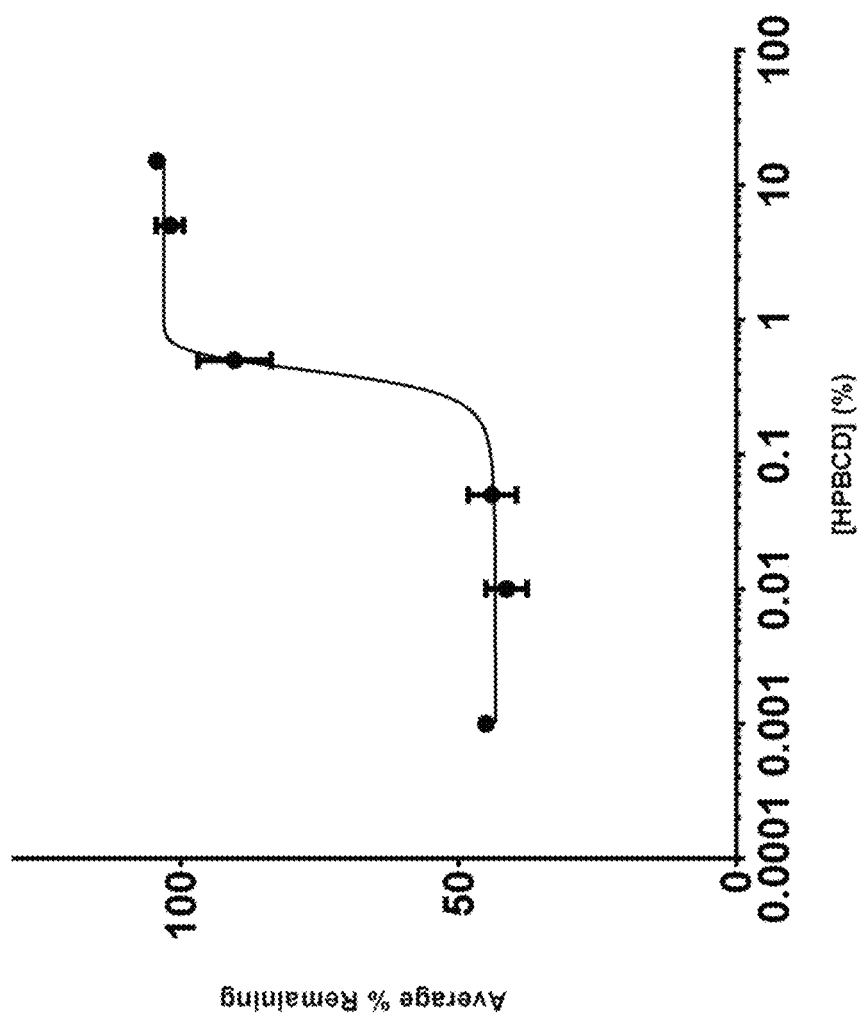
FIG. 13 displays the average (n=3) relative percent of PS20 determined by RP-ELSD for samples digested using 15 µg/mL of PPL enzyme for 4.5 hours at room temperature in protein-free samples containing 0.02% (w/v) PS20 and different amounts of HP-β-CD. Data is fit using a sigmoidal model.

Example 8: The Effects of HP-β-CD Concentration and the HP-β-CD:PS20 Ratio on PS20 Degradation To determine the effect of HP-β-CD concentration on PS20 degradation, samples containing 0.001, 0.01, 0.1, 1, 5, or 15% PS20 were digested using 15 μg/mL of PPL for 4.5 hours. As shown in FIG. 13, increasing the amount of HP-β-CD reduces PS20 degradation.

Figure 14A:
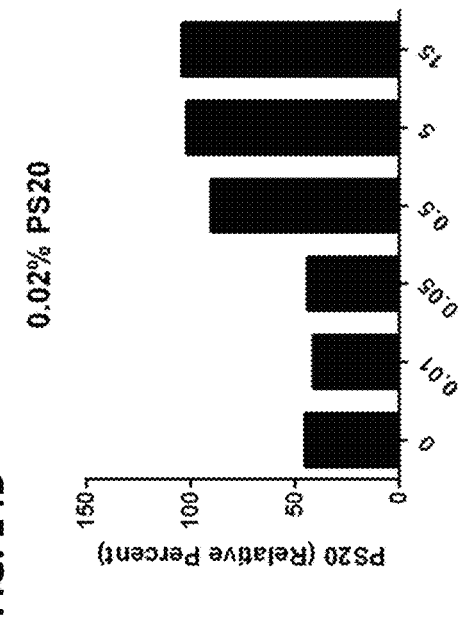
FIGS. 14A-14D display the average (n=3) relative percent of PS20 determined by RP-ELSD for samples containing (FIG. 14A) 0.005%, (FIG. 14B) 0.02%, (FIG. 14C) 0.1%, and (FIG. 14D) 0.4% PS20 digested using 15 µg/mL of PPL enzyme for 4.5 hours at room temperature in protein-free samples containing no excipient (control), 0, 0.5, 5, and 15% (w/v) HP-β-CD.
Figure 14B:
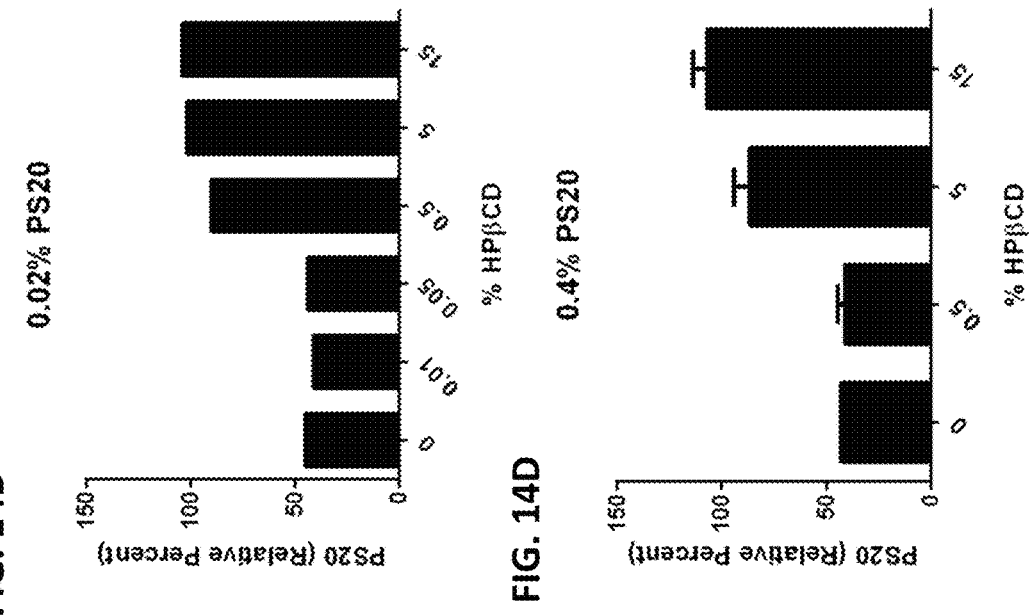

The effect of the HP-β-CD concentration at different PS20 concentrations on the enzymatic degradation of PS20 was assessed to identify optimal concentrations for inhibition of enzymatic PS20 degradation. To evaluate the dependence of PS20 degradation on HP-β-CD concentration, the PS20 content was determined using RP-ELSD for triplicate samples containing different HP-β-CD concentrations at various PS20 concentrations. Samples containing 0.005% (FIG. 14A), 0.02% (FIG. 14B), 0.1% (FIG. 14C), and 0.4% PS20 (FIG. 14D) were digested using 15 μg/mL of PPL enzyme for 4.5 hours at room temperature in protein-free samples containing no excipient (control), 0, 0.5, 5, and 15% (w/v) HP-β-CD. PPL was added to each of the treatment solutions at a ratio of 75 mg PPL per mg PS20, with an equivalent volume of buffer added to the control solutions to determine the effect of HP-β-CD to polysorbate ratio on enzymatic degradation. Digestion was stopped by heat inactivation in an 85° C. water bath for 30 minutes. Each sample was analyzed for PS20 concentration using high performance liquid chromatography with an inline evaporative light scattering detector as described above. Samples were then placed at 5° C. overnight to allow for the formation of particles and placed on ice during analysis for visible and subvisible particles as described above.

TABLE 2

| HP-β-CD to PS20 ratio | | | |
|---|---|---|---|
| [HP-β-CD]/[PS20] (wt/wt ratio) | [HP-β-CD]/[PS20] (mole ratio) | PS20 remaining (Relative %) | Std dev |
| 0 | 0 | 39.5 | |
| 0.5 | 0.4 | 41.4 | |
| 1.25 | 1.1 | 41.2 | 3.4 |
| 2.5 | 2.2 | 44.0 | |
| 5 | 4.35 | 65.3 | 21.5 |
| 12.5 | 10.9 | 86.4 | 7.7 |
| 25 | 21.8 | 90.3 | 6.6 |
| 37.5 | 32.6 | 106.7 | 6.8 |
| 50 | 43.5 | 98.6 | 6.6 |
| 100 | 87.0 | 93.9 | 9.3 |
| 150 | 130.5 | 108.3 | 7.1 |
| 250 | 217.6 | 101.9 | 2.4 |
| 750 | 652.7 | 104.2 | 1.4 |
| 1000 | 870.2 | 104.3 | 10.9 |
| 3000 | 2610.6 | 112.4 | 15.1 |

Figure 14C:
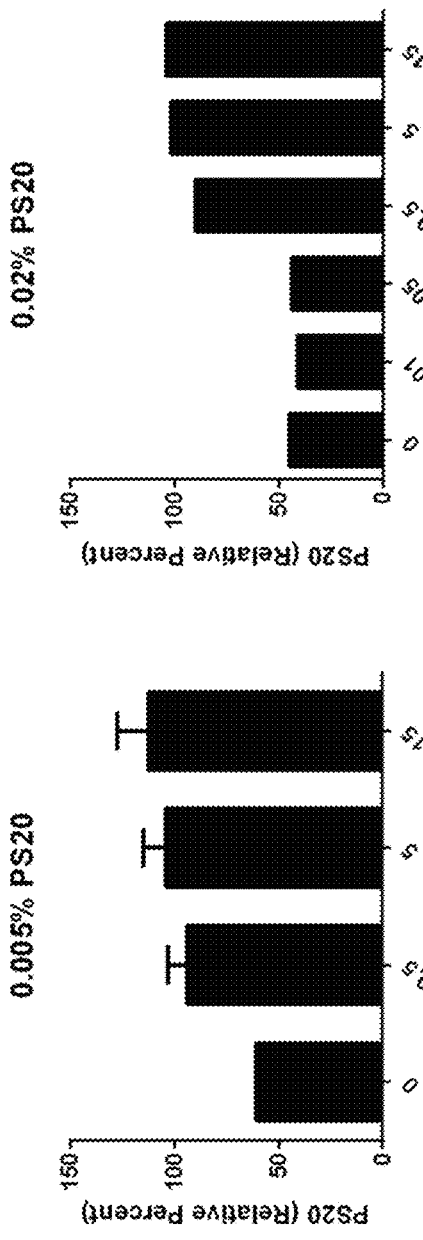
Figure 14D:
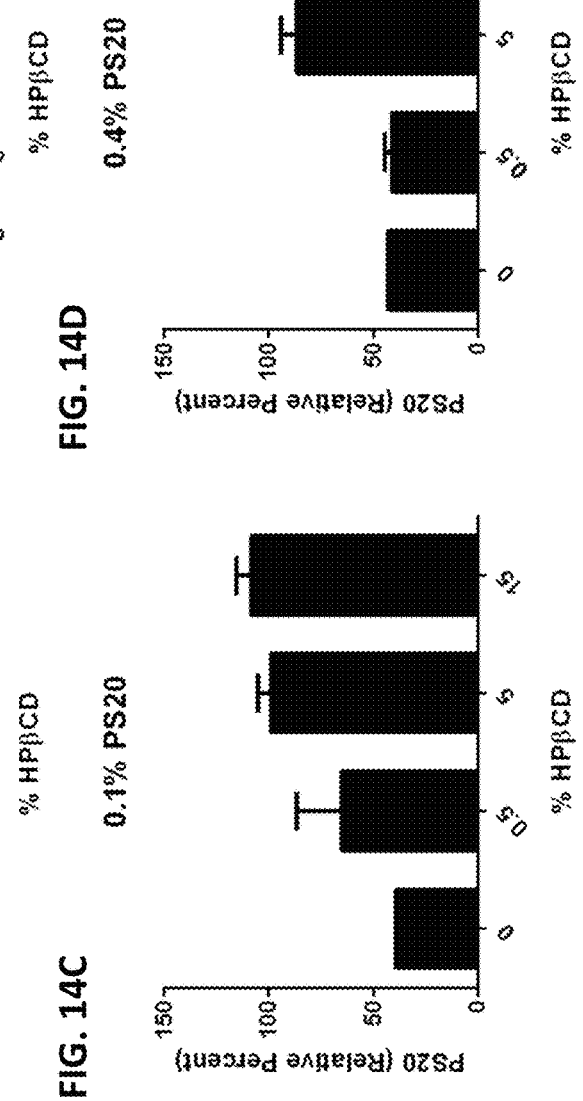
Figure 15A:
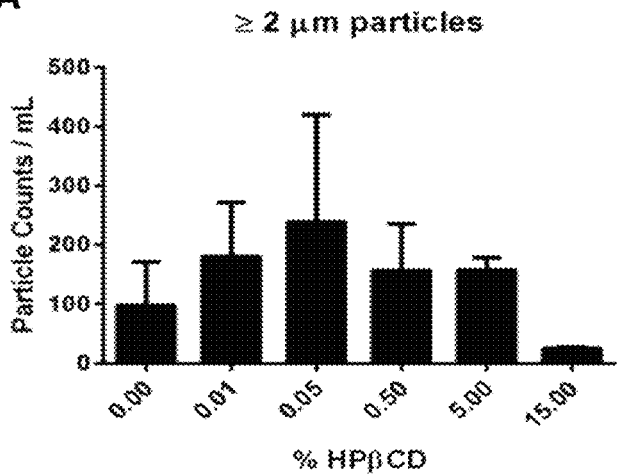
FIGS. 15A-15C display panel bar plot displays the average (n=3) (FIG. 15A) ≥2 µM, (FIG. 15B) ≥5 µM, (FIG. 15C) ≥10 µM particle counts per milliliter determined by HIAC for samples digested using 15 µg/mL of PPL enzyme for 4.5 hours at room temperature in protein-free samples containing 0.02% PS20 and 0, 0.1, 0.5, 5, and 15% (w/v) HP-β-CD.
Figure 15B:
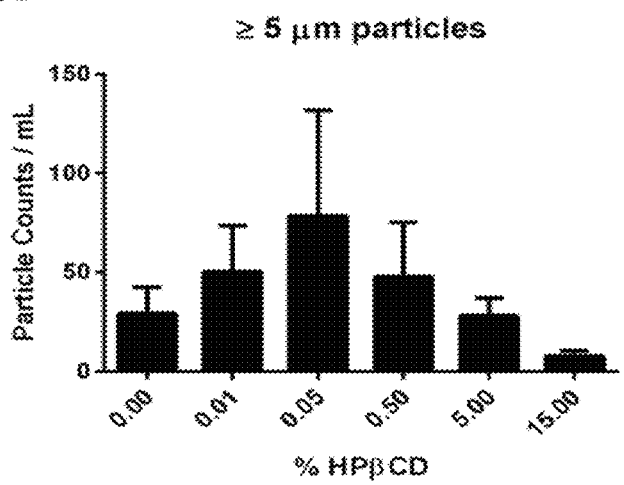
Figure 15C:
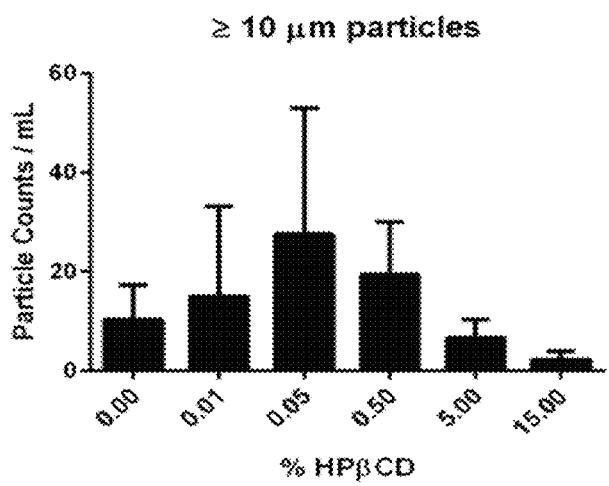

The amount of cyclodextrin is required for complete inhibition of enzymatic PS20 degradation depends on the concentration of PS20 (FIGS. 13 and 14A-D). At lower PS20 concentration (e.g., 0.005% PS20 (FIG. 14A), only 0.5% HP-β-CD is required to fully inhibit PS20 degradation whereas 15% HP-β-CD is required for samples containing 0.1% PS20 (FIG. 14C). Similarly, formation of sub-visible particles greater than 2, 5, or 10μ in diameter is dependent on the ratio of cyclodextrin to polysorbate. Samples containing 0.02% PS20 required 0.5% HP-β-CD to partially inhibit sub-visible particle formation and 15% HP-β-CD to completely inhibit sub-visible particle formation (FIGS. 15A-15C)

Figure 16:
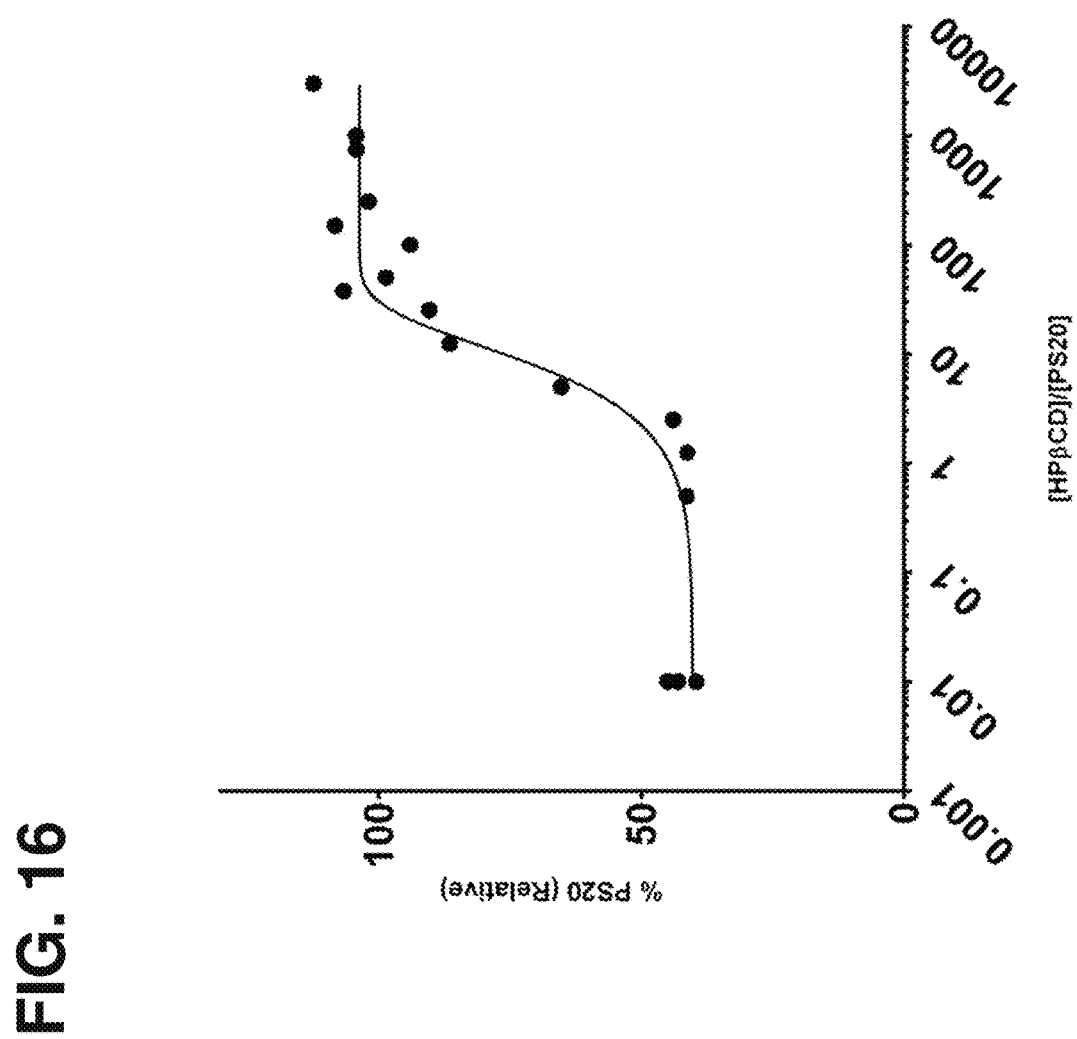
FIG. 16 displays the average (n=3) relative percent of PS20 determined by RP-ELSD for samples digested using 15 µg/mL of PPL enzyme for 4.5 hours at room temperature in protein-free samples containing different HP-β-CD to PS20 molar ratios. Data is fit using a sigmoidal model.

These results can be interpreted in the context of the HP-β-CD to PS20 ratio (w/w) (FIG. 16 and Table 2). The PS20 data demonstrate that sufficient HP-β-CD:PS20 (≥37.5 w/w) is required to inhibit enzymatic PS20 degradation (Table 2). The results suggest that the HP-β-CD to PS20 ratio is important in determining PS20 degradation across broad concentration ranges for PS20 and HP-β-CD.

The results also elucidate a possible mechanism of inhibition of PS20 degradation by HP-β-CD. In this case, the amount of PS20 degradation varies sigmoidally as the inhibitor (i.e., HP-β-CD) concentration is increased at fixed substrate (i.e., PS20) concentration (FIG. 13). Thus, without being bound by theory, increasing the cyclodextrin concentration may effectively reduce the free substrate concentration in solution which decreases the rate of PS20 degradation. Alternatively, it is possible that the PS20 degradation rate is inhibited by the substrate-inhibitor complex.

Example 9: Polysorbate Degradation Under Antibody Storage Conditions

The impact of various protein molecule classes (e.g., monoclonal antibody (mAb), single-Fab antibody (sFAb), and bispecific antibody (BsAb)) was assessed on the ability of cyclodextrins to decrease enzymatic PS20 degradation. The mAb, sFAb, and BsAb drug substance samples were provided in their native formulations. The samples were dialyzed and conditioned into the target formulation of 20 mM histidine acetate at pH 5.5 with 0.02% PS20 to a final protein concentration of 20 mg/mL. The control sample was prepared to contain 20 mM histidine acetate, pH 5.5, 0.02% PS20. Each of the mAb, sFAb, BsAb, and control samples were sub-aliquoted and adjusted using conditioning buffer to contain different amounts (0%, 5%, and 15%) HPβCD.

Samples were digested with 15 μg/mL PPL enzyme for 4.5 hours at room temperature, followed by 30 minutes of heat inactivation at 85 C. Each sample was analyzed for PS20 concentration using high performance liquid chromatography with an inline evaporative light scattering detector. Samples were then placed at 5° C. overnight to allow for the formation of particles and were analyzed for visible and subvisible particles as described above.

The results demonstrate that each sample containing 0% HPβCD has a different amount of PS20 degradation. The results show that the 0% HPβCD samples containing protein (FIGS. 17B-D) have higher amounts of PS20 degradation relative to the control sample (FIG. 17A). Because the proteins are expressed in Chinese hamster ovary (CHO) or E. Coli cells, the protein samples may contain other impurities (i.e., lipases, etc.) that contribute to the total amount of PS20 degradation.

Although the 0% HPβCD protein-containing samples were observed to have higher amounts of PS20 degradation, the results demonstrate that there are comparable amounts of PS20 degradation observed in samples containing 5% and 15% HPβCD. These results demonstrate that HPβCD is equally effective at mitigating catalytic PS20 degradation for all the molecular formats evaluated even though they may have different amounts of impurities that catalytically degrade PS20 (FIGS. 17A-D). This establishes that the presence of protein molecules and their native impurity profiles do not significantly affect the cyclodextrin to protein ratio that is necessary to mitigate PS20 degradation. Without being bound by theory, this finding suggests that the mechanism of catalytic inhibition involves cyclodextrin molecules directly interacting with the PS20, and not the enzyme that is degrading the polysorbate. Otherwise, the protein-containing samples, which contain additional enzymes that degrade polysorbate would require more HPβCD to mitigate the PS20 degradation compared to the control. Thus, the cyclodextrin to PS20 ratio described herein should be broadly applicable to a wide range of formulations containing different protein molecules and impurity profiles.

CONCLUSION

The studies performed show the ability of cyclodextrins to inhibit the enzymatic and oxidative degradation of polysorbates (PS20 and PS80). The results demonstrate that PVP and cyclodextrins (i.e., HP-α-CD, HP-β-CD, HP-γ-CD, SBE-β-CD) were able to prevent enzymatic degradation of PS20. Further experiments demonstrate that HP-β-CD is protective of polysorbate in the presence of multiple enzymes (i.e., CALB, RLE, LPL, and PLL). Without being bound by theory, the inhibitory mechanism may involve an interaction between the inhibitor (i.e., cyclodextrin) and the substrate (i.e., polysorbate). The inclusion complex formation may both reduce the concentration of free substrate and the inclusion complex may also be directly sterically inhibiting the interaction with the active site and the substrate. Additionally, concentration studies establish that there is an optimal range of HP-β-CD to PS20 ratio (≥37.5 w/w) that is necessary to provide complete inhibition of enzymatic PS20 degradation.

In addition to preventing enzymatic PS20 degradation, the results demonstrate that cyclodextrins can effectively reduce the amount of subvisible and visible particles. In this manner, cyclodextrins disaggregate and dissolve subvisible and visible particles in solution. In addition to effectively preventing the formation of particles, the results demonstrate that cyclodextrins also can effectively solubilize existing particles related to polysorbate degradation. Presumably, cyclodextrins also increase the solubility of free fatty acids that are products of polysorbate degradation.

The findings from this study have extensive practical implications. The results provide comprehensive evidence that formulation containing cyclodextrins may be used to prevent enzymatic polysorbate degradation. Additionally, cyclodextrins can be used to solubilize free fatty acids associated with polysorbate degradation from both oxidative and enzymatic degradation. Thus, cyclodextrins may also be useful as diluents or reconstitution buffers for drug products to dissolve degradants and particles associated with polysorbate degradation.

What is claimed is:

1. A method of reducing polysorbate degradation in an aqueous formulation comprising a polysorbate, the method comprising adding a cyclodextrin to the formulation, wherein the resulting w/w ratio of cyclodextrin to polysorbate is greater than about 37.5:1 and less than about 67:1; wherein the polysorbate degradation is reduced by about 50% or more.

2. A method of reducing polysorbate degradation in an aqueous formulation comprising a polysorbate, the method comprising adding a cyclodextrin to the formulation wherein the resulting w/w ratio of cyclodextrin to polysorbate is greater than about 37.5:1 and less than about 67:1, wherein the formulation comprises about 0.005%-0.4% polysorbate; wherein the polysorbate degradation is reduced by about 50% or more.

3. A method of reducing polysorbate degradation in an aqueous formulation comprising a polysorbate, the method comprising adding a cyclodextrin to the formulation to a concentration of about 0.01%-30%, wherein the resulting w/w ratio of cyclodextrin to polysorbate is greater than about 37.5:1 and less than about 67:1, wherein the formulation comprises about 0.005% to 0.4% polysorbate; wherein the polysorbate degradation is reduced by about 50% or more.

4. A method of reducing the amount of sub-visible and visible particles in an aqueous formulation comprising polysorbate, comprising adding a cyclodextrin to the formulation, wherein the resulting w/w ratio of cyclodextrin to polysorbate is greater than about 37.5:1 and less than about 67:1; wherein less than about 1,000 polysorbate particles greater than about 2 microns in diameter/mL are formed.

5. The method of claim 1, wherein the polysorbate is polysorbate 20 or polysorbate 80.

6. The method of claim 1, wherein the cyclodextrin is HP-β cyclodextrin, HP-γcyclodextrin, or sulfobutyl ether β-cyclodextrin.

7. The method of claim 1, wherein the concentration of polysorbate in the formulation is in the range of about 0.01% to 0.4%.

8. The method of claim 1, wherein the concentration of cyclodextrin in the formulation is in the range of about 0.5 to 30%.

9. The method of claim 1, wherein the polysorbate degradation is reduced by about 75%, about 80%, about 85%, about 90%, about 95% or about 99%.

10. The method of claim 1, wherein less than about 1,000, about 750, about 500, about 250, about 150, about 100, about 50, or about 25 polysorbate particles greater than about 2 microns in diameter/mL are formed.

11. The method of claim 1, wherein the formulation is stable at about 2° C. to about 8° C. for at least about six months, at least about 12 months, at least about 18 months, or at least about 24 months.

12. The method of claim 1, wherein the formulation is stable at about 1° C. to about 10° C. for at least about forty-eight months.

13. The method of claim 1, wherein the formulation is stable at about 2° C. to about 8° C. for at least about forty-eight months.

14. The method of claim 1, wherein the formulation further comprises a polypeptide.

15. The method of claim 14, wherein the polypeptide is an antibody.

16. The method of claim 15, wherein the antibody is a polyclonal antibody, a monoclonal antibody, a humanized antibody, a human antibody, a chimeric antibody, a multi-specific antibody or an antibody fragment.

17. The method of claim 14, wherein the polypeptide concentration in the formulation is about 1 mg/mL to about 250 mg/mL.

18. The method of claim 1, wherein the formulation has a pH of about 4.5 to about 7.0.

19. The method of claim 1, wherein the formulation further comprises one or more excipients selected from the group consisting of a stabilizer, a buffer, a surfactant, and a tonicity agent.

20. The method of claim 1, wherein the formulation is a pharmaceutical formulation suitable for administration to a subject.

21. The method of claim 1, wherein the formulation is pharmaceutical formulation suitable for intravenous, subcutaneous, intramuscular, or intravitreal administration to a subject.

22. The method of claim 1, wherein the polysorbate degradation is enzymatic polysorbate degradation.

23. The method of claim 15, wherein the antibody is produced recombinantly.

24. The method of claim 23, wherein the antibody is produced in Chinese hamster ovary cells.

* * * * *